United States Patent
Sugimura et al.

[11] Patent Number: 5,643,908
[45] Date of Patent: Jul. 1, 1997

[54] COLLAGENASE INHIBITOR

[75] Inventors: Yukio Sugimura; Kazuhiko Tamaki; Tomowo Kobayashi; Kazuhiko Tanzawa, all of Tokyo, Japan

[73] Assignee: Sankyo Company, Limited, Tokyo, Japan

[21] Appl. No.: 232,119

[22] PCT Filed: Nov. 2, 1992

[86] PCT No.: PCT/JP92/01420

§ 371 Date: Jun. 27, 1994

§ 102(e) Date: Jun. 27, 1994

[87] PCT Pub. No.: WO93/09097

PCT Pub. Date: May 13, 1993

[30] Foreign Application Priority Data

Nov. 8, 1991  [JP]  Japan ................. 3-292884

[51] Int. Cl.⁶ ................. A61K 31/50; C07D 237/04; C07D 403/12; C07D 413/12
[52] U.S. Cl. ................. 514/247; 514/236.5; 514/252; 544/114; 544/224; 544/238; 544/236; 548/229; 560/81; 560/157; 560/158; 560/190; 560/197
[58] Field of Search ................. 544/224, 238, 544/114; 514/236.5, 247, 252

[56] References Cited

U.S. PATENT DOCUMENTS

| | | | |
|---|---|---|---|
| 4,604,407 | 8/1986 | Haslanger et al. | 514/575 |
| 4,659,711 | 4/1987 | Huang et al. | 514/247 |
| 5,387,610 | 2/1995 | Gray et al. | 514/575 |

FOREIGN PATENT DOCUMENTS

| | | |
|---|---|---|
| 3-53891 | 3/1991 | Japan . |
| 3-157372 | 7/1991 | Japan . |
| WO91/17982 | 11/1991 | WIPO . |

OTHER PUBLICATIONS

Abstract for JP 3-157372 (Jul. 5, 1991).
Abstract for JP 3-53891 (Mar. 7, 1991).
Reich et al, *Cancer Research* 48 pp. 3307–3312 (1988).

*Advanced Organic Chemistry* by Jerry March (2nd. Ed.) pp. 363–365, 384–385 (1977).

*Protective Groups in Organic Chemistry*, J.F.W. McOmie (Editor), pp. 43–50, 183–198 (1973).

*Primary Examiner*—Emily Bernhardt
*Attorney, Agent, or Firm*—Frishauf, Holtz, Goodman, Langer & Chick, P.C.

[57] ABSTRACT

Compounds having inhibitory activity against inhibitory activity against type IV collagenase and are useful as angiogenesis, cancer infiltration or cancer metastasis inhibitors. The compounds have the formula:

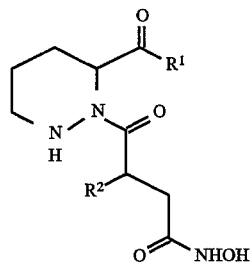

in which $R^1$ represents a group of formula:

—$OR^3$ (wherein $R^3$ represents a hydrogen atom or an alkyl group),

—$NR^4R^5$ (wherein $R^4$ and $R^5$ each represents a hydrogen atom, an alkyl or alkoxy group), —$NHCH(R^6COR^7$ (wherein $R^6$ represents a hydrogen atom or an alkyl group having 1 to 4 carbon atoms, and $R^7$ represents an alkyl group), —$NHCH(R^6)COOR^8$ (wherein $R^8$ represents an alkyl group) or —$NHCH(R^6)CONR^9R^{10}$ (wherein $R^9$ and $R^{10}$ each represents a hydrogen atom or an alkyl group, or $NR^9R^{10}$ together represent a heterocyclic ring group); and $R^2$ represents a hydrogen atom, an alkyl or aralkyl group.

16 Claims, No Drawings

5,643,908

1

COLLAGENASE INHIBITOR

This application is a 371 of PCT/JP92/01420 filed Nov. 2, 1992.

TECHNICAL FIELD

The present invention relates to novel piperazic acid derivatives having excellent collagenase inhibiting activity.

BACKGROUND ART

Collagenase degrades collagen, which is one of the main components of the connective tissues. Of the collagenases, type IV collagenases degrade type IV collagen, which is a main component of the basement membranes. It is known that the activity of type IV collagenases is raised at the time of angiogenesis accompanied by cancer growth and at the time of cancer invasion and metastasis, and that these enzymes play an important role in the degradation of the basement membranes [William G. Stetler-Stevenson; Cancer and Metastasis Reviews, Vol. 9, 289–303 (1990)]. Accordingly, a collagenase inhibitor may be useful for the prevention and treatment of these diseases.

Hitherto, there have been reports concerning low molecular weight substances showing collagenase inhibiting effects, including peptide compounds containing a mercapto group [Robert D. Gray, Hossain H. Saneii and Arno F. Spatola: Biochemical and Biophysical Research Communications, Vol. 101, No. 4, 1251–1258 (1981); Charles F. Vencill, David Rasnick, Katherine V. Crumley, Norikazu Nishino and James C. Powers: Biochemistry, Vol. 24, 3149–3157 (1985)]; peptide compounds containing a carboxyl group [Jean-Marie Delaisse, Yves Eeckhout, Christopher Sear, Alan Galloway, Keith McCullagh and Gilbert Vaes: Biochemical and Biophysical Research Communications, Vol. 133, 483–490 (1985)]; benzyloxycarbonyl propyl-leucyl-glycylhydroxamic acid [William M. Moore and Curtis A. Spilburg: Biochemical and Biophysical Research Communications, Vol. 136, 390–395 (1986)]; and hydroxylamine derivatives (Japanese Patent Kokai Application Hei No. 1-160997). Furthermore, SC 44463 has been reported [Reuven Reich, Erik W. Thompson, Yukihide Iwamoto, George R. Martin, James R. Deason, George C. Fuller and Ruth Miskin: Cancer Research, Vol. 48, 3307–3312 (1988)] as an inhibitor relatively specific to type IV collagenases. SC 44463 has been confirmed to exhibit an inhibitory activity on cancer metastasis in an animal experiment. The above compounds, however, are synthetic ones and are not yet put to practical use.

On the other hand, the tissue inhibitor of metalloproteinase (TIMP) and related substances are known as collagenase inhibitors of the protein type. It becomes possible to prepare TIMP on a large scale by recombinant DNA technology, but it has not yet been put to practical use [A. J. P. Docherty, A. Lyons, B. J. Smith, E. M. Wright, P. E. Stephens, T. J. R. Harris, G. Murghy and J. J. Reynolds: Sequence of human tissue inhibitor of metalloproteinases and its identity to erythroid-potentiating activity; Nature, Vol. 318, 66–69 (1985)].

As a compound having a hydroxylamino-substituted 2-pentylsuccinic acid structure, actinonin has been isolated from the culture filtrate of actinomycetes. This compound has been reported to inhibit aminopeptidase M at low concentrations [H. Umezawa, T. Aoyagi, T. Tanaka, T. Suda, A. Okuyama, H. Naganawa, M. Hamada and T. Takeuchi: J. Antibiotics, Vol. 38, 1629–1630 (1985)], however, it has not been investigated whether or not it inhibits type IV collagenases.

Furthermore, a natural product having the following chemical structure has been isolated from a strain which belongs to streptomyces and is known to have antibacterial and collagenase inhibiting activities (Japanese Patent Kokai Application Hei 3-157372).

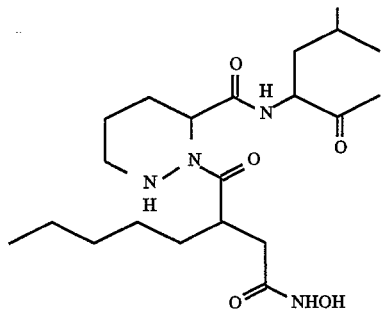

In addition, in Japanese Patent Kokai Application Hei 3-53891, the formula

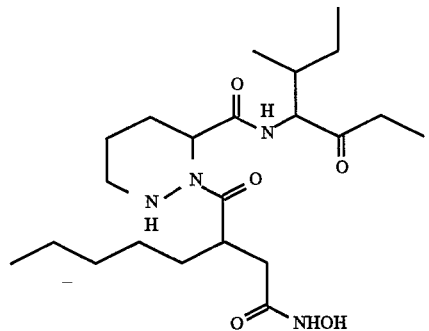

of the compound is described, and the compound is said to have antibacterial activity, however, there is no disclosure of its inhibitory activity on type IV collagenases.

DISCLOSURE OF INVENTION

The present inventors have eagerly studied the synthesis of derivatives having better inhibitory activity against type IV collagenases and the pharmacological activities of these derivatives. The study resulted in the finding that new matlystatin derivatives have excellent inhibitory activity against type IV collagenases and that these derivatives can be useful inhibitors of angiogenesis, inhibitors of cancer invasion and inhibitors of cancer metastasis; and they completed the present invention.

CONSTITUTION OF THE INVENTION

The compounds of the present invention have the general formula:

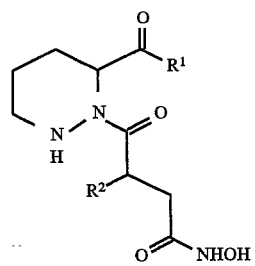

1

In the above formula, $R^1$ represents a group of formula: —$OR^3$ (wherein $R^3$ represents a hydrogen atom or an alkyl group containing 1 to 4 carbon atoms), —NR$^4$R$^5$ (wherein R$^4$ and R$^5$ are the same or different and each represents a hydrogen atom, an alkyl group containing 1 to 4 carbon atoms or an alkoxy group containing 1 to 4 carbon atoms), —NHCH(R$^6$)COR$^7$ (wherein R$^6$ represents a hydrogen atom or an alkyl group containing 1 to 4 carbon atoms and R$^7$ represents an alkyl group containing 1 to 4 carbon atoms), —NHCH(R$^6$)COOR$^8$ (wherein R$^6$ is as defined above and R$^8$ represents an alkyl group containing 1 to 4 carbon atoms) or —NHCH(R$^6$)CONR$^9$R$^{10}$ (wherein R$^6$ is as defined above, and R$^9$ and R$^{10}$ are the same or different and each represents a hydrogen atom or an alkyl group containing 1 to 4 carbon atoms, or NR$^9$R$^{10}$ together represent a heterocyclic ring group); and R$^2$ represents a hydrogen atom, an alkyl group containing 3 to 16 carbon atoms or an aralkyl group comprising an optionally substituted phenyl group and an alkyl group containing 1 to 4 carbon atoms.

However, those compounds in which R$^1$ represents a group of formula: —NHCH(R$^{6a}$) COR$^{7a}$ (wherein the combination of R$^{6a}$ and R$^{7a}$ signifies the isobutyl and methyl groups or the ethyl and sec-butyl groups) and R$^2$ represents a pentyl group are excluded.

In the said formula (1), the term "alkyl" used in connection with an alkyl group containing 1 to 4 carbon atoms represented by R$^3$, R$^4$, R$^5$, R$^6$, R$^7$, R$^8$, R$^9$ and R$^{10}$ falling under the definition of R$^1$ an alkyl moiety of an alkoxy group containing 1 to 4 carbon atoms represented by R$^4$ and R$^5$ and an alkyl moiety containing 1 to 4 carbon atoms of an aralkyl group falling under the definition of R$^2$ signifies a straight or branched chain alkyl group containing 1 to 4 carbon atoms, such as a methyl, ethyl, n-propyl, isopropyl, n-butyl, isobutyl, sec-butyl or tert-butyl group; preferably, in the case of R$^6$ falling under the definition of R$^1$, a methyl isopropyl isobutyl or sec-butyl group, and, in the case of the other R's, an alkyl group containing 1 or 2 carbon atoms.

In the said formula (1), where R$^2$ represents an aralkyl group, examples of the substituents on the phenyl moiety include an alkyl group such as a methyl or ethyl group, an alkoxy group such as a methoxy or ethoxy group, and a halogen atom such as chlorine or bromine.

In the said formula (1), where R$^2$ represents an aralkyl group, preferred examples of the complete aralkyl group include an unsubstituted benzyl or phenethyl group.

In the said formula (1), where R$^1$ represents a heterocyclic ring group represented by NR$^9$R$^{10}$ together, examples of such heterocyclic ring groups include nitrogen-containing heterocyclic groups such as pyrrolidin-1-yl, imidazolin-1-yl, pyrazolidin-1-yl, pyrazolin-1-yl, piperidino, piperazin-1-yl and morpholino groups preferably pyrrolidin-1-yl, piperidino and morpholino groups.

In the said formula (1), where R$^2$ represents an alkyl group containing 3 to 16 carbon atoms, it signifies a straight or branched chain alkyl group such as an n-propyl, isopropyl, n-butyl, isobutyl, sec-butyl, tert-butyl, n-pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, n-heptyl, 1-methylhexyl, 2-methylhexyl, 3-methylhexyl, 4-methylhexyl, 5-methylhexyl, 1-propylbutyl, 4,4-dimethylpentyl, n-octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, n-nonyl, 3-methyloctyl, 4-methyloctyl, 5-methyloctyl, 6-methyloctyl, 1-propylhexyl, 2-ethylheptyl, 6,6-dimethylheptyl, n-decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl or 13,13-dimethyltetradecyl group; preferably an alkyl group containing 4 to 12 carbon atoms; and more preferably an alkyl group containing 6 to 10 carbon atoms.

Preferred compounds are those in which:

2)
R$^1$ represents a group of formula:
—OR$^3$ (wherein R$^3$ represents a hydrogen atom or an alkyl group containing 1 to 4 carbon atoms);
—NR$^4$R$^5$ (wherein R$^4$ and R$^5$ are the same or different and each represents a hydrogen atom, an alkyl group containing 1 to 4 carbon atoms or an alkoxy group containing 1 to 4 carbon atoms);
—NHCH(R$^6$)COR$^7$ (wherein R$^6$ represents a hydrogen atom or an alkyl group containing 1 to 4 carbon atoms, and R$^7$ represents an alkyl group containing 1 to 4 carbon atoms); or
—NHCH(R$^6$)CONR$^9$R$^{10}$ (wherein R$^6$ is as defined above, and R$^9$ and R$^{10}$ are the same or different and each represents a hydrogen atom or an alkyl group containing 1 to 4 carbon atoms, or NR$^9$R$^{10}$ together represents a heterocyclic ring group); and R$^2$ represents a hydrogen atom, an alkyl group containing 3 to 16 carbon atoms or an aralkyl group comprising an optionally substituted phenyl group and an alkyl group Containing 1 to 4 carbon atoms;

3)
R$^1$ represents a group of formula:
—OR$^3$ (wherein R$^3$ represents a hydrogen atom or an alkyl group containing 1 to 4 carbon atoms);
—NR$^4$R$^5$ (wherein R$^4$ and R$^5$ are the same or different and each represents a hydrogen atom or an alkyl group containing 1 to 4 carbon atoms); or
—NHCH(R$^6$)COR$^7$ (wherein R$^6$ represents a hydrogen atom or an alkyl group containing 1 to 4 carbon atoms, and R$^7$ represents an alkyl group containing 1 to 4 carbon atoms); and R$^2$ represents a hydrogen atom, an alkyl group containing 3 to 16 carbon atoms or an aralkyl group comprising an optionally substituted phenyl group and an alkyl group containing 1 to 4 carbon atoms;

4)
R$^1$ represents a group of formula: —NR$^4$R$^5$ (wherein R$^4$ and R$^5$ are the same or different and each represents a hydrogen atom or an alkyl group containing 1 to 4 carbon atoms); and R$^2$ represents an alkyl group containing 3 to 16 carbon atoms or an aralkyl group comprising an optionally substituted phenyl group and an alkyl group containing 1 or 2 carbon atoms; and 5)
R$^1$ represents a group of formula: —NR$^4$R$^5$ (wherein R$^4$ and R$^5$ are the same or different and each represents a hydrogen atom or an alkyl group containing 1 to 4 carbon atoms); and $R^2$ represents an alkyl group containing 6 to 10 carbon atoms.

The compounds of formula (1) in accordance with the invention can exist in various stereoisomeric forms due to the presence of asymmetric carbon atoms having the R- and/or S-configuration. Although all of the isomers are represented herein by a single formula, the present invention covers not only mixtures of the isomers but also each of the individual isomers.

Examples of the compounds of the invention are listed in Table 1. Such examples are not to be construed as being limitative of the invention.

In Table 1 the abbreviations used have the following significance.

Me: methyl group;
Et: ethyl group;
Pr: propyl group;
iPr: isopropyl group;
sBu: sec-butyl group;
iBu: isobutyl group;
Pen: pentyl group;
Hex: hexyl group;
Hep: heptyl group;
Oct: octyl group;
Dec: decyl group;
Ph: phenyl group;
PhE: phenethyl group;
Am: amyl group;
Pyrd: pyrrolidin-1-yl group;
Imid: imidazolidin-1-yl group;
Pyzr: pyrazolidin-1-yl group;
Pyz: pyrazolin-1-yl group;
Pipe: piperidino group;
Pipr: piperazin-1-yl group; and
Mor: morpholino group.

TABLE 1

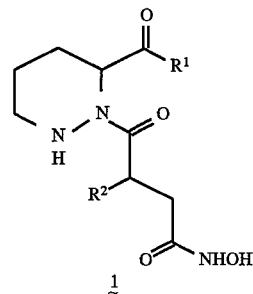

| Compound No. | R¹ | R² |
|---|---|---|
| 1 | OMe | Pen |
| 2 | OMe | iBu |
| 3 | OMe | Oct |
| 4 | OMe | H |
| 5 | OtBu | Pen |
| 6 | OtBu | iBu |
| 7 | OtBu | Oct |
| 8 | OtBu | Hex |
| 9 | OtBu | Hep |
| 10 | OtBu | Dec |
| 11 | OtBu | PhE |
| 12 | OtBu | H |
| 13 | HNMe | Pen |
| 14 | HNMe | iBu |
| 15 | HNMe | Oct |
| 16 | HNMe | Hex |
| 17 | HNMe | Hep |
| 18 | HNMe | Dec |
| 19 | HNMe | PhE |
| 20 | HNMe | Et |
| 21 | HNMe | Me |
| 22 | HNMe | Pr |
| 23 | HNMe | Bu |
| 24 | N(Me)₂ | Pen |
| 25 | N(Me)₂ | iBu |
| 26 | N(Me)₂ | Oct |
| 27 | N(Me)₂ | Hex |
| 28 | N(Me)₂ | Hep |
| 29 | N(Me)₂ | Dec |
| 30 | N(Me)₂ | PhE |
| 31 | N(Me)₂ | Et |
| 32 | N(Me)₂ | H |
| 33 | N(Me)OMe | Pen |
| 34 | N(Me)OMe | iBu |
| 35 | N(Me)OMe | Oct |
| 36 | N(Me)OMe | Et |
| 37 | N(Me)OMe | H |
| 38 | NHOMe | Pen |
| 39 | NHOMe | iBu |
| 40 | NHOMe | Oct |
| 41 | NHOMe | Et |
| 42 | NHOMe | H |
| 43 | NHPh | Pen |
| 44 | NHPh | iBu |
| 45 | NHPh | Oct |
| 46 | NHPh | Et |
| 47 | NHPh | H |
| 48 | NHCH₂Ph | Pen |
| 49 | NHCH₂Ph | iBu |
| 50 | NHiBu | Pen |
| 51 | NHiBu | iBu |
| 52 | NHiAm | Pen |
| 53 | NHiAm | iBu |
| 54 | HNCH(iPr)COEt | Pen |
| 55 | HNCH(iPr)COEt | iBu |
| 56 | HNCH(iPr)COEt | Oct |
| 57 | HNCH(iPr)COEt | Et |
| 58 | HNCH(iPr)COEt | H |
| 60 | HNCH(iBu)COEt | iBu |
| 61 | HNCH(iBu)COEt | Oct |
| 62 | HNCH(iBu)COEt | Et |
| 63 | HNCH(iBu)COEt | H |
| 64 | HNCH(sBu)COEt | iBu |
| 65 | HNCH(sBu)COEt | Oct |
| 66 | HNCH(sBu)COEt | Et |
| 67 | HNCH(sBu)COEt | H |
| 68 | HNCH(iPr)COOMe | Pen |
| 69 | HNCH(iPr)COOMe | iBu |
| 70 | HNCH(iPr)COOMe | Oct |
| 71 | HNCH(iPr)COOMe | Et |
| 72 | HNCH(iPr)COOMe | H |
| 73 | HNCH(iPr)CONHMe | Pen |
| 74 | HNCH(iPr)CONHMe | iBu |
| 75 | HNCH(iPr)CONHMe | Oct |
| 76 | HNCH(iPr)CONHMe | Et |

TABLE 1-continued

Structure 1: cyclic hydrazide with R¹ carbonyl group and R² substituent on chain bearing NHOH hydroxamic acid.

| Compound No. | R¹ | R² |
|---|---|---|
| 77 | HNCH(iPr)CONHMe | H |
| 78 | HNCH(iPr)COOtBu | Pen |
| 79 | HNCH(iPr)COOtBu | iBu |
| 80 | HNCH(iPr)COOtBu | Oct |
| 81 | HNCH(iPr)COOtBu | H |
| 82 | HNCH(iPr)CON(Me)OMe | Pen |
| 83 | HNCH(iPr)CON(Me)OMe | iBu |
| 84 | HNCH(iPr)CON(Me)OMe | Oct |
| 85 | HNCH(iPr)CON(Me)OMe | H |
| 86 | HNCH₂COOMe | Pen |
| 87 | HNCH₂COOMe | iBu |
| 88 | HNCH₂COOMe | Oct |
| 89 | HNCH₂CONHMe | Pen |
| 90 | HNCH₂CONHMe | iBu |
| 91 | HNCH₂CONHMe | Oct |
| 92 | HNCH₂CON(Me)₂ | Pen |
| 93 | HNCH₂CON(Me)₂ | iBu |
| 94 | HNCH₂CON(Me)₂ | Oct |
| 95 | HNCH(Me)COOMe | Pen |
| 96 | HNCH(Me)COOMe | iBu |
| 97 | HNCH(Me)COOMe | Oct |
| 98 | HNCH(Me)CONHMe | Pen |
| 99 | HNCH(Me)CONHMe | iBu |
| 100 | HNCH(Me)CONHMe | Oct |
| 101 | N(Me)CH₂COOMe | Pen |
| 102 | N(Me)CH₂COOMe | iBu |
| 103 | N(Me)CH₂COOMe | Oct |
| 104 | N(Me)CH₂CONHMe | Pen |
| 105 | N(Me)CH₂CONHMe | iBu |
| 106 | N(Me)CH₂CONHMe | Oct |
| 107 | HNCH(Ph)COOMe | Pen |
| 108 | HNCH(Ph)COOMe | iBu |
| 109 | HNCH(Ph)COOMe | Oct |
| 110 | HNCH(Ph)CONHMe | Pen |
| 111 | HNCH(Ph)CONHMe | iBu |
| 112 | HNCH(Ph)CONHMe | Oct |
| 113 | HNCH(CH₂Ph)COOMe | Pen |
| 114 | HNCH(CH₂Ph)COOMe | iBu |
| 115 | HNCH(CH₂Ph)COOMe | Oct |
| 116 | HNCH(CH₂Ph)CONHMe | Pen |
| 117 | HNCH(CH₂Ph)CONHMe | iBu |
| 118 | HNCH(CH₂Ph)CONHMe | Oct |
| 119 | HNCH(iPr)CONH₂ | Pen |
| 120 | HNCH(iPr)CONH₂ | iBu |
| 121 | HNCH(iPr)CONH₂ | Oct |
| 122 | HN-c-Hx | Pen |
| 123 | HN-c-Hx | Oct |
| 124 | HN-c-Hx | iBu |
| 125 | HNCH(CH₂OMe)COOMe | Pen |
| 126 | HNCH(CH₂OMe)COOMe | iBu |
| 127 | HNCH(CH₂OMe)COOMe | Oct |
| 128 | HNCH₂CONH₂ | Pen |
| 129 | HNCH₂CONH₂ | iBu |
| 130 | HNCH₂CONH₂ | Oct |
| 131 | HNMe | H |
| 132 | HNMe | H |
| 133 | N(Me)OMe | H |
| 134 | NHOMe | H |
| 135 | NHPh | H |
| 136 | Pyrd | Pen |

| Compound No. | R¹ | R² |
|---|---|---|
| 137 | Pyrd | iBu |
| 138 | Pyrd | Oct |
| 139 | Pyrd | Hex |
| 140 | Pyrd | Hep |
| 141 | Pyrd | Dec |
| 142 | Imid | Pen |
| 143 | Imid | iBu |
| 144 | Imid | Oct |
| 145 | Imid | Hex |
| 146 | Imid | Hep |
| 147 | Imid | Dec |
| 148 | Pyzr | Pen |
| 149 | Pyzr | iBu |
| 150 | Pyzr | Oct |
| 151 | Pyzr | Hex |
| 152 | Pyzr | Hep |
| 153 | Pyzr | Dec |
| 154 | Pyz | Pen |
| 155 | Pyz | iBu |
| 156 | Pyz | Oct |
| 157 | Pyz | Hex |
| 158 | Pyz | Hep |
| 159 | Pyz | Dec |
| 160 | Pipe | Pen |
| 161 | Pipe | iBu |
| 162 | Pipe | Oct |
| 163 | Pipe | Hex |
| 164 | Pipe | Hep |
| 165 | Pipe | Dec |
| 166 | Pipr | Pen |
| 167 | Pipr | iBu |
| 168 | Pipr | Oct |
| 169 | Pipr | Hex |
| 170 | Pipr | Hep |
| 171 | Pipr | Dec |
| 172 | Mor | Pen |
| 173 | Mor | iBu |
| 174 | Mor | Oct |
| 175 | Mor | Hex |
| 176 | Mor | Hep |
| 177 | Mor | Dec |

Of the compounds illustrated in the above table, preferred compounds are Compounds No. 1, 2, 3, 4, 5, 6, 7, 13, 14, 15, 16, 17, 18, 19, 23, 24, 25, 26, 27, 28, 29, 30, 33, 34, 35, 54, 55, 56, 60, 61, 62, 64, 65, 66, 67, 68, 69, 73, 74, 82, 83, 86, 87, 88, 89, 90, 91 95, 101, 104 and 107. The more preferred compounds are Compounds No. 1, 2, 3, 5, 6, 13, 14, 15, 16, 17, 18, 19, 24, 26, 27, 28, 29, 30, 54, 55, 56, 60 and 64. The most preferred compounds are:

$N^2$-[2-(R)-(Hydroxyaminocarbonyl)methyl-1-oxoheptyl]-(S)-piperazic acid N-methylamide, $N^2$-[2-(R)-(Hydroxyaminocarbonyl)methyl-1-oxooctyl]-(S)-piperazic acid N-methylamide, $N^2$-[2-(R)-(Hydroxyaminocarbonyl)methyl-1-oxononyl]-(S)-piperazic acid N-methylamide, $N^2$-[2-(R)-(Hydroxyaminocarbonyl)methyl-1-oxodecyl]-(S)-piperazic acid N-methylamide, $N^2$-[2-(R)-(Hydroxyaminocarbonyl)methyl-1-oxododecyl]-(S)-piperazic acid N-methylamide, $N^2$-[2-(R)-(Hydroxyaminocarbonyl)methyl-1-oxo-4-phenylbutyl]-(S)-piperazic acid N-methylamide, $N^2$-[2-(R)-(Hydroxyaminocarbonyl)methyl-1-oxoheptyl]-(S)-piperazic acid N,N-dimethylamide, $N^2$-[2-(R)-(Hydroxyaminocarbonyl)methyl-1-oxooctyl]-(S)-piperazic acid N,N-dimethylamide, $N^2$-[2-(R)-(Hydroxyaminocarbonyl)methyl-1-oxononyl]-(S)-piperazic acid N,N-dimethylamide, $N^2$-[2-(R)-(Hydroxyaminocarbonyl)methyl-1-oxodecyl]-(S)-piperazic acid N,N-dimethylamide, $N^2$-[2-(R)-(Hydroxyaminocarbonyl)methyl-1-oxododecyl]-(S)-piperazic acid N,N-dimethylamide, and $N^2$-[2-(R)-(Hydroxyaminocarbonyl)methyl-1-oxo-4-phenylbutyl]-(S)-piperazic acid N,N-dimethylamide.

The compounds of the invention can be prepared by the procedure summarized in the following scheme.

That is, the compounds of formula (1) of the invention can be prepared by ① reacting a compound (a), which is a key intermediate, with a compound (b) in the presence of a condensing agent to prepare a compound (c); ② removal of a protecting group, $B^4$, of the compound (c), to prepare a compound (d); ③ reacting a compound (d) with an alcohol or amine, $R^1H$, followed by removal of the protecting group, $B^4$, after which the product is reacted with a hydroxylamine, $B^6ONH_2$, to prepare a compound (e); and 4 removal of protecting groups, A and $B^6$.

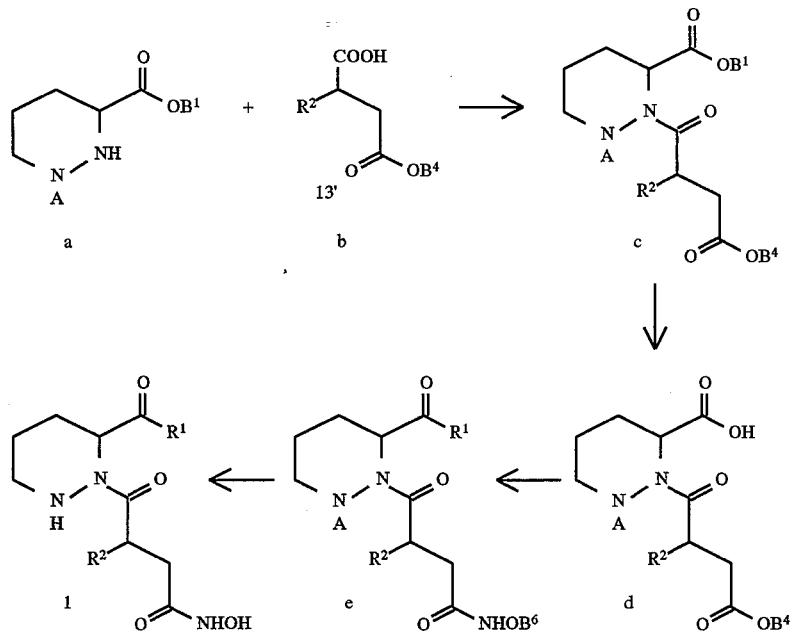

In the formula of the above reaction scheme, $R^1$ and $R^2$ are as defined above and the significance of A, $B^1$, $B^4$ and $B^6$ will be explained later. Furthermore, methods for the preparation of the compounds of the invention will be explained in detail.

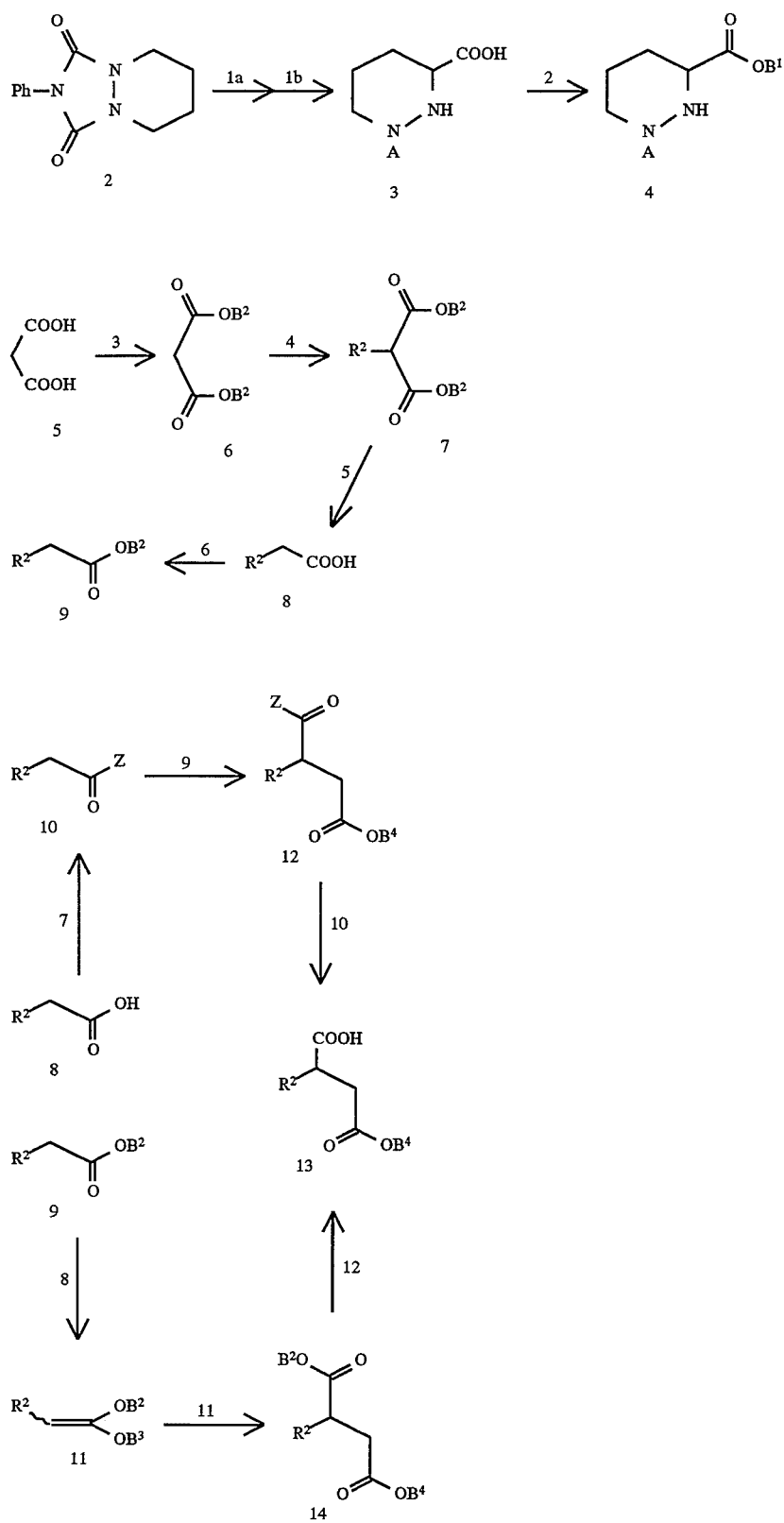

-continued
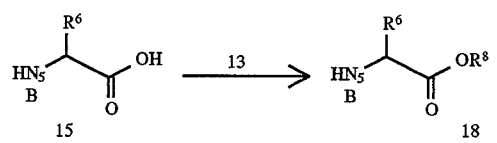
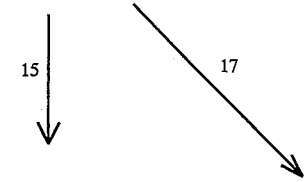
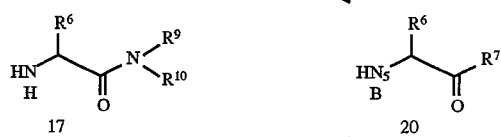
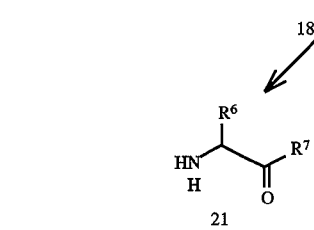
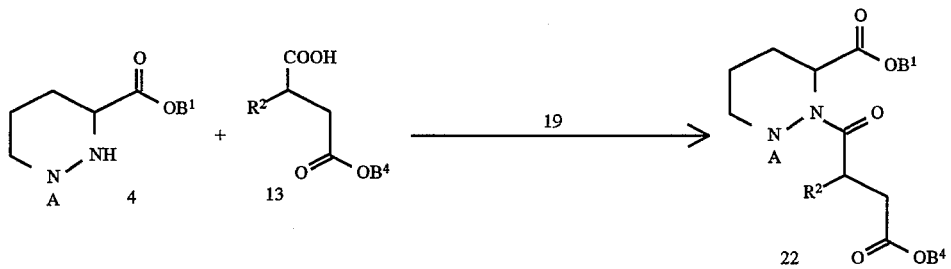
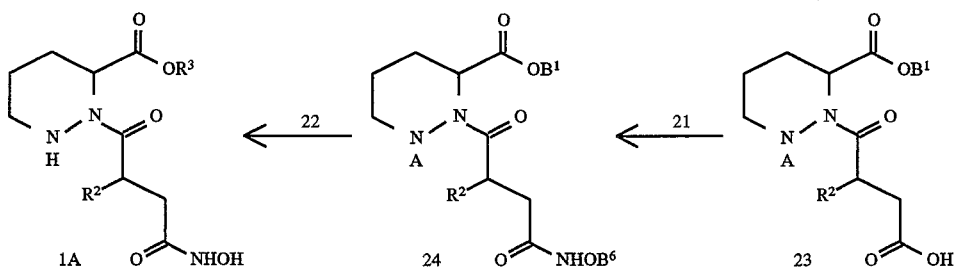

-continued

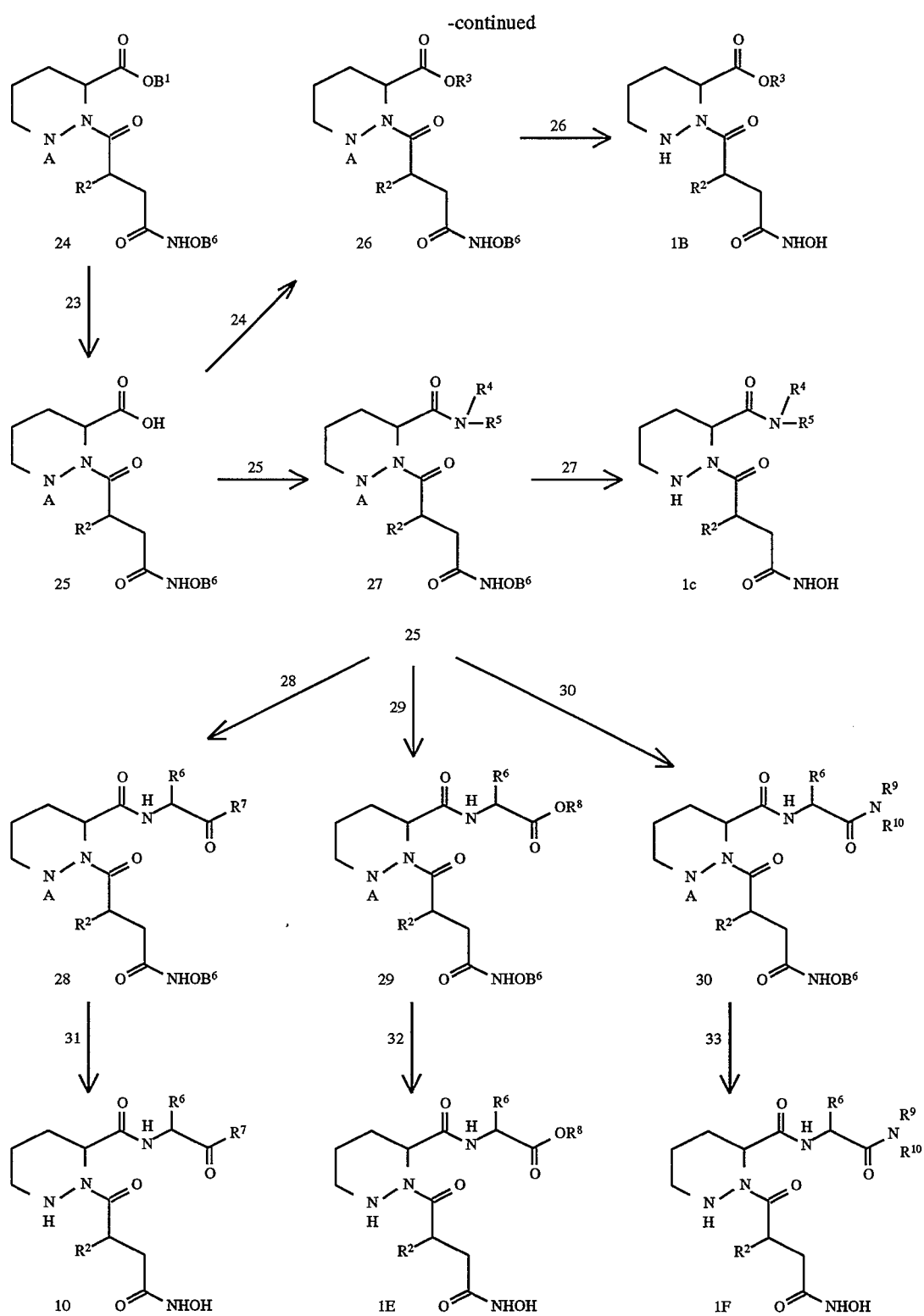

In the formulae of the above reaction scheme, $R^1$, $R^2$, $R^3$, $R^4$, $R^5$, $R^6$, $R^7$, $R^8$, $R^9$ and $R^{10}$ are as defined above; A represents an amino-protecting group (preferably a benzyloxycarbonyl group); $B^1$ represents a carboxyl-protecting group (preferably a tert-butyl or benzyl group); $B^2$ represents a carboxyl-protecting group (preferably a methyl or ethyl group); $B^3$ represents a tri-substituted silyl group (preferably a trimethylsilyl group); $B^4$ represents a carboxyl-protecting group (preferably a benzyl, tert-butyl, trichloroethyl or tribromoethyl group); $B^5$ represents an amino-protecting group (preferably a benzyloxycarbonyl, tert-butoxycarbonyl, allyloxycarbonyl or trichloroethoxycarbonyl group); $B^6$ represents a hydroxyl-protecting group (preferably a benzyl group); and Z represents an optically active 2-oxo-oxazolidinyl group. The compound (4) is either known from Massall, C. M., Johnson M. and Theobald C. J. [J. Chem. Soc. Perkin I, (1971), 1451] or can be produced according to the procedure of Steps 1a, 1b and 2 described below.

(Step 1a)

This step involves hydrolyzing a compound (2), which is known from Synthetic Communications 1988, 2225, in an inert solvent in the presence of a base.

There is no particular limitation upon the nature of the solvent used, provided that it has no adverse effect upon the reaction and can dissolve the starting material to some extent. Examples of such solvents include: aliphatic hydrocarbons such as hexane, heptane, ligroin or petroleum ether; aromatic hydrocarbons such as benzene, toluene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; alcohols such as methanol, ethanol, n-propanol, isopropanol, n-butanol, isobutanol, tert-butanol, isoamyl alcohol, diethylene glycol, glycerin, octanol, cyclohexanol or methyl cellosolve; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; amides such as formamide, dimethylformamide, dimethylacetamide or hexamethylphosphoramide; and sulfoxides such as dimethyl sulfoxide or sulfolane; preferably alcohols.

There is no particular limitation upon the nature of the base used, provided that it can be used as a base in conventional reactions. Examples of such bases include: alkali metal carbonates such as sodium carbonate, potassium carbonate or lithium carbonate; alkali metal hydrogencarbonates such as sodium hydrogencarbonate, potassium hydrogencarbonate or lithium hydrogencarbonate; alkali metal hydrides such as lithium hydride, sodium hydride or potassium hydride; and alkali metal hydroxides such as sodium hydroxide, potassium hydroxide, barium hydroxide or lithium hydroxide; preferably alkali metal hydroxides.

The reaction is usually carried out at a temperature of 20° to 200° C., preferably 50° to 130° C.

The time required for the reaction depends upon the reaction temperature and other factors, such as the nature of the starting material and of the solvent, but the reaction is usually complete within a period of 2 to 72 hours, preferably 5 to 24 hours.

After completion of the reaction, the desired compound can be isolated from the reaction mixture, for example, by distilling off the solvent; pouring the reaction mixture into water; acidifying with an inorganic acid such as hydrochloric acid or sulfuric acid; extracting with a water-immiscible solvent such as benzene, ether or ethyl acetate; and distilling off the solvent from the extract. The product thus obtained can usually be used for the following reaction without further purification but, if desired, can be purified by conventional means such as chromatography or recrystallization.

(Step 1b)

This step consists in protecting the amino group at the 1-position of the piperazic acid prepared in Step 1a in an inert solvent to produce a compound (3).

As a preferred amino-protecting group there come into consideration aralkyloxycarbonyl groups such as the benzyloxycarbonyl group.

The reaction can be carried out by using a reagent for preparing carbamates (preferably benzyloxycarbonyl chloride), which is commercially available or can readily be prepared, in an inert solvent in the presence of a base. There is no particular limitation upon the nature of the solvent used, provided that it has no adverse effects upon the reaction and can dissolve the starting material to some extent. Examples of such solvents include: aliphatic hydrocarbons such as hexane, heptane, ligroin or petroleum ether; aromatic hydrocarbons such as benzene, toluene or xylene; alcohols such as methanol, ethanol, n-propanol, isopropanol, n-butanol, isobutanol, tert-butanol, isoamyl alcohol, diethylene glycol, glycerin, octanol, cyclohexanol or methyl cellosolve; water; and a mixture of water and one or more of these organic solvents; preferably a mixture of water and the corresponding alcohols.

There is no particular limitation upon the nature of the base used, provided that it can be used as a base in conventional reactions. Examples of such bases include: inorganic bases, including alkali metal carbonates such as sodium carbonate, potassium carbonate or lithium carbonate; alkali metal hydrogencarbonates such as sodium hydrogencarbonate, potassium hydrogencarbonate or lithium hydrogencarbonate; alkali metal hydrides such as lithium hydride, sodium hydride or potassium hydride; and alkali metal hydroxides such as sodium hydroxide, potassium hydroxide, barium hydroxide or lithium hydroxide; and organic bases such as triethylamine, tributylamine, diisopropylethylamine, N-methylmorpholine, pyridine, 4-(N,N-dimethylamino)pyridine, N,N-dimethylaniline, N,N-diethylanilene, 1,5-diazabicyclo[4,3,0]non-5-ene (DBN), 1,4-diazabicyclo[2,2,2]octane (DABCO) or 1,8-diazabicyclo[5,4,0]undec-7-ene (DBU); preferably alkali metal hydroxides or organic bases.

The reaction is usually carried out at a temperature of 0° to 50° C., preferably 0° to 20° C.

The time required for the reaction depends upon the reaction temperature and other factors, such as the nature of the starting material and of the solvent, but the reaction is usually complete within a period of 1 to 24 hours, preferably 1 to 3 hours.

After completion of the reaction, the desired compound can be isolated from the reaction mixture, for example, by distilling off the solvent; pouring the reaction mixture into water; acidifying with an inorganic acid such as Hydrochloric acid or sulfuric acid; extracting with a water-immiscible solvent such as benzene, ether or ethyl acetate; and distilling off the solvent from the extract. The product thus obtained can usually be used in the following reaction without further purification but, if desired, can be purified by conventional means such as chromatography or recrystallization.

(Step 2)

In this step, a compound (4) can be prepared ① by reacting a compound (3) with an alcohol, $B^1OH$, (particularly benzyl alcohol or tert-butyl alcohol) in an inert solvent in the presence of a condensing agent or ② by reacting a compound (3) with an esterifying agent in an inert solvent.

In process ①, the nature of the solvent used is not particularly critical, provided that it has no adverse effect upon the reaction and can dissolve the starting material to some extent. Examples of preferred solvents include: aliphatic hydrocarbons such as hexane, heptane, ligroin or petroleum ether; aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; amides such as formamide, dimethylformamide, dimethylacetamide or hexamethylphosphoramide; and sulfoxides such as dimethyl sulfoxide or sulfolane; preferably aromatic hydrocarbons, ethers, halogenated hydrocarbons, nitriles or amides.

Examples of the condensing agents used include: for example, di(lower alkyl) azodicarboxylate-triphenylphosphine, such as diethyl azodicarbonylate-triphenylphosphine; N-(lower alkyl)-5-arylisoxazolium-3'-sulfonates such as N-ethyl-5-phenylisoxazolium-3'-sulfonate; N,N'-dicycloalkylcarbodiimides such as N,N'-dicyclohexylcarbodiimide (DCC); diheteroaryl diselenides such as dipyridyl diselenide; phosphines such as diethyl phosphoryl cyanide (DEPC); arylsulfonyl triazolides such as p-nitrobenzenesulfonyl triazolide; 2-halo-1-(lower alkyl) pyridinium halides such as 2-chloro-1-methylpyridinium iodide; diarylphosphoryl azides such as diphenylphosphoryl azide; imidazole derivatives such as N,N'-carbodiimidazole (CDI); benzotriazole derivatives such as 1-hydroxybenzotriazole (HOBT); dicarboximide derivatives such as N-hydroxy-5-norbornene-2,3-dicarboximide (HONB); and carbodiimides such as 1-ethyl-3-(3-dimethylaminopropyl)carbodiimide (EDAPC); preferably carbodiimides (particularly DCC and DEPC).

The reaction is usually carried out at a temperature of 0° to 100° C., preferably 10° to 50° C.

The time required for the reaction depends upon the reaction temperature and other factors, such as the nature of the starting material and of the solvent, but the reaction is usually complete within a period of 1 to 48 hours, preferably 1 to 12 hours.

After completion of the reaction, the desired compound can be isolated from the reaction mixture, for example, by distilling off the solvent; pouring the reaction mixture into water; acidifying with an inorganic acid such as hydrochloric acid or sulfuric acid; filtering off insoluble materials; extracting with a water-immiscible solvent such as benzene, ether or ethyl acetate; and distilling off the solvent from the extract. The product thus obtained can usually be used in the following reaction without further purification but if desired, can be purified by conventional means such as chromatography or recrystallization.

In the process ②, the desired compound can be prepared by reacting with an esterifying agent, preferably isobutene, in an inert solvent in the presence of an acid.

Examples of the solvents used include: aliphatic hydrocarbons such as hexane, heptane, ligroin or petroleum ether; aromatic hydrocarbons such as benzene, toluene or xylene; halogenated hydrocarbons such as dichloromethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; amides such as formamide, dimethylformamide, dimethylacetamide or hexamethylphosphoramide; and sulfoxides such as dimethyl sulfoxide or sulfolane; preferably ethers (particularly dioxane).

There is no particular limitation upon the nature of the acid catalyst used, provided that it can be used as an acid catalyst in conventional reactions. Preferred examples of such acid catalysts include: Bronsted acids including inorganic acids such as hydrochloric acid, hydrobromic acid, sulfuric acid, perchloric acid or phosphoric acid; and organic acids such as acetic acid, formic acid, oxalic acid, methanesulfonic acid, p-toluenesulfonic acid, trifluoroacetic acid or trifluoromethanesulfonic acid; or Lewis acids such as zinc chloride, tin tetrachloride, boron trichloride, boron trifluoride or boron tribromide, preferably inorganic acids; and more preferably strong inorganic acids (particularly hydrochloric acid).

The reaction is usually carried out at a temperature of 0° to 50° C., preferably 0° to 25° C.

The time required for the reaction depends upon the reaction temperature and other factors, such as the nature of the starting material and of the solvent, but the reaction is usually complete within a period of 1 to 48 hours, preferably 1 to 24 hours.

After completion of the reaction, the desired compound can be isolated from the reaction mixture, for example, by distilling off the solvent; pouring the reaction mixture into water; extracting it with a water-immiscible solvent such as benzene, ether or ethyl acetate; and distilling off the solvent from the extract. The product thus obtained can usually be used in the following reaction without further purification but if desired, can be purified by conventional means such as chromatography or recrystallization.

(Step 3)

In this step, a compound (6) can be prepared ① by reacting a activated derivative (that is, an acid halide or acid anhydride) of a malonic acid (5) with the corresponding alcohol, $B^2OH$, (particularly methanol or ethanol) in the presence of a base or ② by reacting a malonic acid (5) with the corresponding alcohol, $B^2OH$, in the presence of a condensing agent.

In the process ①, there is no particular limitation upon the nature of the solvent used, provided that it has no adverse effect upon the reaction and can dissolve the starting material in some extent. Examples of such solvents include: aliphatic hydrocarbons such as hexane, heptane, ligroin or petroleum ether; aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; amides such as formamide, dimethylformamide, dimethylacetamide or hexamethylphosphoramide; and sulfoxides such as dimethyl sulfoxide or sulfolane; preferably alcohols, aromatic hydrocarbons or halogenated hydrocarbons.

As a halide moiety of the acid halide used there come into consideration chlorine, bromine and iodine, preferably chlorine or bromine.

The nature of the base used in the reaction is not particularly critical, provided that it can be used as a base in conventional reactions. Examples of such bases include: inorganic base salts including alkali metal carbonates such as sodium carbonate, potassium carbonate or lithium carbonate; alkali metal hydrogencarbonates such as sodium hydrogencarbonate, potassium hydrogencarbonate or lithium hydrogencarbonate; alkali metal hydrides such as lithium hydride, sodium hydride or potassium hydride; and alkali metal hydroxides such as sodium hydroxide, potassium hydroxide, barium hydroxide or lithium hydroxide; or organic bases such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene (DBN), 1.4-diazabicyclo[2,2,2]octane (DABCO) or 1,8-diazabicyclo-[5,4,0]undec:7-ene (DBU); preferably alkali metal hydroxides or organic bases.

The reaction is usually carried out at a temperature of 0° to 60° C., preferably 0° to 30° C.

The time required for the reaction depends upon the reaction temperature and other factors, such as the nature of the starting material and of the solvent, but the reaction is usually complete within a period of 1 to 24 hours, preferably 1 to 6 hours.

After completion of the reaction, the desired compound can be isolated from the reaction mixture, for example, by distilling off the solvent; pouring the reaction mixture into water; acidifying with an inorganic acid such as hydrochloric acid or sulfuric acid; extracting it with a water-immiscible solvent such as benzene, ether or ethyl acetate; and distilling off the solvent from the extract. The product thus obtained can be used in the following reaction without further purification but, if desired, can be purified by conventional means such as chromatography or recrystallization.

In the process ②, the nature of the solvent used is not particularly critical, providing that it has no adverse effect upon the reaction and can dissolve the starting material to some extent. Examples of such solvents include: aliphatic hydrocarbons such as hexane, heptane, ligroin or petroleum ether; aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; and amides such as formamide, dimethylformamide, dimethylacetamide or hexamethylphosphoramide; preferably halogenated hydrocarbons (particularly dichloromethane), ethers (particularly tetrahydrofuran) or aromatic hydrocarbons (particularly benzene).

Preferred examples of the condensing agents used include: DCC (dicyclohexylcarbodiimide), CDI (N,N'-carbonyldiimidaole), DPPA (diphenylphosphoryl azide), HOBT (1-hydroxybenzotriazole), HONB (N-hydroxy-5-norbornene-2,3-dicarboximide) and EDAPC [1-ethyl-3-(3-dimethylaminopropyl)carbodiimide].

In the case where a condensing agent is used, the reaction is more efficiently effected by carrying it out in combination with a deacidifying agent.

Preferred examples of the deacidifying agent used include: organic amines, such as pyridine, dimethylaminopyridine or pyrrolidinopyridine. In the case where the said condensing agent is used, the reaction is accelerated by using these amines.

The reaction is usually carried out at a temperature of 0° to 60° C., preferably 0° to 30° C.

The time required for the reaction depends upon the reaction temperature and other factors, such as the nature of the starting material and of the solvent, but the reaction is usually complete within a period of 1 to 48 hours, preferably 1 to 12 hours.

After completion of the reaction, the desired compound can be isolated from the reaction mixture, separated and purified by various means in a proper combination. An example of one such technique comprises: pouring the reaction mixture into water; adding a water-immiscible solvent such as benzene, ether or ethyl acetate; filtering off insoluble materials, if any; separating an organic solvent layer; washing the extract with diluted hydrochloric acid or an aqueous solution of sodium hydrogencarbonate; and finally distilling off the solvent. The desired product thus obtained, if necessary, can be purified by conventional means, such as adsorption or ion exchange chromatography through various carriers, such as activated charcoal or silica gel; gel filtration through sephadex; or recrystallization from an organic solvent such as ether, ethyl acetate or chloroform. (Step 4)

In this step, a compound (7) can be prepared by reacting a compound (6) with an alkyl halide $R^2X$ (wherein X signifies a halogen atom, preferably chlorine or bromine), in an inert solvent in the presence of base.

There is no particular limitation upon the nature of the solvent used, provided that it has no adverse effect upon the reaction and can dissolve the starting material in some extent. Examples of such solvents include: aliphatic hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, n-propanol, isopropanol, n-butanol, isobutanol, tert-butanol, isoamyl alcohol, diethylene glycol, glycerin, octanol, cyclohexanol or methyl cellosolve; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoramide; and sulfoxides, such as dimethyl sulfoxide or sulfolane; preferably ethers (particularly diethyl ether or tetrahydrofuran), amides (particularly dimethylformamide).

The nature of the base used is not particularly critical, provided that it can be used as a base in conventional reactions. Examples of the bases include: inorganic base salts, including alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydrides, such as lithium hydride, sodium hydride or potassium hydride; alkali metal alkoxides; such as sodium methoxide, sodium ethoxide or potassium butoxide; and alkali metal hydroxides, such as sodium hydroxide, potassium hydroxide, barium hydroxide or lithium hydroxide; or organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene (DBN), 1.4-diazabicyclo[2,2,2]octane (DABCO) or 1,8-diazabicyclo[5,4,0]undec-7-ene (DBU); preferably alkali metal hydroxides, alkali metal alkoxides or organic bases.

As a halide moiety of the alkyl halide used there come into consideration chlorine, bromine and iodine, preferably chlorine or bromine.

The reaction is usually carried out at a temperature of -20° to 100° C., preferably -10° to 50° C.

The time required for the reaction depends upon the reaction temperature and other factors, such as the nature of the starting material and of the solvent, but the reaction is usually complete within a period of 1 to 48 hours, preferably 1 to 15 hours.

After completion of the reaction, the desired compound can be isolated from the reaction mixture, separated and purified by various means in a proper combination. An example of one such technique comprises: pouring the reaction mixture into water; adding a water-immiscible solvent, such as benzene, ether or ethyl acetate; filtering off insoluble materials, if any; separating an organic solvent layer; washing the extract with diluted hydrochloric acid or an aqueous solution of sodium hydrogencarbonate; and finally distilling off the solvent. The desired product thus obtained, if necessary, can be purified by conventional means, such as adsorption or ion exchange chromatography through various carriers, such as activated charcoal or silica gel; gel filtration through sephadex; or recrystallization from an organic solvent, such as ether, ethyl acetate or chloroform.

(Step 5)

In this step, a compound (8) can be prepared by subjecting a compound (7) to a hydrolysis reaction with a base in an inert solvent, followed by decarboxylation.

Examples of the solvents used hydrocarbons, such hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; alcohols, such as methanol, ethanol, n-propanol, isopropanol, n-butanol, isobutanol, tert-butanol, isoamyl alcohol, diethylene glycol, glycerin, octanol, cyclohexanol or methyl cellosolve; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoramide; sulfoxides, such as dimethyl sulfoxide or sulfolane; and a mixture of water and one or more of these organic solvents; preferably a mixture of alcohols and water.

The nature of the base used is not particularly critical, provided that it can be used as a base in conventional reactions. Examples of the bases used include: inorganic base salts, including alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydrides, such as lithium hydride, sodium hydride or potassium hydride; and alkali metal hydroxides, such as sodium hydroxide, potassium hydroxide, barium hydroxide or lithium hydroxide; or organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene (DBN), 1,4-diazabicyclo[2,2,2]octane (DABCO) or 1,8-diazabicyclo[5,4,0]undec-7-ene (DBU); preferably alkali metal hydroxides or organic bases.

The reaction is usually carried out at a temperature of 0° to 120° C., preferably 20° to 120° C.

The time required for the reaction depends upon the reaction temperature and other factors, such as the nature of the starting material and of the solvent, but the reaction is usually complete within a period of 1 to 48 hours, preferably 1 to 16 hours.

In this step, the hydrolysis of a malonate derivative is generally accompanied by decarboxylation. However, where only the hydrolysis proceeds and decarboxylation is incomplete, the reaction can be accomplished by adding an organic base, such as collidine or lutidine, followed by heating at 100° to 120° C.

After completion of the reaction, the desired compound can be isolated from the reaction mixture, separated and purified by various means in a proper combination. An example of one such technique comprises: pouring the reaction mixture into water; acidifying with hydrochloric acid etc.; adding a water-immiscible solvent, such as benzene, ether or ethyl acetate; filtering off insoluble materials, if any; separating an organic solvent layer; washing the extract with diluted hydrochloric acid; and, finally, distilling off the solvent. The desired product thus obtained, if necessary, can be purified by conventional means, such as: adsorption or ion exchange chromatography through various carriers, such as activated charcoal or silica gel; gel filtration through a sephadex column; or recrystallization from an organic solvent, such as ether, ethyl acetate or chloroform.

(Step 6)

In this step, a compound (9) can be prepared from a compound (8), which is prepared in Step 5 or which is commercially available, and the reaction is conducted in a similar manner to that of Step 3.

(Step 7)

In this step, a compound (10) can be prepared by reacting an acid halide, which is prepared by reacting a compound (8) with a reagent for the halogenation of a carboxylic acid, with an optically active oxazolidinone ZH in an inert solvent in the presence of n-butyllithium.

The nature of the solvent used in the halogenation is not critical, providing that it has no adverse effect upon the reaction and can dissolve the starting material in some extent. Examples of preferred solvents include: aliphatic hydrocarbons, such as hexane, heptane, ligroin or petroleum ether; aromatic hydrocarbons, such as benzene, toluene or xylene; and halogenated hydrocarbons, such as dichloromethane, chloroform, carbon tetrachloride, dichloroethane, chlorobenzene or dichlorobenzene.

Examples of the reagents used for halogenation include: thionyl halides, such as thionyl chloride or thionyl bromide; and phosphorus compounds, such as phosphorus trichloride, phosphorus tribromide, phosphorus pentachloride or phosphorus oxychloride.

The reaction is usually carried out at a temperature of 0° to 50° C.

The time required for the reaction depends upon the reaction temperature and other factors, such as the nature of the starting material and of the solvent, but the reaction is usually complete within a period of 0.2 to 5 hours, preferably 0.2 to 1 hour.

After completion of the reaction, the desired compound can be isolated from the reaction mixture by distilling off the solvent. The product thus obtained can be used in the following reaction without further purification.

The nature of the solvent used in the reaction with a 2-oxazolidinone derivative is not particularly critical, providing that it has no adverse effect upon the reaction and can dissolve the starting material in some extent. Examples of particularly preferred solvents include: ethers, such as diethyl ether, diisopropyl ether, tetrahydrofuran, dioxane, dimethoxyethane or diethylene glycol dimethyl ether.

Examples of optically active 2-oxazolidinone derivatives include: (4S)-isopropyl-2-oxazolidinone, (4R)-isopropyl-2-oxazolidinone, (4S)-benzyl-2-oxazolidinone and (4R)-benzyl-2-oxazolidinone.

The reaction is usually carried out at a temperature of −78° to 20° C.

The time required for the reaction depends upon the reaction temperature and other factors, such as the nature of the starting material and of the solvent, but the reaction is usually complete within a period of 0.2 to 5 hours, preferably 0.2 to 2 hours.

After completion of the reaction, the desired compound can be isolated from the reaction mixture, for example: by distilling off the solvent; pouring the reaction mixture into water; acidifying with an inorganic acid, such as hydrochloric acid or sulfuric acid; extracting with a water-immiscible solvent, such as benzene, ether or ethyl acetate; and distilling off the solvent from the extract. The product thus obtained can usually be used in the following reaction without further purification but, if desired, can be purified by conventional means, such as chromatography or recrystallization.

(Step 8)

In this step, a compound (11) can be prepared by reacting a compound (9) with a tri(substituted) silyl halide, $B^3X$ (wherein X is as defined above), in an inert solvent in the presence of a base.

There is no particular limitation upon the nature of the solvent used, provided that it has no adverse effect upon the reaction and can dissolve the starting material in some extent. Examples of such solvents include: aliphatic hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; and nitriles, such as acetonitrile or isobutyronitrile.

The nature of the base used is not particularly critical, provided that it can be used as a base in conventional reactions. Examples of preferred bases include: alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydrides, such as lithium hydride, sodium hydride or potassium hydride; organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene (DBN), 1,4-diazabicyclo[2,2,2]octane (DABCO) or 1,8-diazabicyclo[5,4,0]undec-7-ene (DBU); and organic metal bases, such as butyllithium or lithium diisopropylamide.

Examples of the trialkylsilyl halides used include: trimethylsilyl chloride or tert-butyldimethylsilyl chloride, preferably trimethylsilyl chloride.

The reaction is usually carried out at a temperature of −78° to 20° C.

The time required for the reaction depends upon the reaction temperature and other factors, such as the nature of the starting material and of the solvent, but the reaction is usually complete within a period of 1 to 10 hours.

After completion of the reaction, the desired compound can be recovered from the reaction mixture, for example: by distilling off the solvent; pouring the reaction mixture into water; acidifying with an inorganic acid, such as hydrochloric acid or sulfuric aicd; extracting with a water-immiscible solvent, such as benzene, ether or ethyl acetate; and distilling off the solvent from the extract. The product thus obtained can usually be used in the following reaction without further purification but, if desired, can be purified by conventional means, such as chromatography or recrystallization.

(Step 9)

In this step, a compound (12) can be prepared by reacting a compound (10) with an α-haloacetate $XCH_2\text{-}COOB^4$ (wherein X is as defined above), in an inert solvent in the presence of a base.

There is no particular limitation upon the nature of the solvent used, provided that it has no adverse effect upon the reaction and can dissolve the starting material in some extent. Examples of preferred solvents include: aliphatic hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; alcohols, such as methanol, ethanol, n-propanol, isopropanol, n-butanol, isobutanol, tert-butanol, isoamyl alcohol, diethylene glycol, glycerin, octanol, cyclohexanol or methyl cellosolve; amides, such as formamide, dimethylformamide, dimethylacetamide or hexamethylphosphoramide; and sulfoxides, such as dimethyl sulfoxide or sulfolane; preferably ethers.

The nature of the base used is not particularly critical, provided that it can be used as a base in conventional reactions. Preferred examples of preferred bases include: alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydrides, such as lithium hydride, sodium hydride or potassium hydride; alkali metal alkoxides, such as sodium methoxide, sodium ethoxide, potassium tert-butoxide or lithium methoxide; alkali metal mercaptides, such as sodium methylmercaptide or sodium ethylmercaptide; organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene (DBN), 1,4-diazabicyclo[2,2,2]octane (DABCO) or 1,8-diazabicyclo[5,4,0]undec-7-ene (DBU); and organic metal bases, such as butyllithium or lithium diisopropylamide; preferably lithium diisopropylamide (in tetrahydrofuran).

As a halo moiety of the α-haloacetate used there come into consideration chlorine, bromine and iodine.

As an ester moiety of the α-haloacetate used there come into consideration methyl, ethyl, benzyl and tert-butyl.

The reaction is usually carried out at a temperature of −78° to 10° C.

The time required for the reaction depends upon the reaction temperature and other factors, such as the nature of the starting material and of the solvent, but the reaction is usually complete within a period of 1 to 10 hours.

After completion of the reaction, the desired compound can be isolated from the reaction mixture, for example: by distilling off the solvent; pouring the reaction mixture into water; acidifying with an inorganic acid, such as hydrochloric acid or sulfuric acid; extracting with a water-immiscible solvent, such as benzene, ether or ethyl acetate; and distilling off the solvent from the extract. The product thus obtained can usually be used in the following reaction without further purification but, if desired, can be purified by conventional means, such as chromatography or recrystallization.

(Step 10)

In this step, a compound (13) can be prepared by hydrolysis of a compound (12) in an inert solvent in the presence of a base to remove an optically active 2-oxazolidinone derivative.

There is no particular limitation upon the nature of the solvent used, provided that it has no adverse effect upon the reaction and can dissolve the starting material in some extent. Examples of preferred solvents include: aliphatic hydrocarbons, such as hexane, heptane, ligroin or petroleum ether; aromatic hydrocarbons, such as benzene, toluene or xylene; ethers, such as diethyl ether, diisopropyl ether, tetrahydrofuran, dioxane, dimethoxyethane, diethylene glycol or diethylene glycol dimethyl ether; alcohols, such as methanol, ethanol, n-propanol, isopropanol, n-butanol, isobutanol, tert-butanol, isoamyl alcohol, diethylene glycol, glycerin, octanol, cyclohexanol or methyl cellosolve; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide, dimethylacetamide or hexamethylphosphoramide; and sulfoxides, such as dimethyl sulfoxide or sulfolane.

The nature of the base used is not particularly critical, provided that it can be used as a base in conventional reactions. Examples of preferred bases include: alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydrides, such as lithium hydride, sodium hydride or potassium hydride; alkali metal hydroxides, such as sodium hydroxide, potassium hydroxide, barium hydroxide or lithium hydroxide; alkali metal alkoxides, such as sodium methoxide, sodium ethoxide, potassium tert-butoxide or lithium methoxide; alkali metal mercaptides, such as sodium methylmercaptide or sodium ethylmercaptide; and organic bases, such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4,3,0]non-5-ene (DBN), 1,4-diazabicyclo[2,2,2]octane (DABCO) or 1,8-diazabicyclo[5,4,0]undec-7-ene (DBU).

In this step, it is most preferable that the reaction is conducted using lithium hydroxide in a mixture of tetrahydrofuran and water in the presence of hydrogen peroxide.

The reaction is usually carried out at a temperature of 0° to 100° C.

The time required for the reaction depends upon the reaction temperature and other factors, such as the nature of the starting material and of the solvent, but the reaction is usually complete within a period of 1 to 24 hours.

After completion of the reaction, the desired compound can be isolated from the reaction mixture, for example: by distilling off the solvent; pouring the reaction mixture into water; acidifying with an inorganic acid, such as hydrochloric acid or sulfuric acid; extracting with a water-immiscible solvent, such as benzene, ether or ethyl acetate; and distilling off the solvent from the extract. The product thus obtained can usually be used in the following reaction without further purification but, if desired, can be purified by conventional means, such as chromatography or recrystallization.

(Step 11)

In this step, a compound (14) can be prepared by reacting a compound (11) with an α-halocarboxylate $XCH_2$-$COOB^4$ (wherein X is as defined above), in an inert solvent.

There is no particular limitation upon the nature of the solvent used, provided that it has no adverse effect upon the reaction and can dissolve the starting material in some extent. Examples of preferred solvents include: aliphatic hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; nitriles, such as acetonitrile or isobutyronitrile; amides, such as formamide, dimethylformamide, dimethylacetamide or hexamethylphosphoramide; and sulfoxides, such as dimethyl sulfoxide or sulfolane.

As a halo moiety of the α-halocarboxylate used in the reaction there come into consideration chlorine, bromine and iodine, preferably chlorine or bromine. As an ester moiety of the α-halocarboxylate used in the reaction there come into consideration methyl, ethyl, tert-butyl and benzyl.

The reaction is usually carried out at a temperature of −78° to 30° C. The time required for the reaction depends upon the reaction temperature and other factors, such as the nature of the starting material and of the solvent, but the reaction is usually complete within a period of 0.5 to 10 hours.

After completion of the reaction, the desired compound can be isolated from the reaction mixture, for example: by distilling off the solvent; pouring the reaction mixture into water; acidifying with an inorganic acid, such as hydrochloric acid or sulfuric acid; extracting with a water-immiscible solvent, such as benzene, ether or ethyl acetate; and distilling off the solvent from the extract. The product thus obtained can usually be used in the following reaction without further purification but if desired, can be purified by conventional means, such as chromatography or recrystallization.

(Step 12)

In this step, a compound (13) can be prepared by hydrolyzing a compound (14) in an inert solvent in the presence of a base.

There is no particular limitation upon the nature of the solvent used, provided that it has no adverse effect upon the reaction and can dissolve the starting material in some extent. Examples of preferred solvents include: aliphatic hydrocarbons, such as hexane, heptane, ligroin or petroleum ether; aromatic hydrocarbons, such as benzene, toluene or xylene; ethers, such as diethyl ether, diisopropyl ether, tetrahydrofuran, dioxane, dimethoxyethane or diethylene glycol dimethyl ether; alcohols, such as methanol, ethanol, n-propanol, isopropanol, n-butanol, isobutanol, tert-butanol, isoamyl alcohol, diethylene glycol, glycerin, octanol, cyclohexanol or methyl cellosolve; ketones, such as acetone, methyl ethyl ketone, methyl isobutyl ketone, isophorone or cyclohexanone; nitriles, such as acetonitrile or isobutyronitrile; amides, such as formamide, dimethylformamide, dimethylacetamide or hexamethylphosphoramide; and sulfoxides, such as dimethyl sulfoxide or sulfolane.

The nature of the base used in the reaction is not particularly critical, provided that it can be used as a base in conventional reactions. Examples of preferred bases include: alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydrides, such as lithium hydride, sodium hydride or potassium hydride; alkali metal hydroxides, such as sodium hydroxide, potassium hydroxide, barium hydroxide or lithium hydroxide; alkali metal alkoxides, such as sodium methoxide, sodium ethoxide, potassium tert-butoxide or lithium methoxide.

The reaction is usually carried out at a temperature of 0° to 100° C.

The time required for the reaction depends upon the reaction temperature and other factors, such as the nature of the starting material and of the solvent, but the reaction is usually complete within a period of 1 to 24 hours.

After completion of the reaction, the desired compound can be isolated from the reaction mixture, for example: by distilling off the solvent; pouring the reaction mixture into water; acidifying with an inorganic acid, such as hydrochloric acid or sulfuric acid; extracting with a water-immiscible solvent, such as benzene, ether or ethyl acetate; and distilling off the solvent from the extract. The product thus obtained can usually be used in the following reaction without further purification but if desired, can be purified by conventional means, such as chromatography or recrystallization.

If desired, a protecting group, $B^4$, of a compound (13) can be replaced by another protecting group. This exchange reaction is conducted by conventional transesterification or, after protecting a free carboxylic acid group in the molecule, the protecting group, $B^4$, is eliminated according to the procedure described in Step 20, followed by introducing the desired protecting group and then reproducing a carboxylic acid group.
(Step 13)

In this step, a compound (18) can be prepared by reacting a compound (15), which is obtained by protecting an amino group of a commercially available α-amino acid by conventional means, with an alcohol, $R^8OH$, in an inert solvent in the presence of a condensing agent. The reaction is carried out in a manner similar to that of Step 2.
(Step 14)

In this step, a compound (16) can be prepared by reacting a compound (15) with an amine, $R^9R^{10}NH$, in an inert solvent in the presence of a condensing agent.

There is no particular limitation upon the nature of the solvent used, provided that it has no adverse effect upon the reaction and can dissolve the starting material in some extent. Examples of preferred solvents include: aliphatic hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitro compound, such as nitroethane or nitrobenzene; nitriles, such as acetonitrile or isobutyronitrile; amides, such as formamide, dimethylformamide, dimethylacetamide or hexamethylphosphoramide; and sulfoxides, such as dimethyl sulfoxide or sulfolane.

Examples of suitable condensing agents include: di(lower alkyl) azodicarboxylate-triphenylphosphines such as diethyl azodicarboxylate-triphenylphosphine; N-(lower alkyl)-5-arylisoxazolium-3'-sulfonates, such as N-ethyl-5-phenylisoxazolium-3'-sulfonate; N,N'-dicycloalkylcarbodiimides, such as N,N'-dicyclohexylcarbodiimide (DCC); diheteroaryl diselenides, such as 2,2'-dipyridyl diselenide; phosphins, such as diethylphosphoryl cyanide (DEPC); arylsulfonyl triazolides, such as p-nitrobenzenesulfonyl triazolide; 2-halo-1-(lower alkyl) pyridinium halides, such as 2-chloro-1-methylpyridinium iodide; diarylphosphoryl azides, such as diphenylphosphoryl azide (DPPA); imidazole derivatives, such as N,N'-carbodiimidazole (CDI); benzotriazole derivatives, such as 1-hydroxybenzotriazole (HOBT); dicarboximide derivatives, such as N-hydroxy-5-norbornene-2,3-dicarboximide (HONB), and carbodiimide derivatives, such as 1-ethyl-3-(3-dimethylaminopropyl)carbodiimide (EDAPC); preferably diarylphosphoryl azide.

The reaction is usually carried out at a temperature of 0° to 150° C., preferably 20° to 100° C.

The time required for the reaction depends upon the reaction temperature and other factors, such as the nature of the starting material and of the solvent, but the reaction is usually complete within a period of 1 to 100 hours, preferably 2 to 24 hours.

After completion of the reaction, the desired compound can be isolated from the reaction mixture, for example: by neutralizing the reaction mixture properly; filtering off insoluble materials, if any; adding water and a water-immiscible organic solvent, such as ethyl acetate, separating an organic layer; washing the extract with water; and distilling off the solvent from the extract after drying over a drying agent, such as anhydrous magnesium sulfate.
(Step 15)

In this step, a compound (17) can be prepared by reacting a compound (16) with a reagent for the deprotection of an amino-protecting group in an inert solvent.

The procedure used for the deprotection depends upon the nature of the amino-protecting group but the reaction is carried out as follows.

Where an amino-protecting group is a silyl group, it can be eliminated by treating with a compound capable of forming a fluorine anion, such as tetrabutylammonium fluoride.

The reaction temperature and the time required for the reaction are not particularly critical, but the reaction is usually conducted at ambient temperature for a period of 10 to 18 hours.

Where an amino-protecting group is an alkoxycarbonyl group or a substituted methylene group capable of forming a Schiff's base, it can be eliminated by treating with an acid in a water soluble solvent.

There is no particular limitation upon the nature of the acid used, provided that it can usually be used as an acid in conventional reactions and has no adverse effect upon the reaction. Examples of preferred acids include inorganic acids, such as hydrochloric acid, sulfuric acid, phosphoric acid or hydrobromic acid.

There is no particular limitation upon the nature of the solvent used, provided that it can be used in conventional hydrolysis. Examples of preferred solvents include: water; organic solvents including alcohols, such as methanol, ethanol or n-propanol; and ethers, such as tetrahydrofuran or dioxane; or a mixture of water and one or more these organic solvents.

The reaction temperature and the time required for the reaction vary depending upon the nature of the starting material and of the solvent as well as the nature of the acid or base used. Although there is no particular limitation, the reaction is usually carried out at a temperature of 0° to 150° C. for a period of 1 to 10 hours in order to suppress side reactions.

Where an amino-protecting group is an aralkyl or aralkyloxycarbonyl group, it can preferably be removed by contacting with a reducing agent (preferably catalytic reduction at ambient temperature in the presence of a catalyst) or with an oxidizing agent in a solvent.

In the case of deprotection by catalytic reduction, there is no particular limitation upon the nature of the solvent used, provided that it has no adverse effect upon the reaction. Examples of preferred solvents include: alcohols, such as methanol, ethanol or isopropanol; ethers, such as diethyl ether, tetrahydrofuran or dioxane; aromatic hydrocarbons, such as benzene, toluene or xylene; aliphatic hydrocarbons, such as hexane or cyclohexane; esters, such as ethyl acetate or propyl acetate; fatty acids, such as acetic acid; and a mixture of one or more of these organic solvents and water.

There is no particular limitation upon the nature of the catalyst used, provided that it can be used as a catalyst in conventional catalytic reductions. Examples of preferred catalysts include: palladium on charcoal, Raney nickel, platinum oxide, platinum black, rhodium on alumina, triphenylphosphine-rhodium chloride and palladium on barium sulfate.

There is no particular limitation upon the pressure used and the reaction is usually carried out at a pressure of 1 to 10 atmospheric pressures.

The reaction temperature and the time required for the reaction vary depending upon the nature of the starting material and of the solvent but the reaction is usually carried out at a temperature of 0° to 100° C. for a period of 5 minutes to 24 hours.

In the case of deprotection by oxidation, the solvent used is not particularly critical, provided that it has no adverse effect upon the reaction. A preferred solvent is an aqueous organic solvent.

Preferred examples of such solvents include: ketones, such as acetone; halogenated hydrocarbons, such as dichloromethane, chloroform or carbon tetrachloride; nitriles, such as acetonitrile; ethers, such as diethyl ether, tetrahydrofuran or dioxane; amides, such as dimethylformamide, dimethylacetamide or hexamethylphosphoramide; and sulfoxides, such as dimethyl sulfoxide.

There is no particular limitation upon the nature of the oxidizing agent used, provided that it can be used in conventional oxidation. Examples of preferred oxidizing agents include: potassium persulfate, sodium persulfate, ammonium cerium nitrate (CAN) and 2,3-dichloro-5,6-dicyano-p-benzoquinone (DDQ).

Although the reaction temperature and the time required for the reaction vary depending upon the nature of the starting material and of the solvent as well as the type of the catalyst used, the reaction is usually conducted at a temperature of 0° to 150° C. for a period of 10 minutes to 24 hours.

Where an amino-protecting group is an alkenyloxycarbonyl group, it can usually be removed by treating with a base in a similar manner as where an amino-protecting group is the said aliphatic acyl, aromatic aryl or alkoxycarbonyl group, or a substituted methylene group capable of forming a Schiff's base.

Where an amino-protecting group is an aryloxycarbonyl group, it can simply be eliminated by using palladium, triphenylphosphine or nickel tetracarbonyl and the side reactions are suppressed.

The reaction temperature depends upon the nature of the starting material and of the solvent as well as the type of the reagent to be used, but the reaction is usually carried out at a temperature of 0° to 150° C., preferably 20° to 100° C.

The time required for the reaction depends upon the reaction temperature and other factors, such as the nature of the starting material and of the solvent, but the reaction is usually complete within a period of 1 to 100 hours, preferably 2 to 24 hours.

After completion of the reaction, the desired compound is isolated from the reaction mixture, for example: by neutralizing the reaction mixture properly; filtering off insoluble materials, if any; adding water and a water-immiscible organic solvent, such as ethyl acetate; separating the organic layer; washing the extract with water; drying over a drying agent, such as anhydrous magnesium sulfate; and distilling off the solvent. The desired product thus obtained can be purified, if necessary, by conventional means, such as recrystallization, reprecipitation or chromatography.

(Step 16)

In this step, a compound (19) is prepared by reacting a compound (18) with a reagent for the deprotection of an amino-protecting group in an inert solvent, and the reaction is conducted in a manner similar to that of Step 15.

(Step 17)

In this step, a compound (20) can be prepared by reacting a compound (16) (provided that either of $R^9$ or $R^{10}$ is a methoxy group when the other group is methyl) with a reagent $R^7M$ [wherein M signifies alkali metals, such as lithium, or a Grignard reagent (MgBr or MgCl)] in an inert solvent.

There is no particular limitation upon the nature of the solvent used, provided that it has no adverse effect upon the reaction and can dissolve the starting material in some extent. Examples of such solvents include: aliphatic hydrocarbons, such as hexane, heptane, ligroin or petroleum ether; aromatic hydrocarbons, such as benzene, toluene or xylene; halogenated hydrocarbons, such as dichloromethane, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether.

The reaction temperature depends upon the nature of the starting material and of the solvent as well as the type of the reagent used, but the reaction is usually carried out at a temperature of −70° to 50° C., preferably −40° to 30° C.

The time required for the reaction depends upon the reaction temperature and other factors, such as the nature of the starting material and of the solvent, but the reaction is complete within a period of 5 minutes to 24 hours, preferably 30 minutes to 3 hours.

After completion of the reaction, the desired compound is isolated from the reaction mixture, for example: by neutralizing the reaction mixture properly; filtering off insoluble materials, if any; adding water and a water-immiscible organic solvent, such as ethyl acetate; separating the organic layer; washing the extract with water; drying over a drying agent, such as anhydrous magnesium sulfate; and distilling off the solvent.

The desired product thus obtained can be purified, if necessary, by conventional means, such as recrystallization, reprecipitation or chromatography.

(Step 18)

In this step, a compound (21) can be prepared by reacting a compound (20) with a reagent for the deprotection of an amino-protecting group in an inert solvent, and the reaction is conducted in a manner similar to that of Step 15.

(Step 19)

In this step, a compound (22) can be prepared by reacting a compound (4) with a compound (13) in an inert solvent in the presence of a condensing agent, and the reaction is conducted in a manner similar to that of Step 14.

(Step 20)

In this step, a compound (23) can be prepared by removing a protecting group, $B^4$, of a compound (22) in an inert solvent.

Deprotecting procedures depend upon the nature of the protecting group used, but can be conducted according to a method well-known in this art field.

Where a carboxyl-protecting group is a tert-butyl or benzhydryl group, it is deprotected by treating with trifluoroacetic acid, hydrobromic acid in acetic acid or hydrochloric acid in dioxane.

Where a carboxyl-protecting group is a trichloroethyl or trichlorobromo group, it is deprotected by reacting with zinc powder in a mixture of acetic acid or a phosphate buffer solution (pH=4.27–7.2) and ethers, such as tetrahydrofuran.

Where a carboxyl-protecting group is an aralkyl group, such as a benzyl group, it is deprotected by contacting with a reducing agent in a solvent (preferably catalytic reduction at ambient temperature in the presence of a catalyst).

(Step 21)

In this step, a compound (24) can be prepared by reacting a compound (23) with a hydroxylamine, $B^6ONH_2$, in an inert solvent and the reaction is conducted in a manner similar to that of Step 19.

(Step 22)

In this step, a compound (1A) can be prepared by removing the protecting groups, A and $B^6$ of a compound (24) in an inert solvent, with the proviso that $B^1$ has the same significance as $R^3$.

Miscellaneous methods are conducted in this step depending upon the nature of the protecting groups.

For example, in the case of a compound (24) wherein $B^6$ represents a benzyl group and A represents a benzyloxycarbonyl group, such protecting groups can be removed by catalytic reduction, which is carried out in a suitable solvent, such as alcohol, ether or acetic acid in the presence of a catalyst, such as palladium on charcoal or platinum in a stream of hydrogen. Where both A and $B^6$ represent a tert-butoxycarbonyl group, elimination of a protecting group can be accomplished under an acidic condition using trifluoroacetic acid, hydrobromic acid in acetic acid or hydrochloric acid in dioxane. In all cases, the deprotection can be accomplished under the commonly used conditions for the deprotection of an amino- or hydroxyl-protecting groups.

There is no particular limitation upon the nature of the solvent used, provided that it has no adverse effect upon the reaction and can dissolve the starting material in some extent. Examples of such solvents include: aliphatic hydrocarbons, such as hexane, heptane, ligroin or petroleum ether, aromatic hydrocarbons, such as benzene, toluene or xylene; halogenated hydrocarbons, such as dichloromethane, chloroform, carbon tetrachloride, dichloroethane, chlorobenzene or dichlorobenzene, esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; alcohols, such as methanol, ethanol, n-propanol, isopropanol, n-butanol, isobutanol, tert-butanol, isoamyl alcohol, diethylene glycol, glycerin, octanol, cyclohexanol or methyl cellosolve; ketones, such as acetone, methyl ethyl ketone, methyl isobutyl ketone, isophorone or cyclohexanone; nitro compounds, such as nitroethane or nitrobenzene; nitriles, such as acetonitrile or isobutyronitrile; amides, such as formamide, dimethylformamide or hexamethylphosphoramide; sulfoxides, such as dimethyl sulfoxide or sulfolane.

The reaction is carried out at a temperature of −20° to 100° C., preferably 0° to 40° C.

The time required for the reaction depends upon the reaction temperature and other factors, such as the nature of the starting material and of the solvent used, but the reaction is usually complete within a period of 0.5 to 48 hours, preferably 1 to 5 hours.

After completion of the reaction, the desired compound is isolated from the reaction mixture, for example: by distilling off the solvent; pouring the reaction mixture into water; acidifying with an inorganic acid, such as hydrochloric acid or sulfuric acid; extracting with a water-immiscible solvent, such as benzene, ether or ethyl acetate; and distilling off the solvent from the extract. The product thus obtained can usually be used in the following reaction without further purification but if desired, can be purified by conventional means, such as chromatography or recrystallization.

(Step 23)

In this step, a compound (25) can be prepared by eliminating a protecting group, $B^1$ of a compound (24) in an inert solvent and the reaction is conducted in a manner similar to that of Step 20.

(Step 24)

In this step, a compound (26) can be prepared by reacting a compound (25) with an alcohol, $R^3OH$, in an inert solvent in the presence of a condensing agent, and the reaction is conducted in a manner similar to that of process 2 in Step 3.

(Step 25)

In this step, a compound (27) can be prepared by reacting a compound (25) with an amine, $R^4R^5NH$, in an inert solvent in the presence of a condensing agent, and the reaction is conducted in a manner similar to that of Step 14.

(Step 26)

In this step, a compound (1B) can be prepared by removing the protecting groups, A and $B^6$ in a compound (26) in an inert solvent, and the reaction is conducted in a manner similar to that of Step 22.

(Step 27)

In this step, a compound (1C) can be prepared by removing the protecting groups, A and $B^6$ in a compound (27) in an inert solvent, and the reaction is conducted in a manner similar to that of Step 22.

(Step 28)

In this step, a compound (28) can be prepared by reacting a compound (25) with a compound (21), which is commercially available or prepared in Step 18, in an inert solvent, and the reaction is conducted in a manner similar to that of Step 25.

(Step 29)

In this step, a compound (29) can be prepared by reacting a compound (25) with a compound (19), which is commercially available or prepared in Step 16, in an inert solvent, and the reaction is conducted in a manner similar to that of Step 25.

(Step 30)

In this step, a compound (30) can be prepared by reacting a compound (25) with a compound (17), which is commercially available or prepared in Step 15, in an inert solvent, and the reaction is conducted in a manner similar to that of Step 25.

(Step 31)

In this step, a compound (1D) can be prepared by reacting a compound (28) with a reagent for deprotection in an inert solvent, and the reaction is conducted in a manner similar to that of Step 22.

(Step 32)

In this step, a compound (1E) can be prepared by reacting a compound (29) with a reagent for deprotection in an inert solvent, and the reaction is conducted in a manner similar to that of Step 22.

(Step 33)

In this step, a compound (1F) can be prepared by reacting a compound (30) with a reagent for deprotection in an inert solvent, and the reaction is conducted in a manner similar to that of Step 22.

EFFECT OF INVENTION (Test Example 1)

Inhibitory activity on type IV collagenases

The activity of type IV collagenase was assayed according to the method of Salo et al. [J. Biol. Chem., Vol. 258, 3058–3063 (1983)].

In detail, the activity was assayed by measuring the cleavage of collagen by using type IV collagenases prepared from a serum-free culture medium of human melanoma cells, and type IV collagen prepared from mouse EHS tumor radio-labelled as a substrate.

The inhibitory activity on type IV collagenases was measured by calculating the inhibition percent of the enzyme reaction, in which the test samples were added to the reaction mixture.

The results (expressed as $I_{50}$) is shown below.

TABLE 2

| Compound No. | $IC_{50}$ (nmol/ml) |
|---|---|
| Example 3 | 0.33 |
| Example 4 | 0.35 |
| Example 5 | 0.36 |
| Example 14 | 0.082 |
| Example 16 | 0.042 |
| Example 17 | 0.27 |
| Example 18 | 0.027 |
| Example 19 | 0.080 |
| Example 20 | 0.073 |
| Example 21 | 0.28 |
| Example 27 | 0.16 |
| Example 29 | 0.25 |
| Example 30 | 0.24 |
| Example 32 | 0.75 |
| Example 33 | 0.064 |
| Example 34 | 0.037 |
| Example 35 | 0.20 |
| Example 108 | 1.4 |
| Example 109 | 4.3 |
| Example 110 | 18.5 |

POSSIBLE USEFULNESS IN INDUSTRY

The compounds of the present invention have excellent inhibitory activity on type IV collagenases, and are useful as inhibitors of angiogenesis, as inhibitors of cancer invasion or as inhibitors of cancer metastasis.

When the compounds of the present invention are employed as inhibitors of angiogenesis, as inhibitors of cancer invasion or as inhibitors of cancer metastasis, these compounds may be administered in various forms. As the mode of administration, there may be mentioned for example: oral administration by tablets, capsules, powders, granules or syrups; or parenteral administration by injections (intravenous, intramuscular, subcutaneous), eye drops or suppositories. These drug forms can be prepared according to conventional means, where the main ingredient is added with any known additives usually employable in the technological field of pharmaceutical preparation, such as vehicles, binders, disintegrators, lubricants, corrigents, solubilizers, suspending agents and/or coating agents. Though the dosage may be varied depending on patient's symptom, age, body weight, administration route and preparation forms, usually the amount from 50 mg to 1000 mg can be given to one adult a day.

BEST EMBODIMENT FOR WORKING THE INVENTION

The present invention is illustrated in detail by the following Examples, Referential Examples and Preparation Examples.

EXAMPLE 1

$N^2$-[2-(R)-(Hydroxyaminocarbonyl)methyl-1-oxoheptyl]-(S)-piperazic (4S)-5-methyl-3-oxohexan-4-ylamide $N^1$-Benzyloxycarbonyl-$N^2$-[2-(R)-(benzyloxyaminocarbonyl)methyl-1-oxoheptyl]-(S)-piperazic acid (4S)-5-methyl-3-oxohexan-4-ylamide (75 mg), prepared in Referential Example 16, in methanol (3.0 ml) was catalytically reduced in the presence of 10% palladium on charcoal (8 mg) under an atmosphere of hydrogen at room temperature with stirring for 1.8 hr. After completion of the reaction, the catalyst was filtered off and the filtrate was concentrated under reduced pressure. The residue was purified by preparative thin layer chromatography through silica gel (20× 20 cm size, 0.5 mm thick), using a 10:1 mixture of chloroform and methanol as a developing solvent and a 10:1 mixture of ethyl acetate and methanol as an eluent, to give the desired compound (28 mg).

NMR spectrum (270 MHz, $CDCl_3$) δ ppm: 0.77 (3H, d, J=6.6 Hz), 0.84 (3H, t, J=7.3 Hz), 0.93 (3H, d, J=6.6 Hz), 1.09 (3H, t, J=7.3 Hz), 1.13–2.68 (15H, complex), 2.57 (2H, q, J=7.3 Hz), 2.70–3.18 (2H, complex), 3.98 (1H, br.d, J=5.9 Hz), 4.64 (1H, dd, J=8.6, 4.6 Hz), 4.85 (1H, d, J=12.5 Hz), 5.37 (1H, br.s), 7.64 (1H, d, J=8.6 Hz), 9.91 (1H, m).

IR absorption spectrum (liquid film) $cm^{-1}$: 3300 (m), 2940 (m), 1715 (m), 1660 (s), 1625 (s)

High resolution MS spectrum: $[M]^+$=426.2851 ($C_{21}H_{38}N_4O_5$); Calcd. value: 426.2842 $[\alpha]_D^{26}$=−30.60° (c=1.00, EtOH)

EXAMPLE 2

$N^2$-[2-(R)-(Hydroxyaminocarbonyl)methyl-1-oxoheptyl]-(S)-piperazic acid (4S)-6-methyl-3-oxoheptan-4-ylamide Following the procedure described in Example 1, the protecting groups of $N^1$-benzyloxycarbonyl-$N^2$-[2-(R)-(benzyloxyaminocarbonyl)methyl-1-oxoheptyl]-(S)-piperazic acid (4S)-6-methyl-3-oxoheptan-4-ylamide (24 mg), prepared in Referential Example 23, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (10 mg).

NMR spectrum (270 MHz, CDCl$_3$) δ ppm: 0.78–0.98 (9H, complex), 1.09 (3H, t, J=6.9 Hz), 1.12–2.11 (15H, complex), 2.18–2.50 (2H, m), 2.59 (2H, m), 2.70–3.12 (2H, complex), 4.00 (1H, m), 4.65 (1H, br.d, J=5.3 Hz), 4.87 (1H, br.d, J=11.9 Hz), 5.28 (1H, br.s), 7.68 (1H, br.d, J=5.3 Hz), 9.90 (1H, m)

IR absorption spectrum (liquid film) cm$^{-1}$: 3300 (m), 2945 (m), 1720 (m), 1660 (s), 1625 (s)

High resolution MS spectrum: [M+H]$^+$=441.3069 ($C_{22}H_{41}N_4O_5$); Calcd. value: 441.3077 $[\alpha]_D^{26}$=−32.5° (c=1.00, CHCl$_3$)

EXAMPLE 3

2-(S)-[N$^2$-[2-(R)-(Hydroxyaminocarbonyl)methyl-1-oxoheptyl]-(S)-piperazyl]aminoisovaleric acid N-methyl-N-methoxyamide Following the procedure described in Example 1, the protecting groups of 2-(S)-[N$^1$-benzyloxycarbonyl-N$^2$-[2-(R)-(benzyloxyaminocarbonyl)methyl-1-oxoheptyl]-(S)-piperazyl]aminoisovaleric acid N-methyl-1-N-methoxyamide (39 mg), prepared in Referential Example 24, were removed by catalytic reduction. The product was purified by preparative thin layer chromatography through silica gel (20×20 cm size, 0.5 mm thick), using a 17:1 mixture of chloroform and methanol as a developing solvent and a 10:1 mixture of ethyl acetate and nethanol as an eluent, to give the desired compound (18 mg).

NMR spectrum (270 MHz, CDCl$_3$) δ ppm: 0.69–1.06 (9H, complex), 1.10–2.44 (14H, complex), 2.57 (1H, t, J=12.5 Hz), 2.82 (1H, m), 3.00 (1H, br.d, J=12.5 Hz), 3.26 (3H, s), 3.85 (3H, s), 3.97 (1H, br.d, J=6.6 Hz), 4.95 (1H, br.t, J=7.5 Hz), 5.08 (1H, d, J=11.9 Hz), 5.47 (1H, s), 8.16 (1H, br.d, J=8.6 Hz), 10.6 (1H, m)

IR absorption spectrum (liquid film) cm$^{-1}$: 3300 (m), 2945 (m), 1630 (s)

High resolution MS spectrum: [M]$^+$=457.2868 ($C_{21}H_{39}N_5O_6$); Calcd. value: 457.2836 $[\alpha]_D^{26}$=−43.8° (c=1.01, EtOH)

EXAMPLE 4

Methyl 2-(S)-[N$^2$-[2-(R)-(Hydroxyaminocarbonyl) methyl-1-oxoheptyl]-(S)-piperazyl]aminoisovalerate Following the procedure described in Example 1, the protecting groups of methyl 2-(S)-[N$^1$-benzyloxy-carbonyl-N$^2$-[2-(R)-(benzyloxyaminocarbonyl)methyl-1-oxoheptyl]-(S)-piperazinyl]aminoisovalerate (49 mg), prepared in Referential Example 25, were removed by catalytic reduction. The product was purified by preparative thin layer chromatography through silica gel (20×10 cm size, 0.5 mm thick), using a 20:1 mixture of chloroform and methanol as a developing solvent twice and a 10:1 mixture of ethyl acetate and methanol as an eluent, to give the desired compound (20 mg).

NMR spectrum (270 MHz, CDCl$_3$) δ ppm: 0.67–1.02 (9H, complex), 1.04–2.60 (15H, complex), 2.82 (1H, m), 3.01 (1H, br.d, J=12.5 Hz), 3.77 (3H, s), 3.97 (1H, m), 4.57 (1H, dd, J=7.9 and 5.3 Hz), 4.92 (1H, d, J=11.9 Hz), 5.38 (1H, s), 7.74 (1H, br.d, J=7.3 Hz), 9.82 (1H, m)

IR absorption spectrum (liquid film) cm$^{-1}$: 3300 (m), 2940 (m), 1730 (m), 1660 (s), 1625 (s)

High resolution. MS spectrum: [M]$^+$=428.2631 ($C_{20}H_{36}N_4O_6$); Calcd. value: 428.2635 $[\alpha]_D^{26}$=−27.0° (c=1.02 EtOH)

EXAMPLE 5 tert-Butyl 2-(S)-[N$^2$-[2-(R)-Hydroxyaminocarbonyl) -methyl-1-oxoheptyl]-(S)-piperazyl) aminoisovalerate Following the procedure described in Example 1, the protecting groups of tert-butyl 2-(S)-[N$^1$-benzyloxy-carbonyl-N$^2$-[2-(R)-(benzyloxyaminocarbonyl)methyl-1-oxoheptyl]-(S)-piperazyl]aminoisovalerate (42 mg), prepared in Referential Example 26, were removed by catalytic reduction. The product was purified by preparative thin layer chromatography through silica gel (20×10 cm size, 0.5 mm thick), using a 20:1 mixture of chloroform and methanol as a developing solvent twice and a 10:1 mixture of ethyl acetate and methanol as an eluent, to give the desired compound (16 mg).

NMR spectrum (270 MHz, CDCl$_3$) δ ppm: 0.72–0.97 (9H, complex), 1.11–2.38 (14H, complex), 1.48 (9H, s), 2.49 (1H, dd, J=12.5 and 11.2 Hz), 2.83 (1H, m), 3.01 (1H, br.d, J=11.9 Hz), 3.96 (1H, m), 4.47 (1H, m), 4.89 (1H, d, J=11.2 Hz), 5.38 (1H, br.s), 7.54 (1H, br.d, J=7.9 Hz), 9.86 (1H, m)

IR absorption spectrum (liquid film) cm$^{-1}$: 3320 (m), 2945 (m), 1720 (w), 1665 (m), 1630 (s)

High resolution MS spectrum: [M]$^+$=470.3110 ($C_{23}H_{42}N_4O_6$); Calcd. value: 470.3104 $[\alpha]_D^{26}$=36.6° (c=1.00, EtOH)

EXAMPLE 6

N$^2$-[2-(R)-hydroxyaminocarbonyl)methyl-1-oxoheptyl]-(R)-piperazic acid tert-butyl ester Following the procedure described in Example 1, the protecting groups of N$^1$-benzyloxycarbonyl-N$^2$-[2-(R)-(benzyloxyaminocarbonyl)methyl-1-oxoheptyl]-(R)-piperazic acid tert-butyl ester (34 mg), prepared in Referential Example 29, were removed by catalytic reduction. The product was purified by preparative thin layer chromatography through silica gel (20×20 cm size, 0.5 mm thick), using a 20:1 mixture of chloroform and methanol as a developing solvent twice and a 10:1 mixture of ethyl acetate and methanol as an eluent, to give the desired compound (14 mg) as colorless crystals having a m.p. of 110°–111° C. after recrystallization from a mixture of hexane and ethyl acetate.

NMR spectrum (270 MHz, CDCl$_3$) δ ppm: 0.87 (3H, t, J=6.6 Hz), 1.12–2.04 (11H, complex), 1.48 (9H, s), 2.18–2.49 (3H, complex), 2.71 (1H, m), 3.07 (1H, br.d, J=13.2 Hz), 4.00 (1H, m), 4.16 (1H, d, J=12.5 Hz), 5.19 (1H, d, J=4.0 Hz), 9.03 (1H, br.s)

IR absorption spectrum (liquid film) cm$^{-1}$: 3240 (m), 2940 (s), 1725 (s), 1630 (s)

High resolution MS spectrum: [M]$^+$=371.2397 ($C_{18}H_{33}N_3O_5$); Calcd. value: 371.2419 $[\alpha]_D^{26}$ =+30.4° (c=0.50, EtOH)

EXAMPLE 7

N$^2$-(3-hydroxyaminocarbonylpropionyl)-(S)-piperazic acid tert-butyl ester

Following the procedure described in Example 1, the protecting groups of N$^1$-benzyloxycarbonyl-N$^2$-(3- benzyloxyaminocarbonylpropionyl)-(S)-piperazic acid tert-butyl ester (84 mg), prepared in Referential Example 35, were removed by catalytic reduction. After working-up in a similar manner to that of Example 1, the desired compound (36 mg) was obtained.

NMR spectrum (270 MHz, CDCl$_3$) δ ppm: 1.41 (1H, m, overlap to 6 1.48), 1.48 (9H, s), 1.61 (1H, m), 1.86 (1H, m), 2.18 (1H, br.d, J=13.2 Hz), 2.33–2.58 (2H, cpmplex), 2.66–3.12 (4H, complex), 4.28 (1H, br.d, J=12.5 Hz), 5.14 (1H, dd, J=4.6 and 1.3 Hz), 7.6–8.6 (1H, br.s), 9.59 (1H, m)

IR absorption spectrum (liquid film) cm$^{-1}$: 3250 (m), 2945 (m), 1725 (s), 1640 (s)

High resolution MS spectrum: [M]$^+$=301.1631 (C$_{13}$H$_{23}$N$_3$O$_5$); Calcd. value: 301.1636 [α]$_D^{26}$=–12.9° (c=1.01 EtOH)

EXAMPLE 8

N$^2$-(3-Hydroxyaminocarbonylpropionyl)-(S)-piperazic acid (4S,5S)-5-methyl-3-oxoheptan-4-ylamide Following the procedure described in Example 1, the protecting groups of N$^1$-benzyloxycarbonyl-N$^2$-(3-benzyloxyaminocarbonylpropionyl)-(S)-piperazic acid (4S, 5S)-5-methyl-3-oxoheptan-4-ylamide (111 mg), prepared in Referential Example 37, were removed by catalytic reduction. The product was purified by preparative reverse phase thin layer chromatography through silica gel (20×20 cm size, 0.25 mm thick, two plates), using a 1:1 mixture of water and methanol as an eluent, to give the desired compound (53 mg).

NMR spectrum (270 MHz, CDCl$_3$) δ ppm: 0.87 (3H, t, J=7.3 Hz), 0.92 (3H, d, J=6.6 Hz), 1.07 (3H, t, J=7.3 Hz), 1.28 (1H, m), 1.42–2.23 (6H, complex), 2.34–2.52 (2H, complex), 2.55 (2H, q, J=7.3 Hz), 2.75 (1H, m), 2.85–3.13 (3H, complex), 4.58 (1H, dd, J=7.9 and 5.3 Hz), 4.64 (1H, d, J=12.5 Hz), 5.27 (1H, d, J=4.6 Hz), 7.31 (1H, m), 8.12–8.83 (1H, br.s), 9.83 (1H, br.s)

IR absorption spectrum (liquid film) cm$^{-1}$: 3280 (s), 2965 (s), 1715 (s), 1635 (s)

High resolution MS spectrum: [M+H–OH]$^+$=354.2261 (C$_{17}$H$_{30}$N$_4$O$_4$); Calcd. value: 354.2266 [α]$_D^{26}$=–12.2° (c=1.97, CHCl$_3$)

EXAMPLE 9

N$^2$-[2-(R)-(hydroxyaminocarbonyl)methyl-1-oxoheptyl]-(S)-piperazic acid methyl ester To a solution of N$^1$-benzyloxycarbonyl-N$^2$-[2-(R)-benzyloxyaminocarbonyl)methyl-1-oxoheptyl]-(S)-piperazic acid (34 mg), prepared in Referential Example 13, in ethyl acetate (2.0 ml) was added an ethereal solution of diazomethane with ice-cooling, until the evolution of nitrogen gas ceased. After completion of the reaction, the solvent was distilled off under reduced pressure. The product was purified by preparative thin layer chromatography through silica gel (20×20 cm size, 0.5 mm thick), using a 30:1 mixture of chloroform and methanol as a developing solvent to give a compound (11 mg). Following the procedure described in Example 1, the protecting groups of the compound thus obtained were removed by catalytic reduction and the resulting product was purified by preparative thin layer chromatography through silica gel (20×10 cm size, 0.5 mm thick), using a 25:1 mixture of chloroform and methanol as a developing solvent and a 10:1 mixture of ethylacetate and methanol as an eluent, to give the desired compound (4.2 mg).

NMR spectrum (270 MHz, CDCl$_3$) δ ppm: 0.83 (3H, t, J=6.6 Hz), 1.10–2.01 (11H, complex), 2.22 (1H, m), 2.30 (1H, dd, J=14.2 and 3.6 Hz), 2.54 (1H, dd, J=14.2 and 11.2 Hz), 2.73–3.14 (2H, complex), 3.77 (3H, s), 3.95 (1H, m), 4.20 (1H, d, J=11.9 Hz), 5.34 (1H, d, J=4.0 Hz), 7.35–8.20 (1H, m), 9.18 (1H, m)

IR absorption spectrum (film) cm$^{-1}$: 3245 (m), 2950 (s), 1735 (s), 1630 (s)

High resolution MS spectrum: [M]$^+$=329.1965 (C$_{15}$H$_{27}$N$_3$O$_5$); Calcd. value: 329.1950 [α]$_D^{26}$–15° (c=0.35, EtOH)

EXAMPLE 10

N$^2$-[2-(R)-(oxyaminocarbonyl)methyl-1-oxoheptyl]-(S)-piperazic acid tert-butyl ester Following the procedure described in Example 1, the protecting groups of N$^1$-benzyloxycarbonyl-N$^2$-[2-(R)-benzyloxyaminocarbonyl)methyl-1-oxoheptyl]-(S)-piperazic acid tert-butyl ester (127 mg), prepared in Referential Example 12, were removed by catalytic reduction. After working up in a manner similar to that of Example 1, the desired compound (63 mg) was obtained.

NMR spectrum (270 MHz, CDCl$_3$) δ ppm: 0.86 (3H, t, J=6.6 Hz), 1.11–1.70 (10H, complex), 1.48 (9H, s), 1.89 (1H, m), 2.03–2.38 (2H, complex), 2.52 (1H, m), 2.82–3.13 (2H, complex), 3.98 (1H, br.s), 4.28 (1H, br.d, J=10.6 Hz), 5.20 (1H, s)

IR absorption spectrum (liquid film) cm$^{-1}$: 3225 (m), 2940 (s), 1725 (s), 1640 (br.s)

High resolution MS spectrum: [M+H]$^+$=372.2517 (C$_{18}$H$_{34}$N$_3$O$_5$); Calcd. value: 372.2499 [α]$_D^{26}$=–10.7° (c=1.00, EtOH)

EXAMPLE 11

N$^2$-[2-(R)-(oxyaminocarbonyl)methyl-4-methyl-1-oxopentyl]-(S)-piperazic acid tert-butyl ester Following the procedure described in Example 1, the protecting groups of N$^1$-benzyloxycarbonyl-N$^2$-[2-(R)-benzyloxyaminocarbonyl)methyl-4-methyl-1-oxopentyl]-(S)-piperazic acid tert-butyl ester (20 mg), prepared in Referential Example 46, were removed by catalytic reduction. The product was worked up in a manner similar to that of Example 1 and the desired compound was obtained (11 mg).

NMR spectrum (270 MHz, CDCl$_3$) δ ppm: 0.89 (3H, d, J=6.6 Hz), 0.93 (3H, d, J=6.6 Hz), 1.10–1.70 (4H, complex), 1.48 (9H, s), 1.88 (1H, m), 2.19 (1H, br.d, J=11.6 Hz), 2.30 (1H, br.d, J=11.6 Hz), 2.50 (1H, m), 2.71–3.12 (3H, complex), 4.03 (1H, br.d, J=5.9 Hz), 4.25 (1H, d, J=11.9 Hz), 5.20 (1H, br.s), 9.39 (1H, s)

IR absorption spectrum (film) cm$^{-1}$: 3240 (s), 2960 (s), 1725 (s), 1630 (s)

High resolution MS spectrum: [M]$^+$=357.2270 (C$_{17}$H$_{31}$N$_3$O$_5$); Calcd. value: 357.2264 [α]$_D^{26}$=–12.3° (c=0.51, EtOH)

EXAMPLE 12

N$^1$-[2-(R)-(hydroxyaminocarbonyl)methyl-1-oxodecyl]-(S)-piperazic acid tert-butyl ester Following the procedure described in Example 1, the protecting groups of N$^1$-benzyloxycarbonyl-N$^2$-[2-(R)-benzyloxyaminocarbonyl)methyl-1-oxodecyl]-(S)-piperazic acid t-butyl ester (32 mg), prepared in Referential Example 58, were removed by catalytic reduction. After working up in a manner similar to that of Example 1, the desired compound (15 mg) was obtained.

NMR spectrum (270 MHz, CDCl$_3$) δ ppm: 0.87 (3H, t, J=6.6 Hz), 1.12–1.70 (16H, complex), 1.49 (9H, s), 1.88 (1H, m), 2.18 (1H, br.d, J=11.7 Hz), 2.30 (1H, br.d, J=11.7 Hz), 2.53 (1H, m), 2.75–3.36 (2H, complex), 3.93 (1H, m), 4.27 (1H, d, J=11.9 Hz), 5.20 (1H, br.s)

IR absorption spectrum (liquid film) cm$^{-1}$: 3230 (m), 2940 (s), 1725 (s), 1635 (s)

High resolution MS spectrum: [M]$^+$=413.2903 (C$_{21}$H$_{39}$N$_3$O$_5$); Calcd. value: 413.2890 [α]$_D^{26}$=−11.9° (c=1.00, EtOH)

EXAMPLE 13

N$^2$-[2-(R)-(Hydroxyaminocarbonyl)methyl-1-oxodecyl]-(S)-piperazic acid N-methylamide Following the procedure described in Example 1, the protecting groups of N$^1$-benzyloxycarbonyl-N$^2$-[2-(R)-benzyloxyaminocarbonyl)methyl-1-oxodecyl]-(S)-piperazic acid N-methylamide (14 mg), prepared in Referential Example 60, were removed by catalytic reduction. The product was purified by preparative thin layer chromatography through silica gel (20×10 cm size, 0.5 mm thick), using a 10:1 mixture of chloroform and methanol as a developing solvent twice and a 10:1 mixture of ethyl acetate and methanol as an eluent, to give the desired compound (9 mg).

NMR spectrum (270 MHz, CDCl$_3$) δ ppm: 0.88 (3H, t, J=6.6 Hz), 1.05–2.15 (18H, complex), 2.30 (1H, m), 2.53 (1H, m), 2.80 (3H, d, J=4.6 Hz), 2.83 (1H, m), 3.03 (1H, br.d, J=11.9 Hz), 3.84 (1H, m), 4.64 (1H, d, J=9.9 Hz), 5.05 (1H, br.s), 6.55 (br.s), 9.2–9.8 (1H, br.s)

IR absorption spectrum (film) cm$^-$: 3260 (s), 2930 (s), 1650 (s), 1625 (s)

High resolution MS spectrum: [M]$^+$=352.2466 (C$_{18}$H$_{32}$N$_3$O$_4$); Calcd. value: 352.2466 [α]$_D^{26}$=−3.4° (c=0.82, EtOH)

EXAMPLE 14

N$^2$-[2-(R)-(Hydroxyaminocarbonyl)methyl-1-oxooctyl]-(S)-piperazic acid N-methylamide Following the procedure described in Example 1, the protecting groups of an N-methylamide compound, which was prepared by condensing methylamine with N$^1$-benzyloxycarbonyl-N$^2$-[2-(R)-benzyloxyaminocarbonyl)methyl-1-oxooctyl]-(S)-piperazic acid (45 mg), prepared in Referential Example 70, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (10 mg).

NMR spectrum (270 MHz, CDCl$_3$) δ ppm: 0.87 (3H, t, J=6.5 Hz), 0.99–1.95 (13H, complex), 2.05 (1H, br.d, J=10.6 Hz), 2.29 (1H, dd, J=13.9 and 3.3 Hz), 2.52 (1H, br.t, J=13.9 Hz), 2.79 (3H, d, J=4.6 Hz), 2.81 (1H, overlap to 2.79 ppm), 3.02 (1H, d, J=13.2 Hz), 3.88 (1H, m), 4.67 (1H, d, J=11.9 Hz), 5.06 (1H, s), 6.75 (1H, d, J=4.6 Hz), 9.52–9.91 (1H, br.s)

IR absorption spectrum (film) cm$^{-1}$: 3271 (m), 2929 (s), 1648 (s), 1626 (s)

Mass spectrum [M–H$_2$O]$^+$=324

High resolution MS spectrum: [M]$^+$=342.2256 (C$_{16}$H$_{30}$N$_4$O$_4$); Calcd. value: 342.2267 [α]$_D^{26}$=−9.3° (c=0.90 EtOH)

EXAMPLE 15

N$^2$-[2-(R)-(Hydroxyaminocarbonyl)methyl-1-oxooctyl]-(S)-piperazic acid N,N-dimethylamide Following the procedure described in Example 1, the protecting groups of an N,N-dimethylamide compound, which was prepared by condensing dimethylamine with N$^1$-benzyloxycarbonyl-N$^2$-[2-(R)-(benzyloxyaminocarbonyl)methyl-1-oxooctyl]-(S)-piperazic acid (41 mg), prepared in Referential Example 70, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (21 mg).

NMR spectrum (270 MHz, CDCl$_3$) δ ppm: 0.86 (3H, t, J=6.6 Hz), 1.12–2.07 (14H, complex), 2.29 (1H, dd, J=13.9 and 4.0 Hz), 2.53 (1H, dd, J=13.9 and 12.2 Hz), 2.70–3.19 (overlap to 2H, 3.06 ppm and 2.94 ppm), 2.94 (3H, s), 3.06 (3H, s), 3.92 (1H, m), 5.26 (1H, d, J=11.9 Hz), 5.51 (1H, br.s), 8.01–8.5 (1H, br.s), 9.41–9.70 (1H, br.s)

IR absorption spectrum (film) cm$^{-1}$: 3249 (m), 2929 (s), 1645 (s), 1625 (s)

Mass spectrum [M]$^+$=356

High resolution MS spectrum: [M+H]$^+$=357.2511 (C$_{17}$H$_{33}$N$_4$O$_4$); Calcd. value: 357.2502 [α]$_D^{26}$=+5.9° (c=1.0, EtOH)

EXAMPLE 16

N$^2$-[2-(R)-(Hydroxyaminocarbonyl)methyl-1-oxononyl]-(S)-piperazic acid N-methylamide Following the procedure described in Example 1, the protecting groups of an N-methylamide compound, which was prepared by condensing methylamine with N$^1$-benzyloxycarbonyl-N$^2$-[2-(R)-(benzyloxyaminocarbonyl)methyl-1-oxononyl]-(S)-piperazic acid (46 mg), prepared in Referential Example 80, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (20 mg).

NMR spectrum (270 MHz, CDCl$_3$) δ ppm: 0.87 (3H, t, J=6.6 Hz), 1.00–1.95 (1H, complex), 2.05 (1H, br.d, J=3.3 Hz), 2.28 (1H, br.d, J=3.3 Hz), 2.51 (1H, dd, J=13.9 and 11.2 Hz), 2.78 (3H, d, J=4.6 Hz), 2.82 (1H, m), 3.02 (1H, br.d, J=12.5 Hz), 3.87 (1H, m), 4.73 (1H, d, J=11.9 Hz), 5.06 (1H, br.s), 6.93 (1H, m), 9.91–10.12 (1H, br.s)

IR absorption spectrum (film) cm$^{-1}$: 3268 (m), 2928 (s), 1652 (s), 1626 (s)

Mass spectrum [M+H]$^+$=357

High resolution MS spectrum: [M+H]$^+$=357.2493 (C$_{17}$H$_{33}$N$_4$O$_4$); Calcd. value: 357.2502 [α]$_D^{26}$=−9.5° (c=1.0, EtOH)

EXAMPLE 17

N$^2$-[2-(R)-(Hydroxyaminocarbonyl)methyl-1-oxononyl]-(S)-piperazic acid N,N-dimethylamide Following the procedure described in Example 1, the protecting groups of an N,N-dimethylamide compound, which was prepared by condensing dimethylamine with N¹-benzyloxycarbonyl-N²-[2-(R)-(benzyloxyaminocarbonyl)methyl-1-oxononyl]-(S)-piperazic acid (49 mg), prepared in Referential Example 80, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (10 mg).

NMR spectrum (270 MHz, CDCl$_3$) δ ppm: 0.83 (3H, t, J=6.6 Hz), 1.05–1.78 (14H, complex), 1.80–2.04 (2H, complex), 2.26 (1H, br.d, J=12.5 Hz), 2.50 (1H, br. t, J=12.5 Hz), 2.72–3.12 (2H, complex), 2.93 (3H, s), 3.05 (3H, s), 3.90 (1H, m), 5.24 (1H, d, J=11.9 Hz), 5.53 (1H, m)

IR absorption spectrum (film) cm$^{-1}$: 3260 (m), 2940 (s), 1625 (s)

Mass spectrum [M+H]$^+$=371

High resolution MS spectrum: [M+H]$^+$=371.2677 (C$_{18}$H$_{35}$N$_4$O$_4$); Calcd. value: 371.2658 [α]$_D^{26}$=+7.20 (c=0.81, EtOH)

EXAMPLE 18

N²-[2-(R)-(Hydroxyaminocarbonyl)methyl-1-oxododecyl]-(S)-piperazic acid N-methylamide Following the procedure described in Example 1, the protecting groups of an N-methylamide compound, which was prepared by condensing methylamine with N¹-benzyloxycarbonyl-N²-[2-(R)-(benzyloxyaminocarbonyl)methyl-1-oxododecyl]-(S)-piperazic acid (52 mg), prepared in Referential Example 90, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (7 mg).

NMR spectrum (270 MHz, CDCl$_3$) δ ppm: 0.88 (3H, t, J=6.6 Hz), 1.04–2.12 (22H, complex), 2.19–2.63 (2H, complex), 2.79 (3H, d, J=3.3 Hz), 2.80 (1H, m), 3.03 (1H, br.d, J=13.2 Hz), 3.85 (1H, m), 4.64 (1H, br.d, J=11.9 Hz), 5.05 (1H, br.s), 6.68 (1H, m), 9.48–9.76 (1H, br.s)

IR absorption spectrum (film) cm$^{-1}$: 3267 (m), 2855 (s), 1652 (s), 1625 (s)

Mass spectrum [M]$^+$=398

High resolution MS spectrum: [M-H$_2$O]$^+$=380.2809 (C$_{20}$H$_{36}$N$_4$O$_3$); Calcd. value: 380.2787 [α]$_D^{26}$=-8.9° (c=0.61, EtOH)

EXAMPLE 19

N²-[2-(R)-(Hydroxyaminocarbonyl)methyl-1-oxododecyl]-(S)-piperazic acid N,N-dimethylamide Following the procedure described in Example 1, the protecting groups of an N,N-dimethylamide compound, which was prepared by condensing dimethylamine with N¹-benzyloxycarbonyl-N²-[2-(R)-(benzyloxyaminocarbonyl)methyl-1-oxododecyl]-(S)-piperazic acid (50 mg), prepared in Referential Example 90, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (27 mg).

NMR spectrum (270 MHz, CDCl$_3$) δ ppm: 0.88 (3H, t, J=6.6 Hz), 1.06–1.78 (20H, complex), 1.80–2.02 (2H, complex), 2.29 (1H, dd, J=14.5 and 4.0 Hz), 2.52 (1H, dd, J=14.5 and 10.9 Hz), 2.70–3.12 (2H, complex), 2.94 (3H, s), 3.06 (3H, s), 3.92 (1H, m), 5.26 (1H, d, J=11.9 Hz), 5.50 (1H, br.s), 7.92–8.77 (1H, br.m), 9.59 (1H, m)

IR absorption spectrum (film) cm$^{-1}$: 3262 (m), 2926 (s), 1649 (s), 1627 (s)

Mass spectrum [M]$^+$=412

High resolution MS spectrum: [M]$^+$412.3036 (C$_{21}$H$_{40}$N$_4$O$_4$); Calcd. value: 412.3049 [α]$_D^{26}$=+6.8° (c=1.0, EtOH)

EXAMPLE 20

N²-[2-(R)-(Hydroxyaminocarbonyl)methyl-1-oxo-4-phenylbutyl]-(S)-piperazic acid N-methylamide Following the procedure described in Example 1, the protecting groups of an N-methylamide compound, which was prepared by condensing methylamine with N¹-benzyloxycarbonyl-N²-[2-(R)-(benzyloxyaminocarbonyl)methyl-1-oxo-4-phenylbutyl]-(S)-piperazic acid (45 mg), prepared in Referential Example 100, were removed by catalytic reduction. The product was purified by preparative thin layer chromatograpky through silica gel (20×20 cm size, 0.5 mm thick), using a 13:1 mixture of chloroform and methanol as a developing solvent and a 10:1 mixture of ethyl acetate and methanol as an eluent, to give the desired compound (17 mg).

NMR spectrum (270 MHz, CDCl$_3$) δ ppm: 1.37–2.09 (6H, complex), 2.32 (1H, dd, J=14.2 and 4.3 Hz), 2.43–2.90 (4H, complex), 2.76 (3H, d, J=4.6 Hz), 2.97 (1H, d, J=13.9 Hz), 3.92 (1H, m), 4.74 (1H, d, J=12.0 Hz), 5.07 (1H, d, J=2.1 Hz), 6.82 (1H, br.d, J=4.0 Hz), 7.05–7.31 (5H, complex), 9.69–10.10 (1H, br.s)

IR absorption spectrum (film) cm$^{-1}$: 3440 (m), 3270 (m), 2939 (m), 1640 (s), 1629 (s)

Mass spectrum [M+H]$^+$=363

High resolution MS spectrum: [M]$^+$=362.1947 (C$_{18}$H$_{26}$N$_4$O$_4$); Calcd. value: 362.1954 [α]$_D^{26}$=+1.0° (c=1.0, EtOH)

EXAMPLE 21

N²-[2-(R)-(Hydroxyaminocarbonyl)methyl-1-oxo-4-phenylbutyl]-(S)-piperazic acid N,N-dimethylamide Following the procedure described in Example 1, the protecting groups of an N,N-dimethylamide compound, which was prepared by condensing dimethylamine with N¹-benzyloxycarbonyl-N²-[2-(R)-(benzyloxyaminocarbonyl)methyl-1-oxo-4-phenylbutyl]-(S)-piperazic acid (48 mg), prepared in Referential Example 100, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (9 mg).

NMR spectrum (270 MHz, CDCl$_3$) δ ppm: 1.37–2.04 (6H, complex), 2.32 (1H, m), 2.48–2.69 (3H, complex), 2.71–3.12 (2H, complex), 2.92 (3H, s), 3.03 (3H, s), 3.97 (1H, m), 5.26 (1H, br.d, J=12.5 hz), 5.52 (1H, br.d, J=2.6 Hz), 7.08–7.30 (5H, complex)

IR absorption spectrum (film) cm$^{-1}$: 3250 (m), 2925 (m), 1625 (s)

Mass spectrum [M+Me]⁺=361

High resolution MS spectrum: [M]⁺=376.2126 ($C_{19}H_{28}N_4O_4$); Calcd. value: 376.2110 $[\alpha]_D^{26}$=+19.8° (c=0.71, EtOH)

EXAMPLE 22

$N^2$-[2-(R)-(Hydroxyaminocarbonyl)methyl-1-oxoheptyl]-(S)-piperazic acid N,N-dimethylamide Following the procedure described in Example 1, the protecting groups of an N,N-dimethylamide compound, which was prepared by condensing dimethylamine with $N^1$-benzyloxycarbonyl-$N^2$-[2-(R)-(benzyloxyaminocarbonyl)methyl-1-oxoheptyl]-(S)-piperazic acid (50 mg), prepared in Referential Example 13, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (25 mg).

NMR spectrum (270 MHz, CDCl₃) δppm: 0.85 (3H, t, J=6.6 Hz), 1.12–2.09 (12H, complex), 2.38 (1H, dd, J=14.2 and 4.0 Hz), 2.53 (1H, dd, J=14.2 and 10.8 Hz), 2.70–3.13 (2H, complex), 2.93 (3H, s), 3.05 (3H, s), 3.92 (1H, m), 5.26 (1H, d, J=11.9 Hz), 5.51 (1H, br.s), 9.28–9.92 (1H, br.s)

IR absorption spectrum (film) cm⁻¹: 3265 (m), 2990 (s), 1635 (s), 1625 (s)

Mass spectrum [M]⁺=342

High resolution MS spectrum: [M]⁺=342.2284 ($C_{16}H_{30}N_4O_4$); Calcd. value: 342.2267

EXAMPLE 23

$N^2$-(4-Hydroxyamino-1,4-dioxobutyl)-(S)-piperazic acid N,N-dimethylamide

Following the procedure described in Example 1, the protecting groups of an N,N-dimethylamide compound, which was prepared by condensing dimethylamine with $N^1$-benzyloxycarbonyl-$N^2$-(3-benzyloxyaminocarbonylpropionyl)-(S)-piperazic acid (70 mg), prepared in Referential Example 36, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (25 mg).

NMR spectrum (270 MHz, CDCl₃) δ ppm: 1.47–1.79 (2H, complex), 1.82–2.03 (2H, complex), 2.29–2.56 (2H, complex), 2.62–3.18 (4H, complex), 2.94 (3H, s), 3.07 (3H, s), 5.18 (1H, d, J=11.9 Hz), 5.45 (1H, t, J=4.0 Hz), 9.50–9.89 (1H, br.s)

IR absorption spectrum (liquid film) cm⁻¹: 3260 (m), 2942 (m), 1630 (s)

Mass spectrum [M]⁺=272

High resolution MS spectrum: [M]⁺=272.1471 ($C_{11}H_{20}O_4N_4$); Calcd. value: 272.1484 $[\alpha]_D^{26}$=+4.0° (c=1.0 EtOH)

EXAMPLE 24

$N^2$-(4-Hydroxyamino-1,4-dioxobutyl)-(S)-piperazic acid N-methylamide

Following the procedure described in Example 1, the protecting groups of an N-methylamide compound, which was prepared by condensing methylamine with $N^1$-benzyloxycarbonyl-$N^2$-(3-benzyloxyaminocarbonylpropionyl)-(S)-piperazinecarboxylic acid (82 mg), prepared in Referential Example 36, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (24 mg).

NMR spectrum (270 MHz, CDCl₃) δ ppm: 1.41–1.65 (2H, complex), 1.80 (1H, m), 2.21 (1H, br.d, J=13.1 Hz), 2.37 (2H, t, J=7.3 Hz), 2.65–2.88 (2H, complex), 2.76 (3H, s), 2.90–3.01 (2H, complex), 5.03 (1H, dd, J=4.0 and 3.0 Hz)

IR absorption spectrum (liquid film) cm⁻¹: 3265 (m), 2941 (m), 1641 (s)

Mass spectrum [M]⁺=258

High resolution MS spectrum: [M]⁺=258.1332 ($C_{10}H_{18}N_4O_4$); Calcd. value: 258.1328 $[\alpha]_D^{26}$=−33.5° (c=1.0, EtOH)

EXAMPLE 25

$N^2$-[2-(R)-(Hydroxyaminocarbonyl)methyl-1-oxoheptyl]-(S)-piperazic acid pyrrolidinylamide Following the procedure described in Example 1, the protecting groups of a pyrrolidinylamide compound, which was prepared by condensing pyrrolidine with $N^1$-benzyloxycarbonyl-$N^2$-[2-(R)-(benzyloxyaminocarbonyl)methyl-1-oxoheptyl]-(S)-piperazic acid (42 mg), prepared in Referential Example 13, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (15 mg).

NMR spectrum (270 MHz, CDCl₃) δ ppm: 0.86 (3H, t, J=6.6 Hz), 1.01–2.08 (16H, m), 2.30 (1H, dd, J=13.9 and 4.0 Hz), 2.53 (1H, dd, J=13.9 and 10.9 Hz), 2.83 (1H, m), 3.03 (1H, br.d, J=13.2 Hz), 3.29–3.71 (4H, m), 3.91 (1H, m), 5.30 (1H, m), 5.32 (1H, br.s), 7.88–8.44 (1H, br.s), 9.28–9.70 (1H, br.s)

IR absorption spectrum (liquid film) cm⁻¹: 3250 (m), 2940 (s), 1655 (m), 1620 (s), 1625 (s)

High resolution MS spectrum: [M]⁺=368.2404 ($C_{18}H_{32}N_4O_4$); Calcd. value: 368.2424

EXAMPLE 26

$N^2$-[2-(R)-(Hydroxyaminocarbonyl)methyl-1-oxoheptyl]-(S)-piperazic acid N,N-diethylamide Following the procedure described in Example 1, the protecting groups of an N,N-diethylamide compound, which was prepared by condensing diethylamine with $N^1$-benzyloxycarbonyl-$N^2$-[2-(R)-(benzyloxyaminocarbonyl)methyl-1-oxoheptyl]-(S)-piperazic acid (42 mg), prepared in Referential Example 13, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (19 mg).

NMR spectrum (270 MHz, CDCl$_3$) δ ppm: 0.85 (3H, t, J=6.6 Hz), 1.11 (3H, t, J=6.9 Hz), 1.13–2.08 (15H, complex), 2.29 (1H, dd, J=14.5 and 4.0 Hz), 2.52 (1H, dd, J=14.5 and 11.0 Hz), 2.81 (1H, dd, J=13.9 and 11.9 Hz), 3.04 (1H, br.d, J=13.9 Hz), 3.08–3.47 (3H, complex), 3.53 (1H, m), 3.90 (1H, m), 5.32 (1H, d, J=11.2 Hz), 5.43 (1H, d, J=5.3 Hz), 7.97–8.62 (1H, br.s), 9.25–9.69 (1H, br.s)

IR absorption spectrum (film) cm$^{-1}$: 3255 (m), 2940 (m), 1620 (s)

Mass spectrum [M]$^+$=370

High resolution MS spectrum: [M]$^+$=370.2584 (C$_{18}$H$_{34}$N$_4$O$_4$); Calcd. value: 370.2580

EXAMPLE 27

N$^2$-[2-(R)-(Hydroxyaminocarbonyl)methyl-1-oxoheptyl]-(S)-piperazic acid N-ethylamide Following the procedure described in Example 1, the protecting groups of an N-ethylamide compound, which was prepared by condensing ethylamine with N$^1$-benzyloxycarbonyl-N$^2$-[2-(R)-(benzyloxyaminocarbonyl)methyl-1-oxoheptyl]-(S)-piperazic acid (45 mg), prepared in Referential Example 13, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (19 mg).

NMR spectrum (270 MHz, CDCl$_3$) δ ppm: 0.86 (3H, t, J=6.6 Hz), 1.12 (3H, t, J=7.3 Hz), 1.15–1.95 (11H, complex), 2.05 (1H, m), 2.28 (1H, dd, J=13.9 and 3.3 Hz), 2.51 (1H, dd, J=13.9 and 11.2 Hz), 2.85 (1H, m), 3.02 (1H, br.d, J=12.5 Hz), 3.26 (2H, m), 3.91 (1H, m), 4.72 (1H, d, J=12.5 Hz), 5.05 (1H, s), 6.74 (1H, br.s), 9.73–10.12 (1H, br.s)

IR absorption spectrum (film) cm$^{-1}$: 3255 (m), 2910 (m), 1645 (s), 1605 (s)

Mass spectrum [M−NHEt]$^+$=298

High resolution MS spectrum: [M−NHEt]$^+$=298.1771 (C$_{14}$H$_{24}$N$_3$O$_4$); Calcd. value: 298.1767

EXAMPLE 28

N$^2$-[2-(R)-(Hydroxyaminocarbonyl)methyl-1-oxoheptyl]-(S)-piperazic acid piperazylamide Following the procedure described in Example 1, the protecting groups of an N-benzylpiperazinylamide compound, which was prepared by condensing N-benzylpiperazine with N$^1$-benzyloxycarbonyl-N$^2$-[2-(R)-(benzyloxyaminocarbonyl)methyl-1-oxoheptyl]-(S)-piperazic acid (43 mg), prepared in Referential Example 13, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol, as an eluent, to give the desired compound (6 mg).

NMR spectrum (270 MHz, CDCl$_3$) δ ppm: 0.86 (3H, t, J=6.6 Hz), 1.12–1.77 (10H, complex), 1.79–2.02 (2H, complex), 2.20–2.63 (7H, complex), 2.80 (1H, m), 3.02 (1H, br.d, J=13.2 Hz), 3.32–3.78 (4H, complex), 3.88 (1H, m), 5.17 (1H, d, J=11.5 Hz), 5.50 (1H, dd, J=5.6 and 2.3 Hz), 9.00–9.44 (1H, br.s)

IR absorption spectrum (film) cm$^{-1}$: 3250 (m), 2920 (s), 1630 (s), 1620 (s)

Mass spectrum [M−H$_2$O]$^+$=365

EXAMPLE 29

N$^2$-[2-(R)-(Hydroxyaminocarbonyl)methyl-1-oxoheptyl]-(S)-piperazylamide

Following the procedure described in Example 1, the protecting groups of an amide compound, which was prepared by condensing ammonia and N$^1$-benzyloxycarbonyl-N$^2$-[2-(R)-(benzyloxyaminocarbonyl)methyl-1-oxoheptyl]-(S)-piperazic acid (46 mg), prepared in Referential Example 13 with ammonia, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (10 mg).

NMR spectrum (270 MHz, CD$_3$OD) δ ppm: 0.88 (3H, t, J=6.6 Hz), 1.17–1.78 (10H, complex), 1.97 (1H, m), 2.11 (1H, m), 2.15 (1H, dd, J=13.9 and 5.9 Hz), 2.38 (1H, dd, J=13.9 and 9.2 Hz), 2.78–3.08 (2H, complex), 3.94 (1H, m), 5.13 (1H, br.d, J=5.1 Hz)

IR absorption spectrum (KBr, pellet): 3267 (m), 2930 (s), 1683 (s), 1628 (s)

Mass spectrum [M−NH$_2$]$^+$=298

High resolution MS spectrum: [M−NH$_2$]$^+$=298.1758 (C$_{14}$H$_{24}$N$_3$O$_4$); Calcd. value: 298.1766 [α]$_D^{26}$=+6.4° (c=0.41, EtOH)

EXAMPLE 30

N$^2$-[2-(R)-(Hydroxyaminocarbonyl)methyl-1-oxoheptyl]-(S)-piperazic acid N-isobutylamide Following the procedure described in Example 1, the protecting groups of an N-isobutylamide compound, which was prepared by condensing isobutylamine with N$^1$-benzyloxycarbonyl-N$^2$-[2-(R)-(benzyloxyaminocarbonyl)methyl-1-oxoheptyl]-(S)-piperazic acid (42 mg), prepared in Referential Example 13, were removed by catalytic reduction. The product was purified by preparative thin layer chromatography through silica gel (20×20 cm Size, 0.5 mm thick), using a 13:1 mixture of chloroform and methanol as a developing solvent and a 10:1 mixture of ethyl acetate and methanol as an eluent, to give the desired compound (18 mg).

NMR spectrum (270 MHz, CDCl$_3$) δ ppm: 0.86 (3H, t, J=6.6 Hz), 0.89 (6H, d, J=6.6 Hz), 1.04–2.09 (13H, complex), 2.23 (1H, m), 2.47 (1H, m), 2.69–3.08 (3H, complex), 3.16 (1H, m), 3.88 (1H, m), 4.75 (1H, br.d, J=10.6 Hz), 5.09 (1H, br.s), 7.01 (1H, m)

IR absorption spectrum (KBr, pellet): 3276 (m), 2958 (s), 2931 (s), 1645 (s), 1629 (s)

Mass spectrum [M−H$_2$O]$^+$=352

High resolution MS spectrum: [M]$^+$=370.2583 (C$_{18}$H$_{34}$O$_4$N$_4$); Calcd. value: 370.2580

EXAMPLE 31

N$^2$-[2-(R)-(Hydroxyaminocarbonyl)methyl-1-oxooctyl]-(S)-piperazic acid t-butyl ester Following the procedure described in Example 1, the protecting groups of N$^1$-benzyloxycarbonyl-N$^2$-[2-(R)-(benzyloxyaminocarbonyl)methyl- 1-oxooctyl]-(S)-piperazic acid tert-butyl ester (32 mg), prepared in Referential Example 69, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (17 mg).

NMR spectrum (270 MHz, CDCl$_3$) δ ppm: 0.87 (3H, t, J=6.6 Hz), 1.16–1.70 (12H, complex), 1.48 (9H, s), 1.86 (1H, m), 2.19 (1H, br.d, J=14.4 Hz), 2.32 (1H, dd, J=13.9 and 3.7 Hz), 2.56 (1H, br.dd, J=13.9 and 11.0 Hz), 2.84 (1H, br.t, J=15.0 Hz), 3.01 (1H, br.d, J=14.4 Hz), 3.90 (1H, m), 4.15–4.47 (1H, br.s), 5.20 (1H, d, J=3.9 Hz).

IR absorption spectrum (film) cm$^{-1}$: 3233 (m), 2931 (s), 1728 (s), 1633 (s)

Mass spectrum [M]$^+$=385

High resolution MS spectrum: [M]$^+$=385.2576 (C$_{19}$H$_{35}$N$_3$O$_5$); Calcd. value: 385.2577 [α]$_D^{26}$=−11.4° (c=1.0, EtOH)

m.p. 61°–63° C.

EXAMPLE 32

N$^2$-[2-(R)-(Hydroxyaminocarbonyl)methyl-1-oxo-4-methyl-pentyl]-(S)-piperazic acid N,N-dimethylamide Following the procedure described in Example 1, the protecting groups of an N,N-dimethylamide compound, which was prepared by condensing dimethylamine with N$^1$-benzyloxycarbonyl-N$^2$-[2-(R)-(benzyloxyaminocarbonyl)methyl-1-oxo-4-methylpentyl]-(S)-piperazic acid (49 mg), prepared in Referential Example 101, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (20 mg).

NMR spectrum (270 MHz, CDCl$_3$) δ ppm: 0.88 (3H, t, J=6.6 Hz), 0.92 (3H, d, J=6.6 Hz), 1.20 (1H, m), 1.38–1.78 (4H, complex), 1.80–2.04 (2H, complex), 2.28 (1H, dd, J=13.9 and 4.0 Hz), 2.49 (1H, dd, J=13.9 and 11.2 Hz), 2.70–3.17 (2H, complex, overlap to 3.06 ppm and 2.94 ppm), 2.94 (3H, s), 3.06 (3H, s), 4.04 (1H, m), 5.26 (1H, d, J=11.2 Hz), 5.52 (1H, br.s), 8.15–8.61 (1H, br.s), 9.42–9.74 (1H, br.s)

IR absorption spectrum (film) cm$^{-1}$: 3363 (m), 2954 (s), 1625 (s)

Mass spectrum [M+H]$^+$=329

High resolution MS spectrum: [M+H]$^+$=329.2195 (C$_{15}$H$_{29}$N$_4$O$_4$); Calcd. value: 329.2189 [α]$_D^{26}$=+3.1° (c=1.0, EtOH)

EXAMPLE 33

N$^2$-[2-(R)-(Hydroxyaminocarbonyl)methyl-1-oxodecyl]-(S)-piperazic acid N,N-dimethylamide Following the procedure described in Example 1, the protecting groups of an N,N-dimethylamide compound, which was prepared by condensing dimethylamine with N$^1$-benzyloxycarbonyl-N$^2$-[2-(R)-(benzyloxyaminocarbonyl)methyl-1-oxodecyl]-(S)-piperazic acid (49 mg), prepared in Referential Example 59, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (25 mg).

NMR spectrum (270 MHz, CDCl$_3$) δ ppm: 0.87 (3H, t, J=6.6 Hz), 1.02–1.78 (16H, complex), 1.81–2.04 (2H, complex), 2.29 (1H, dd, J=14.5 and 4.0 Hz), 2.52 (1H, dd, J=14.5 and 10.9 Hz), 2.70–3.11 (2H, complex), 2.94 (3H, s), 3.06 (3H, s), 3.93 (1H, m), 5.26 (1H, d, J=11.2 Hz), 5.51 (1H, br.s), 8.09–8.62 (1H, br.s), 9.50–9.72 (1H, br.s)

IR absorption spectrum (film) cm$^{-1}$: 3250 (w), 2910 (s), 1635 (s), 1625 (s)

Mass spectrum [M]$^+$=384

High resolution MS spectrum: [M]$^+$=384.2738 (C$_{19}$H$_{36}$N$_4$O$_4$); Calcd. value: 384.2737

EXAMPLE 34

N$^2$-[2-(R)-(Hydroxyaminocarbonyl)methyl-1-oxodecyl]-(S)-piperazic acid N-ethylamide Following the procedure described in Example 1, the protecting groups of an N-ethylamide compound, which was prepared by condensing ethylamine with N$^1$-benzyloxycarbonyl-N$^2$-[2-(R)-(benzyloxyaminocarbonyl)methyl-1-oxodecyl]-(S)-piperazic acid (46 mg), prepared in Referential Example 59, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (20 mg).

NMR spectrum (270 MHz, CDCl$_3$) δ ppm: 0.87 (3H, t, J=6.6 Hz), 1.12 (3H, t, J=7.3 Hz), 1.13–1.64 (15H, complex), 1.66–1.93 (2H, complex), .2.04 (1H, m), 2.28 (1H, br.dd, J=13.4 and 2.6 Hz), 2.51 (1H, br.t, J=12.5 Hz), 2.85 (1H, m), 3.02 (1H, br.d, J=12.5 Hz), 3.14–3.40 (2H, complex), 3.96 (1H, m), 4.71 (1H, d, J=11.9 Hz), 5.04 (1H, br.s), 6.73 (1H, br.s), 9.68–10.11 (1H, br.s)

IR absorption spectrum (film) cm$^{-1}$: 3273 (m), 2928 (s), 1650 (s), 1626 (s)

Mass spectrum [M+H$_2$O]$^+$=366

High resolution MS spectrum: [M+H$_2$O]$^+$=366.2625 (C$_{19}$H$_{34}$N$_4$O$_3$); Calcd. value: 366.2631 [α]$_D^{26}$=−5.4° (c=1.0, EtOH)

EXAMPLE 35

N$^2$-[2-(R)-(Hydroxyaminocarbonyl)methyl-1-oxodecyl]-(S)-piperazic acid N,N-diethylamide Following the procedure described in Example 1, the protecting groups of an N,N-diethylamide compound, which was prepared by condensing diethylamine with N$^1$-benzyloxycarbonyl-N$^2$-[2-(R)-(benzyloxyaminocarbonyl)methyl-1-oxodecyl]-(S)-piperazic acid (47 mg), prepared in Referential Example 59, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (8 mg).

NMR spectrum (270 MHz; CDCl$_3$) δ ppm: 0.87 (3H, t, J=6.6 Hz), 1.12 (3H, t, J=6.6 Hz), 1.12–2.05 (21H, complex), 2.31 (1H, dd, J=13.9 and 3.6 Hz), 2.54 (1H, dd, J=13.9 and 10.6 Hz), 2.79 (1H, m), 3.22–3.44 (2H, complex), 3.04 (1H, br.d, J=13.9 Hz), 3.16 (1H, dq, J=13.9 and 6.9 Hz), 3.55 (1H, dq, J=14.5 and 7.3 Hz), 3.87 (1H, m), 5.32 (1H, d, J=11.9 Hz), 5.43 (1H, d, J=4.6 Hz), 7.40–8.03 (1H, br.s), 9.10–9.43 (1H, br.s)

IR absorption spectrum (film) $cm^{-1}$: 3254 (s), 2856 (s), 1622 (s)

Mass spectrum $[M]^+$=412

High resolution MS spectrum: $[M]^+$=412.3034 ($C_{21}H_{40}N_4O_4$); Calcd. value: 412.3050 $[\alpha]_D^{26}$=−11.8° (c=0.39, EtOH)

EXAMPLE 36

$N^2$-[2-(R)-(Hydroxyaminocarbonyl)methyl-1-oxo-4-methyl-pentyl]-(S)-piperazic acid N-methylamide Following the procedure described in Example 1, the protecting groups of an N-methylamide compound, which was prepared by condensing methylamine with $N^1$-benzyloxycarbonyl-$N^2$-[2-(R)-(benzyloxyaminocarbonyl)methyl-1-oxo-4-methylpentyl]-(S)-piperazic acid (33 mg), prepared in Referential Example 101, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (11 mg).

NMR spectrum (270 MHz, CDCl$_3$) δ ppm: 0.89 (3H, d, J=5.9 Hz), 0.93 (3H, d, J=5.9 Hz), 1.22 (1H, m), 1.36–1.97 (5H, complex), 2.05 (1H, m), 2.28 (1H, dd, J=13.2 and 2.6 Hz), 2.49 (1H, dd, J=13.2 and 7.9 Hz), 2.77–3.11 (2H, complex), 2.78 (3H, d, J=4.0 Hz), 3.96 (1H, br.d, J=5.3 Hz), 4.71 (1H, d, J=6.9 Hz), 5.06 (1H, br.d, J=1.3 Hz), 6.85 (1H, br.s), 9.58–10.20 (1H, br.s)

IR absorption spectrum (liquid film) $cm^{-1}$: 3270, (m), 2960 (m), 1650 (s), 1625 (s)

Mass spectrum $[M+H]^+$=315

High resolution MS spectrum: $[M+H]^+$=315.2019 ($C_{14}H_{27}N_4O_4$); Calcd. value: 315.2032 $[\alpha]_D^{26}$=−10.6° (c=1.0, EtOH)

EXAMPLE 37

$N^2$-[2-(R)-(Hydroxyaminocarbonyl)methyl-1-oxoheptyl]-(R)-piperazic acid N-methylamide Following the procedure described in Example 1, the protecting groups of an N-methylamide compound, which was prepared by condensing methylamine with $N^1$-benzyloxycarbonyl-$N^2$-[2-(R)-(benzyloxyaminocarbonyl)methyl-1-oxoheptyl]-(R)-piperazic acid (59 mg), prepared in Referential Example 30, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (19 mg).

NMR spectrum (270 MHz, CDCl$_3$) δ ppm: 0.88 (3H, t, J=6.6 Hz), 1.01–1.80 (11H, complex), 2.28 (1H, br.d, J=12.5 Hz), 2.33–2.90 (3H, complex), 2.77 (3H, br.s), 3.05 (1H, br.d, J=12.5 Hz), 3.99 (1H, m), 4.20 (1H, br.d, J=11.2 Hz), 5.11 (1H, br.s), 7.64 (1H, br.s)

IR absorption spectrum (film) $cm^{-1}$: 3255 (m), 2929 (s), 1637 (s)

Mass spectrum $[M]^+$=328

High resolution MS spectrum: $[M]^+$=328.2108 ($C_{15}H_{28}N_4O_4$); Calcd. value: 328.2110 $[\alpha]_D^{26}$=+70.90 (c=1.0, EtOH)

EXAMPLE 38

$N^2$-[2-(R)-(Hydroxyaminocarbonyl)methyl-1-oxoheptyl]-(R)-piperazic acid N,N-dimethylamide Following the procedure described in Example 1, the protecting groups of an N,N-dimethylamide compound, which was prepared by condensing dimethylamine with $N^1$-benzyloxycarbonyl-$N^2$-[2-(R)-(benzyloxyaminocarbonyl)methyl-1-oxoheptyl]-(R)-piperazic acid (42 mg), prepared in Referential Example 30, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (18 mg).

NMR spectrum (270 MHz, CDCl$_3$) δ ppm: 0.87 (3H, t, J=6.6 Hz), 1.14–1.75 (10H, complex), 1.81–2.05 (2H, complex), 2.28 (2H, d, J=7.3 Hz), 2.70 (1H, m), 2.95 (3H, s), 3.09 (3H, s), 3.11 (1H, m, overlap to 3.09 ppm), 4.10 (1H, m), 4.95 (1H, dd, J=11.2 and 1.3 Hz), 5.43 (1H, dd, J=5.3 and 3.3 Hz), 7.53–7.82 (1H, br.s), 8.68–8.92 (1H, br.s)

IR absorption spectrum (film) $cm^{-1}$: 3261 (s), 2929 (s), 1622 (s)

Mass spectrum $[M]^+$=342

High resolution MS spectrum: $[M]^+$=342.2250 ($C_{16}H_{30}N^4O_4$); Calcd. value: 342.2267 $[\alpha]_D^{26}$=+25.6° (c=1.0., EtOH)

EXAMPLE 39

$N^2$-[2-(S)-(Hydroxyaminocarbonyl)methyl-1-oxoheptyl]-(S)-piperazic acid N-methylamide Following the procedure described in Example 1, the protecting groups of an N-methylamide compound, which was prepared by condensing methylamine with $N^1$-benzyloxycarbonyl-$N^2$-[2-(R)-(benzyloxyaminocarbonyl)methyl-1-oxoheptyl]-(S)-piperazic acid (41 mg), prepared in Referential Example 106, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (8 mg).

NMR spectrum (270 MHz, CDCl$_3$) δ ppm: 0.88 (3H, t, J=6.6 Hz), 1.03–2.05 (11H, complex), 2.18–2.91 (4H, complex), 2.81 (3H, d, J=4.0 Hz), 3.06 (1H, d, J=13.2 Hz), 3.79–4.12 (2H, complex), 5.12 (1H, d, J=4.0 Hz), 7.37 (1H, d, J=4.0 Hz), 9.02–9.53 (1H, br.s)

IR absorption spectrum (film) $cm^{-1}$: 3250 (m), 2930 (s), 1635 (s)

Mass spectrum $[M-H_2O]^+$=310

High resolution MS spectrum: $[M-H_2O]^+$=310.2006 ($C_{15}H_{26}N_4O_3$); Calcd. value: 310.2005 $[\alpha]_D^{26}$=−70.2° (c=0.28, EtOH)

EXAMPLE 40

$N^2$-[2-(S)-(hydroxyaminocarbonyl)methyl-1-oxopentyl]-(S)-piperazic acid tert-butyl ester Following the procedure described in Example 1, the protecting groups of $N^1$-benzyloxycarbonyl-$N^2$-[2-(S)-

(benzyloxyaminocarbonyl)methyl-1-oxopentyl]-(S)-piperazic acid tert-butyl ester (40 mg), prepared in Referential Example 105, were removed by catalytic reduction. The product was purified by preparative thin layer chromatography through silica gel (20×20 cm size, 0.5 mm thick), using a 13:1 mixture of chloroform and methanol as a developing solvent and a 10:1 mixture of ethyl acetate and methanol as an eluent, to give the desired compound (16 mg).

NMR spectrum (270 MHz, CDCl$_3$) δ ppm: 0.87 (3H, t, J=6.6 Hz), 1.17–1.98 (11H, complex), 1.48 (9H, s), 2.05–2.50 (3H, complex), 2.72 (1H, dq, J=2.3 and 12.9 Hz), 3.08 (1H, dd, J=13.7 and 1.9 Hz), 4.00 (1H, m), 4.16 (1H, d, J=12.5 Hz), 5.19 (1H, d, J=4.0 Hz), 8.78–9.33 (1H, br.s)

IR absorption spectrum (film) cm$^{-1}$: 3245 (m), 2940 (s), 1725 (s), 1650 (s), 1630 (s)

Mass spectrum [M]$^+$=371

High resolution MS spectrum: [M]$^+$=371.2408 (C$_{18}$H$_{33}$N$_3$O$_5$); Calcd. value: 371.2421 [α]$_D^{26}$=−30.2° (c=0.48, EtOH)

Referential Example 1

N-Benzyloxycarbonyl-L-isoleucine (N-methyl-N-methoxy)-amide

A solution of N-benzyloxycarbonyl-L-isoleucine (15 g) in dichloromethane (200 ml) was cooled to 0° C., whereupon N,O-dimethylhydroxylamine hydrochloride (5.8 g), dicyclohexylcarbodiimide (DCC, 11.7 g), diisopropylethylamine (10 ml) and 4-dimethylaminopyridine (70 ml) were added successively thereto, and the resulting mixture was stirred at 0° C. for 2.3 hours. After filtering off precipitates, the reaction mixture was poured into hydrochloric acid and extracted with ethyl acetate. The organic extract was successively washed with water and a saturated aqueous solution of sodium chloride, and dried over sodium sulfate. After the solvent had been distilled off under reduced pressure, the residue was purified by column chromatography through silica gel, using a 5:2 mixture of hexane and ethyl acetate as an eluent, to give 16.9 g of the desired compound as colorless crystals. Recrystallization from aqueous methanol gave rise to colorless crystals having a m.p. of 64°–66° C.

NMR spectrum (270 MHz, CDCl$_3$) δ ppm: 0.88 (3H, t, J=7.3 Hz), 0.93 (3H, d, J=6.8 Hz), 1.12 (1H, m), .1.57 (1H, m), 1.73 (1H, m), 3.22 (3H, s), 3.79 (3H, s), 4.67 (1H, br.t, J=8.1 Hz), 5.06 (1H, d, J=12.5 Hz), 5.13 (1H, d, J=12.5 Hz), 5.35 (1H, br.d, J=9.8 Hz), 7.23–7.41 (5H, complex)

IR absorption spectrum (liquid film) cm$^{-1}$: 3306 (m), 1719 (s), 1654 (s)

High resolution MS spectrum: [M+H]$^+$=309.1804 (C$_{16}$H$_{25}$N$_2$O$_4$); Calcd. value: 309.1813 [α]$_D^{26}$=−4.68° (c=2.01, CHCl$_3$)

Referential Example 2

(4S,5S)-4-Benzyloxycarbonylamino-5-methyl-3-oxoheptane

A 0.99M tetrahydrofuran solution (16 ml) of ethylmagnesium bromide was added, dropwise, to a solution of N-benzyloxycarbonyl-L-isoleucyl (N-methyl-N-methoxy) amine (1.71 g) in tetrahydrofuran (40 ml) which had been Cooled to −15° C., under an atmosphere of nitrogen, and the resulting mixture was stirred for 0.6 hour and at room temperature for 0.6 hour. The reaction mixture was poured into a 5% aqueous solution of potassium hydrogensulfate and extracted with ethyl acetate. The organic extract was successively washed with water and a saturated aqueous solution of sodium chloride, and dried over sodium sulfate. After the solvent had been distilled off under reduced pressure, the residue was purified by column chromatography through silica gel, using 4:1 and 2:1 mixtures of hexane and ethyl acetate as the eluent, to give 861 mg (56.2%) of the desired compound. From the eluate, N-benzyloxycarbonyl-L-isoleucyl (N-methyl-N-methoxy)-amine (508 mg), used as a starting material, was recovered. The desired compound was recrystallized from aqueous methanol to give colorless crystals having a m.p. of 57°–58° C.

NMR spectrum (270 MHz, CDCl$_3$) δ ppm: 0.88 (3H, t, J=7.3 Hz), 0.98 (3H, d, J=6.8 Hz), 1.08 (3H, t, J=7.3 Hz), 1.27 (1H, m), 1.90 (1H, m), 2.52 (1H, dd, J=7.3 and 3.9 Hz), 4.36 (1H, dd, J=8.5 and 4.6 Hz), 5.09 (2H, s), 5.36 (1H, br.d, J=8.3 Hz), 7.24–7.40 (5H, complex)

IR absorption spectrum (liquid film) cm$^{-1}$: 3270 (w), 1710 (s)

High resolution MS spectrum [M+H]$^+$=278.1750 (C$_{16}$H$_{24}$NO$_3$); Calcd. value: 278.1756

Referential Example 3

4-(S)-Isopropyl-3-(1-oxoheptyl)-2-oxazolidinone

A solution of 4-(S)-isopropyl-2-oxazolidinone (5.04 g) in tetrahydrofuran (125 ml) was cooled to −78° C. under an atmosphere Of nitrogen. n-Butyl lithium (16 ml, 1.65M, in hexane).was added dropwise to the solution. Heptanoyl chloride (6.4 ml) was added to the resulting mixture after 10 min stirring, and the stirring was continued for another 1.5 hours at the same temperature. The reaction mixture was then poured into a 5% aqueous solution of ammonium chloride and was extracted with ethyl acetate. The organic extract was successively washed with water and a saturated aqueous solution of sodium chloride, and dried over sodium sulfate. After the solvent was distilled off under reduced pressure, the residue was purified by column chromatography through silica gel, using a 8:1 mixture of hexane and ethyl acetate as an eluent, to give the desired compound (9.69 g) as a colorless oil.

NMR spectrum (270 MHz, CDCl$_3$) δ ppm: 0.82–0.97 (3H, t, overlapped to 0.92 ppm), 0.87 (3H, d, J=6.8 Hz), 0.92 (3H, d, J=6.8 Hz), 1.22–1.45 (6H, complex), 1.58–1.75 (2H, complex), 2.38 (1H, d, hep, J=3.4 and 6.8 Hz), 2.77–3.06 (2H, complex), 4.19 (1H, dd, J=8.3 and 3.4 Hz), 4.26 (1H, t, J=8.3 Hz), 4.43 (1H, dt, J=8.3 and 3.4 Hz)

IR absorption spectrum (liquid film) cm$^{-1}$: 1784 (s), 1703 (s)

High resolution MS spectrum [M]$^+$=241.1675 (C$_{13}$H$_{23}$NO$_3$); Calcd. value: 241.1677

Referential Example 4

4-(S)-Isopropyl-3-[2-(R)-tert-butoxycarbonylmethyl-1-oxoheptyl)-2-oxazolidinone

A solution of 4-(S)-isopropyl-3-(1-oxoheptyl)-2-oxazolidinone (519 mg) in tetrahydrofuran (15 ml) was cooled to −15° C., a 0.58M solution (39 ml) of lithium diisopropylamide in tetrahydrofuran was added thereto under an atmosphere of nitrogen, and the resulting mixture was stirred at −78° C for 10 minutes. A solution of tert-butyl bromoacetate (1.7 ml) in tetrahydrofuran (5 ml) was then added thereto and the temperature was allowed to rise gradually to −55° C. over a period of 5.5 hours with stirring.

The reaction mixture was poured into a 5% aqueous solution of ammonium chloride and extracted with ethyl acetate. The organic extract was successively washed with water and a saturated aqueous solution of sodium chloride, and dried over sodium sulfate. After the solvent was distilled off under reduced pressure, the residue was purified by column chromatography through silica gel using a 10:1 mixture of hexane and ethyl acetate as an eluent, to give 697 mg (91.2%) of the desired compound. Recrystallization from aqueous methanol gave rise to crystals having a m.p. of 51°–53° C.

NMR spectrum (270 MHz, CDCl$_3$) δ ppm: 0.86 (3H, t, J=6.4 Hz), 0.91 (3H, d, J=6.3 Hz), 0.93 (3H, d, J=6.3 Hz), 1.14–1.51 (7H, complex), 1.41 (9H, s), 1.62 (1H, m), 2.38 (1H, d, hep, J=3.4 and 6.3 Hz), 2.43 (1H, dd, J=16.6 and 4.9 Hz), 2.74 (1H, dd, J=16.6 and 10.3 Hz), 4.15 (1H, m), 4.20 (1H, dd, J=7.9 and 3.4 Hz), 4.25 (1H, t, J=7.9 Hz), 4.43 (1H, dt, J=7.9 and 3.4 Hz)

IR absorption spectrum (KBr pellet) cm$^{-1}$: 1763 (s), 1730 (s), 1702 (s)

High resolution MS spectrum [M+H]$^+$=356.2449 (C$_{19}$H$_{34}$NO$_5$); Calcd. value: 356.2437 [α]$_D^{26}$=+50.8° (c=1.03, CHCl$_3$)

Referential Example 5

2-(R)-(tert-Butoxycarbonylmethyl)heptanoic acid

A solution of 4-(S)-3-[2-(R)-(tert-butoxycarbonylmethyl)-1-oxoheptyl]-2-oxazolidinone (691 mg), prepared in Referential Example 4, in 40 ml of a 3:1 mixture of tetrahydrofuran and water was cooled to 0° C., and lithium hydroxide hydrate (165 mg) and a 31% aqueous solution of hydrogen peroxide (1.0 ml) were added successively thereto. The resulting mixture was stirred at 0° C. for 1.5 hours, then a 1.5N aqueous solution of sodium sulfite was added thereto. After several minutes stirring, the reaction mixture was poured into a 1N aqueous solution of sodium hydroxide followed by washing with dichloromethane. The pH of the aqueous layer was adjusted to pH 1 to 2 with 1N hydrochloric acid and the mixture was extracted with ethyl acetate. The extract was dried over sodium sulfate and the solvent was distilled off under reduced pressure. The residue was purified by column chromatography through silica gel, using a 8:1 mixture of hexane and ethyl acetate as an eluent, to give 452 mg (95.1%) of the desired compound as a colorless oil.

NMR spectrum (270 MHz, CDCl$_3$) δ ppm: 0.88 (3H, t, J=7.4 Hz), 1.21–1.41 (6H, complex), 1.43 (9H, s), 1.52 (1H, m), 1.65 (1H, m), 2.38 (1H, dd, J=16.5 and 5.3 Hz), 2.62 (1H, dd, J=16.5 and 9.2 Hz), 2.80 (1H, m)

IR absorption spectrum (liquid film) cm$^{-1}$: 1734 (s), 1709 (s)

High resolution MS spectrum [M+H]$^+$=245.1752 (C$_{13}$H$_{25}$O$_4$); Calcd. value: 245.1752 [α]$_D^{26}$=+14.5° (c=1.97, EtOH)

Referential Example 6 tert-Butyl 3-(R)-benzyloxycarbonyloctanoate

Sodium hydrogencarbonate (305 mg) and benzyl bromide (1.0 ml) were added successively to a solution of 2-(R)-(tert-butoxycarbonylmethyl)heptanoic acid (440 mg), prepared in Referential Example 5, in 18 ml of dimethylformamide (DMF), and the resulting mixture was stirred overnight at room temperature. The reaction mixture was poured into water and extracted with ethyl acetate. The organic extract was successively washed with water and a saturated aqueous solution of sodium chloride, and dried over anhydrous sodium sulfate. After the solvent had been distilled off under reduced pressure, the residue was purified by column chromatography through silica gel, using a 20:1 mixture of hexane and ethyl acetate as an eluent, to give 476 mg of the desired compound as a colorless oil.

NMR spectrum (270 MHz, CDCl$_3$) δ ppm: 0.85 (3H, t, J=6.6 Hz), 1.17–1.32 (6H, complex), 1.41 (9H, s), 1.50 (1H, m), 1.61 (1H, m), 2.36 (1H, dd, J=16.5 and 5.3 Hz), 2.65 (1H, dd, J=16.5 and 9.2 Hz), 2.83 (1H, m), 5.09 (1H, d, J=12.5 Hz), 5.18 (1H, d, J=12.5 Hz), 7.24–7.42 (5H, complex)

IR absorption spectrum (liquid film) cm$^{-1}$: 1731 (s)

High resolution MS spectrum [M+H]$^+$=335.2230 (C$_{22}$H$_{31}$O$_4$); Calcd. value: 335.2223 [α]$_D^{26}$=+0.22° (c=7.9, CHCl$_3$)

Referential Example 7

3-(R)-Benzyloxycarbonyloctanoic acid

A 4M hydrochloric acid-dioxane solution (15 ml) was added to tert-butyl 3-(R)-benzyloxycarbonyloctanoate (983 mg), prepared in Referential Example 6, and the resulting mixture was stirred overnight. The reaction mixture was poured into water and extracted with ethyl acetate. The organic extract was dried over anhydrous sodium sulfate and the solvent was distilled off under reduced pressure. The residue was purified by column chromatography through silica gel, using a 30:1 mixture of chloroform and methanol as an eluent, to give 838 mg of the desired compound as a colorless oil.

NMR spectrum (270 MHz, CDCl$_3$) δ ppm: 0.85, (3H, t, J=6.6 Hz), 1.10–1.38 (6H, complex), 1.42–1.77 (2H, complex), 2.48 (1H, dd, J=16.5 and 4.6 Hz), 2.78 (1H, dd, J=16.5 and 9.2 Hz), 2.88 (1H, m), 5.14 (2H, s), 7.23–7.48 (5H, complex), 7.60–9.50 (1H, m)

IR absorption spectrum (liquid film) cm$^{-1}$: 1735 (s), 1712 (s)

High resolution MS spectrum [M]$^+$=278.1527 (C$_{16}$H$_{22}$O$_4$); Calcd. value: 278.1518 [α]$_D^{26}$=+2.4° (c=0.99, EtOH)

Referential Example 8

2,2,2-Trichloroethyl 3-(R)-benzyloxycarbonyloctanoate

Oxalyl chloride (2 ml) was added, under an atmosphere of nitrogen, to a solution of 3-(R)-benzyloxycarbonyloctanoic acid (671 mg), prepared in Referential Example 7, in benzene (10 ml), and the resulting mixture was stirred at 60° C. for 2 hours. Benzene was added thereto, followed by concentration under reduced pressure. After distilling off unreacted oxalyl chloride, the residue was dissolved in tetrahydrofuran (13 ml) under an atmosphere of nitrogen and the solution was cooled to −15° C., followed by the addition of trichloroethanol (1.7 ml) and pyridine (0.23 ml) in turn. The reaction mixture was stirred at −15° C. for 3.3. hours and then poured into 0.5N hydrochloric acid, after which the aqueous mixture was extracted with ethyl acetate. The extract was dried over anhydrous sodium sulfate and the solvent was distilled off under reduced pressure. The residue was purified by column chromatography through silica gel, using a 15:1 mixture of hexane and ethyl acetate as an eluent, to give the desired compound (793 mg) as a colorless oil.

NMR spectrum (270 MHz, CDCl$_3$) δ ppm: 0.85 (3H, t, J=6.6 Hz), 1.12–1.39 (6H, complex), 1.47–1.79 (2H, complex), 2.60 (1H, dd, J=15.5 and 3.3 Hz), 2.89 (1H, dd, J=15.5 and 9.2 Hz), 4.64 (1H, d, J=11.9 Hz), 4.72 (1H, d, J=11.9 Hz), 5.10 (1H, d, J=11.9 Hz), 5.18 (1H, d, J=11.9 Hz), 7.23–7.42 (5H, complex)

IR absorption spectrum (liquid film) cm$^{-1}$: 1757 (s), 1736 (s)

High resolution MS spectrum [M+H]$^+$=409.0734 (C$_{18}$H$_{24}$O$_4$Cl$_3$); Calcd. value: 409.0740 [α]$_D^{26}$=−1.0° (c=6.0, CHCl$_3$)

Referential Example 9

2-(R)-(2,2,2-Trichloroethoxycarbonyl) methylheptanoic acid 2,2,2-Trichloroethyl 3-(R)-benzyloxycarbonyloctanoate (924 mg), prepared in Referential Example 8, was dissolved in methanol (8 ml) and was catalytically reduced by stirring the solution for 2 hours under an atmosphere of hydrogen in the presence of 10% palladium on charcoal (52 mg). After completion of the reaction, the catalyst was removed by celite filtration and the filtrate was concentrated under reduced pressure. The residue was purified by column chromatography through silica gel using a 30:1 mixture of chloroform and methanol as an eluent, to give the desired compound (678 mg) as a colorless oil.

NMR spectrum (270 MHz, CDCl$_3$) δ ppm: 0.89 (3H,, t, J=6.5. Hz), 1.18–1.47 (6H, complex), 1.47–1.82 (2H, complex), 2.61 (1H, dd, J=15.2 and 2.9 Hz), 2.88 (1H, dd, J=15.2 and 9.3 Hz), 2.94 (1H, m), 4.72 (1H, d, J=12.0 Hz), 4.79 (1H, d, J=12.0)

IR absorption spectrum (liquid film) cm$^{-1}$: 1758 (s), 1709 (s)

High resolution spectrum [M+H]$^+$=319.0261 (C$_{11}$H$_{18}$O$_4$Cl$_3$); Calcd. value: 319.0271 [α]$_D^{26}$=+11.1° (c=3.96, EtOH)

Referential Example 10

N$^1$-benzyloxycarbonyl-N$^2$-[1-oxo-2-(R)-2,2,2-trichloroethoxycarbonyl)methylheptyl]-(S)-piperazic acid t-butyl ester Under an atmosphere of nitrogen, oxalyl chloride (0.6 ml) was added to a solution of 2-(R)-(2,2,2-trichloroethoxycarbonyl)methylheptanoic acid (573 mg), prepared in Referential Example 9, in benzene (10 ml), and the resulting mixture was stirred at 50° C. for 2 hours. After adding dry benzene, the mixture was concentrated under reduced pressure to remove an excess of oxalyl chloride. The residue (acid chloride) thus obtained was dissolved in tetrahydrofuran (4 ml) and the solution was added dropwise to a solution of (S)-N$^1$-benzyloxycarbonylpiperazic acid tert-butyl ester (584 mg) and N-ethylmorpholine (0.37 ml) in tetrahydrofuran (7 ml) after cooling to −15° C. under an atmosphere of nitrogen. The resulting mixture was stirred overnight and, during this time, the temperature of the mixture was allowed to rise gradually to room temperature. The reaction mixture was poured into 0.2N hydrochloric acid and extracted with ethyl acetate. The organic extract was successively washed with water and a saturated aqueous solution of sodium chloride, and dried over anhydrous sodium sulfate. After distilling off the solvent under reduced pressure, the residue was purified by column chromatography through silica gel, using a 6:1 mixture of hexane and ethyl acetate as an eluent, to give the desired compound (1004 mg) as a colorless oil.

NMR spectrum (270 MHz, CDCl$_3$) δ ppm: 0.80 (3H, t, J=6.6 Hz), 0.85–2.12 (12H, complex), 1.43 (9H, s), 2.61 (1H, dd, J=17.2 and 3.3 Hz), 2.94 (1H, dd, J=17.2 and 10.0 Hz), 3.13 (1H, m), 3.42 (1H, m), 4.28 (1H, br.d, J=11.3 Hz), 4.61 (1H, d, J=11.9 Hz), 4.77 (1H, d, J=11.9 Hz), 5.13 (1H, d, J=11.9 Hz), 5.21 (1H, d, J=11.9 Hz), 5.27 (1H, dd, J=4.6 and 3.9 Hz), 7.22–7.41 (5H, complex)

IR absorption spectrum (liquid film) cm$^{-1}$: 1739 (s), 1676 (s)

High resolution MS spectrum [M]$^+$=620.1799 (C$_{28}$H$_{39}$N$_2$O$_7$Cl$_3$); Calcd. value: 620.1822 [α]$_D^{26}$=−7.5° (c=2.04, CHCl$_3$)

Referential Example 11

N$^1$-benzyloxycarbonyl-N$^2$-[2-(R)-carboxymethyl-1-oxoheptyl]-(S)-piperazic acid t-butyl ester A 1N aqueous solution of ammonium acetate (2.5 ml) and zinc (1.93 g) were added to a solution of N$^1$-benzyloxycarbonyl-N$^2$-[1-oxo-2-(R)-(2,2,2-trichloroethoxycarbonyl)methylheptyl]-(S)-piperazic acid tert-butyl ester (920 mg), prepared in Referential Example 10, in tetrahydrofuran, and the resulting mixture was vigorously stirred at room temperature for 4 hours. After completion of the reaction, zinc was filtered off and the filtrate was poured into a 5% aqueous solution of potassium hydrogensulfate followed by extraction with ethyl acetate. The organic extract was successively washed with water and a saturated aqueous solution of sodium chloride, and dried over anhydrous sodium sulfate. After distilling off the solvent, the residue was purified by column chromatography through silica gel, using a 20:1 mixture of chloroform and methanol as an eluent, to give the desired compound (632 mg) as a colorless oil.

NMR spectrum (270 MHz, CDCl$_3$) δ ppm: 0.80 (3H, t, J=6.3 Hz), 0.85–2.12 (12H, complex), 1.43 (9H, s), 2.48 (1H, dd, J=17.2 and 4.0 Hz), 2.82 (1H, dd, J=17.2 and 11.1 Hz), 3.09 (1H, m), 3.42 (1H, m), 4.25 (1H, m), 5.12 (1H, d, J=11.9 Hz), 5.21 (1H, d, J=11.9 Hz), 5.27 (1H, dd, J=4.6 and 4.0 Hz), 7.19–7.41 (5H, complex)

IR absorption spectrum (liquid film) cm$^{-1}$: 1737 (s), 1714 (s), 1675 (s)

High resolution MS spectrum [M+H]$^+$=491.2724 (C$_{26}$H$_{39}$N$_2$O$_7$); Calcd. value: 491.2756 [α]$_D^{26}$=−23.1° (c=1.03 EtOH)

Referential Example 12

N$^1$-benzyloxycarbonyl-N$^2$-[2-(R)-benzyloxyaminocarbonyl)methyl-1-oxoheptyl]-(S)-piperazic acid tert-butyl ester N$^1$-benzyloxycarbonyl-N$^2$-[2-(R)-carboxymethyl-1-oxoheptyl]-(S)-piperazic acid tert-Butyl ester (598 mg), prepared in Referential Example 11, was dissolved in 20 ml of a 3:1 mixture of tetrahydrofuran and DMF. The solution was cooled to −15° C., O-benzylhydroxylamine (202 mg), diethyl cyanophosphonate (DEPC, 0.28 ml) and triethylamine (0.34 ml) were successively added thereto, and the resulting mixture was stirred for 2.1 hours. The reaction mixture was poured into 1N hydrochloric acid and extracted with ethyl acetate. The organic extract was successively washed with water and a saturated aqueous solution of sodium chloride, and dried over anhydrous sodium sulfate. After the solvent had been distilled off under reduced pressure, the residue was purified by column chromatography through silica gel, using a 60:1 mixture of chloroform and methanol as an eluent, to give the desired compound (452 mg) and unreacted starting compound (piperazic acid ester, 164 mg).

NMR spectrum (270 MHz, CDCl$_3$) δ ppm: 0.79 (3H, t, J=6.8 Hz), 0.82–2.10 (12H, complex), 1.42 (9H, s), 2.10–2.46 (2H, complex), 3.19 (1H, m), 3.42 (1H, m), 4.24 (1H, br.d, J=11.7 Hz), 4.82 (1H, d, J=11.2 Hz), 4.89 (1H, d, J=11.2 Hz), 5.12 (1H, d, J=12.2 Hz), 5.20 (1H, d, J=12.2 Hz), 5.26 (1H, t, J=3.9 Hz), 7.20–7.48 (10H, complex), 7.99 (1H, m)

IR absorption spectrum (liquid film) cm$^{-1}$: 3426 (m), 1734 (s), 1674 (s)

High resolution MS spectrum [M+H]$^+$=596.3328 (C$_{33}$H$_{46}$N$_3$O$_7$); Calcd. value: 596.3335 [α]$_D^{26}$=−30.7° (c=1.03, CHCl$_3$)

Referential Example 13

N$^1$-Benzyloxycarbonyl-N$^2$-[2-(R)-benzyloxyaminocarbonyl)methyl-1-oxoheptyl]-(S)-piperazic acid Trifluoroacetic acid (1.5 ml) was added to a solution of N$^1$-benzyloxycarbonyl-N$^2$-[2-(R)-benzyloxyaminocarbonyl)methyl-1-oxoheptyl]-(S)-piperazic acid tert-butyl ester (421 mg), prepared in Referential Example 12, in dichloromethane, and the resulting mixture was stirred at room temperature for 2.6 hours. After completion of the reaction, toluene was added to the reaction mixture and the mixture was concentrated under reduced pressure. The residue was purified by column chromatography through silica gel, using a 15:1 mixture of chloroform and methanol as an eluent, to give the desired compound (351 mg) as a colorless oil.

NMR spectrum (270 MHz, CDCl$_3$) δ ppm: 0.50–3.40 (17H, complex), 4.11 (1H, m), 4.81 (1H, d, J=11.2 Hz), 4.88 (1H, d, J=11.2 Hz), 4.99–5.38 (3H, complex), 7.05–7.55 (10H, complex)

IR absorption spectrum (liquid film) cm$^{-1}$: 3224 (m), 1719 (s), 1672 (s)

Referential Example 14

N-Benzyloxycarbonyl-L-valine (N-methyl-N-methoxy)amide

Following the procedure described in Referential Example 1, but using N-benzyloxycarbonyl-L-valine (2.11 g) as a starting compound, the desired compound (2.21 g) was obtained.

NMR spectrum (270 MHz, CDCl$_3$) δ ppm: 0.92 (3H, d, J=6.6 Hz), 0.97 (3H, d, J=6.6 Hz), 2.01 (1H, m), 3.21 (3H, s), 3.78 (3H, s), 4.63 (1H, dd, J=9.2 and 7.3 Hz), 5.06 (1H, d, J=12.5 Hz), 5.13 (1H, d, J=12.5 Hz), 5.42 (1H, br.d, J=9.2 Hz), 7.24–7.42 (5H, complex)

IR absorption spectrum (liquid film) cm$^{-1}$: 3310 (m), 2975 (m), 1720 (s), 1655 (s) [α]$_D^{26}$=+4.4° (c=1.00, CHCl$_3$)

Referential Example 15

4-(S)-Benzyloxycarbonylamino-5-methyl-3-oxohexane

Following the procedure described in Referential Example 2, but using N-benzyloxycarbonyl-L-valine (N-methyl-N-methoxy)amide (2.21 g) as a starting compound, the desired compound (0.882 g) having a m.p. of 49°–50° C. was obtained after recrystallization from hexane.

NMR spectrum (270 MHz, CDCl$_3$) δ ppm: 0.77 (3H, 6., J=6.6 Hz), 1.00 (3H, d, J=6.6 Hz), 1.06 (3H, t, J=7.3 Hz), 2.18 (1H, m), 2.50 (2H, m), 4.36 (1H, dd, J=8.6 and 4.0 Hz), 5.06 (1H, d, J=12.5 Hz), 5.11 (1H, d, J=12.5 Hz), 5.53 (1H, br.d, J=8.6 Hz), 7.23–7.42 (5H, complex)

IR absorption spectrum (liquid film) cm$^{-1}$: 3342 (m), 2967 (m), 1712 (s)

High resolution MS spectrum [M+H]$^+$=264.1609 (C$_{15}$H$_{22}$NO$_3$); Calcd. value: 264.1600 [α]$_D^{26}$=+74.9° (c=0.99, CHCl$_3$)

Referential Example 16

N$^1$-Benzyloxycarbonyl-N$^2$-[2-(R)-(benzyloxyaminocarbonyl)methyl-1-oxoheptyl]-(S)-piperazic acid (4S)-5-methyl-3-oxohexan-4-ylamide 4-(S)-Benzyloxycarbonylamino-5-methyl-3-oxohexane (61 mg), prepared in Referential Example 15, was dissolved in tetrahydrofuran (2.0 ml) and catalytically reduced by stirring for 40 minutes under an atmosphere of hydrogen in the presence of 10% palladium on charcoal (6 mg). After the catalyst had been filtered off, the filtrate was concentrated under reduced pressure to yield 4-(S)-amino-5-methyl-3-oxohexane as a crude product.

N$^1$-Benzyloxycarbonyl-N$^2$-[2-(R)-(benzyloxyaminocarbonyl)methyl-1-oxoheptyl]-(S)-piperazic acid (46 mg), prepared in Referential Example 13, was dissolved in 6.4 ml of a 5:3 mixture of tetrahydrofuran and dimethylformamide. The solution was cooled to 0° C. and DEPC (0.06 ml) and a solution of crude 4-(S)-amino-5-methyl- 3-oxohexane prepared above in tetrahydrofuran (4.0 ml) were added thereto, and the resulting mixture was stirred for 4.7 hours. After completion of the reaction, the reaction mixture was poured into water and extracted with ethyl acetate. The organic extract was successively washed with water and a saturated aqueous solution of sodium chloride, and dried over anhydrous sodium sulfate. After the solvent had been distilled off under reduced pressure, the residue was purified by preparative thin layer chromatography through silica gel (20×20 cm size, 2 mm thick), using a 10:1 mixture of chloroform and methanol as a developing solvent, to give the desired compound (75 mg).

NMR spectrum (270 MHz, CDCl$_3$) δ ppm: 0.66–0.93 (9H, complex), 1.03 (3H, t, J=7.4 Hz), 1.08–2.60 (17H, complex), 3.13 (1H, m), 3.73 (1H, m), 4.12 (1H, m), 4.40 (1H, br.dd, J=7.8 and 5.6 Hz), 4.82 (1H, d, J=12.6 Hz), 4.89 (1H, d, J=12.6 Hz), 4.95 (1H, m), 5.18 (1H, d, J=12.3 Hz), 5.25 (1H, d, J=12.3 Hz), 7.24–7.38 (10H, complex), 7.95–8.22 (2H, complex)

Referential Example 17

N$^1$-Benzyloxycarbonyl-N$^2$-[2-(R)-(benzyloxyaminocarbonyl)methyl-1-oxoheptyl]-(S)-piperazic acid (4S,5S)-5-methyl-3-oxoheptan-4-ylamide Following the procedure described in Referential Example 16, but using (4S,5S)-4-benzyloxycarbonylamino-5-methyl-3-oxoheptane (83 mg), prepared in Referential Example 2, and N$^1$-benzyloxycarbonyl-N$^2$-[2-(R)-(benzyloxyaminocarbonyl)methyl-1-oxoheptyl]-(S)-piperazic acid (115 mg), the desired compound (85 mg) was obtained.

NMR spectrum (270 MHz, CDCl$_3$) δ ppm: 0.66–2.12 (23H, complex), 1.02 (3H, t, J=7.3 Hz), 1.34 (3H, t, J=7.3 Hz), 2.28 (1H, m), 2.46 (2H, br.q, J=7.3 Hz), 3.12 (1H, m), 4.11 (1H, m), 4.21 (1H, t, J=7.0 Hz), 4.82 (1H, d, J=12.2 Hz), 4.87 (1H, d, J=12.2 Hz), 4.92 (1H, m), 5.17 (1H, d, J=11.7 Hz), 5.25 (1H, d, J=11.7 Hz), 7.24–7.48 (10H, complex), 8.12 (1H, m), 8.27 (1H, m)

IR absorption spectrum (liquid film) cm$^{-1}$: 3303 (m), 1714 (m), 1667 (s), 1626 (s), 1530 (m)

High resolution MS spectrum [M+H]$^+$=665.3897 (C$_{37}$H$_{53}$N$_4$O$_7$); Calcd. value: 665.3913

Referential Example 18

N-Benzyloxycarbonyl-D-isoleucine (N-methyl-N-methoxy)-amide

Following the procedure described in Referential Example 1, but using N-benzyloxycarbonyl-D-isoleucine (1.65 g) as a starting material, the desired compound (1.56 g) was obtained as colorless crystals having a m.p. of 64°–66° C., after recrystallization from aqueous methanol.

NMR spectrum (270 MHz, CDCl$_3$) δ ppm: 0.88 (3H, t, J=7.3 Hz), 0.93 (3H, d, J=6.8 Hz), 1.12 (1H, m), 1.57 (1H, m), 1.73 (1H, m), 3.22 (3H, s), 3.79 (3H, s), 4.67 (1H, dd, J=9.8 and 8.1 Hz), 5.06 (1H, d, J=12.5 Hz), 5.13 (1H, d, J=12.5 Hz), 5.35 (1H, br.d, J=9.8 Hz), 7.23–7.41 (5H, complex)

IR absorption spectrum (liquid film) cm$^{-1}$: 3306 (m), 2965 (m), 1719 (s), 1654 (s)

High resolution MS spectrum [M+H]$^+$=309.1804 (C$_{16}$H$_{25}$N$_2$O$_4$); Calcd. value: 309.1813 [α]$_D^{26}$=+4.54° (c=2.05, CHCl$_3$)

Referential Example 19

(4R,5R)-4-Benzyloxycarbonylamino-5-methyl-3-oxoheptane

Following the procedure described in Referential Example 2, but using N-benzyloxycarbonyl-D-isoleucine (N-methyl-N-methoxy)amide as a starting compound, there was obtained the desired compound (0.675 g) having a m.p. of 57°–58° C. after recrystallization from aqueous methanol.

NMR spectrum (270 MHz, CDCl$_3$) δ ppm: 0.88 (3H, t, J=7.3 Hz), 0.98 (3H, d, J=6.8 Hz), 1.04 (1H, m), 1.08 (3H, t, J=7.3 Hz), 1.27 (1H, m), 1.90 (1H, m), 2.52 (2H, m), 4.36 (1H, dd, J=8.3 and 4.6 Hz), 5.09 (2H, s), 5.36 (1H, br.d, J=8.3 Hz), 7.24–7.40 (5H, complex)

IR absorption spectrum (liquid film) cm$^{-1}$: 3270 (w), 2966 (M), 1710 (s)

High resolution. MS spectrum [M+H]$^+$=278.1750 (C$_{16}$H$_{24}$NO$_3$); Calcd. value: 278.1756 [α]$_D^{26}$=−72.2° (c=1.0, CHCl$_3$)

Referential Example 20

N$^1$-Benzyloxycarbonyl-N$^2$-[2-(R)-(benzyloxyaminocarbonyl)methyl-1-oxoheptyl]-(S)-piperazic acid (4R,5R)-5-methyl-3-oxoheptan-4-ylamide Following the procedure described in Referential Example 16, but using (4R,5R)-4-benzyloxycarbonylamino-5-methyl-3-oxoheptane (82 mg), prepared in Referential Example 19, and N$^1$-benzyloxycarbonyl-N$^2$-[2-(R)-(benzyloxyaminocarbonyl)methyl-1-oxoheptyl]-(S)-piperazic acid (95 mg), prepared in. Referential Example 13, as starting materials, the desired compound (42 mg) was obtained, having a small amount of impurities but which was able to be used in the following reaction (Referential Example 109) without further purification.

Referential Example 21

N-Benzyloxycarbonyl-L-leucine (N-methyl-N-methoxy)amide

Following the procedure described in Referential Example 1, but using N-benzyloxycarbonyl-L-leucine (2.45 g) as a starting material, the desired compound was obtained (2.61 g).

NMR spectrum (270 MHz, CDCl$_3$) δ ppm: 0.93 (3H, d, J=6.6 Hz), 0.97 (3H, d, J=6.6 Hz), 1.47 (2H, t, J=6.6 Hz), 1.72 (1H, m), 3.20 (3H, s), 3.79 (3H, s), 4.79 (1H, m), 5.06 (1H, d, J=12.5 Hz), 5.12 (1H, d, J=12.5 Hz), 5.37 (1H, d, J=9.2 Hz), 7.23–7.41 (5H, complex)

IR absorption spectrum (liquid film) cm$^{-1}$: 3306 (m), 2958 (m), 1720 (s), 1660 (s)

High resolution MS spectrum [M]$^+$=308.1742 (C$_{16}$H$_{24}$N$_2$O$_4$); Calcd. value: 308.1736 [α]$_D^{26}$=−8.4° (c=1.01, CHCl$_3$)

Referential Example 22

4-(S)-Benzyloxycarbonylamino-6-methyl-3-oxoheptane

Following the procedure described in Referential Example 2, but using N-benzyloxycarbonyl-L-leucine (N=methyl-N-methoxy)amide (2.49 g) as a starting material, the desired compound was obtained (1.36 g).

NMR spectrum (270 MHz, CDCl$_3$) δ ppm: 0.92 (3H, d, J=6.6. Hz), 0.98 (3H, d, J=6.6 Hz), 1.08 (3H, t, J=7.3 Hz), 1.37 (1H, ddd, J=14.3, 9.5 and 5.0 Hz), 1.55 (1H, ddd, J=14.3, 9.2 and 4.1 Hz), 1.71 (1H, m), 2.54 (2H, m), 4.42 (1H, m), 5.09 (2H, s), 5.37 (1H, br.d, J=7.3 Hz), 7.24–7.45. (5H, complex)

IR absorption spectrum (film) cm$^{-1}$: 3337 (m), 2959 (m), 1713 (s)

High resolution MS spectrum [M−C$_2$H$_5$—CO]$^+$= 220.1358 (C$_{13}$H$_{18}$NO$_2$); Calcd. value: 220.1338 [α]$_D^{26}$=+ 32.9° (c=0.99, CHCl$_3$)

Referential Example 23

N$^1$-Benzyloxycarbonyl-N$^2$-[2-(R)-(benzyloxyaminocarbonyl)methyl-1-oxoheptyl]-(S)-piperazic acid (4S)-6-methyl-3-oxoheptan-4-ylamide Following the procedure described in Referential Example 16, but using 4-(S)-benzyloxycarbonylamino-6-methyl-3-oxoheptane (57 mg), prepared in Referential Example 22 and N$^1$-benzyloxycarbonyl-N$^2$-[2-(R)-(benzyloxyaminocarbonyl)methyl-1-oxoheptyl]-(S)-piperazic acid (42 mg), prepared in Referential Example 13, as starting materials, the desired compound (25 mg) was obtained, having a small amount of impurities but which was able to be used in the following reaction (Example 2) without further purification.

Referential Example 24

2-(S)-[N$^1$-Benzyloxycarbonyl-N$^2$-[2-(R)-(benzyloxyaminocarbonyl)methyl-1) methyl-1-oxoheptyl]-(S)-piperazyl]aminoisovaleric acid N-methyl-N-methoxyamide Following the procedure described in Referential Example 16, but using N-benzyloxycarbonyl-L-valine (N-methyl-N-methoxy)amide (96 mg), prepared in Referential Example 14, and N¹-benzyloxycarbonyl-N²-[2-(R)-(benzyloxyaminocarbonyl)methyl-1-oxoheptyl]-(S)-piperazic acid (48 mg), prepared in Referential Example 13, as starting materials, the desired compound (40 mg) was obtained, having a small amount of impurities but which was able to be used in the following reaction (Example 3) without further purification.

Referential Example 25

Methyl 2-(S)-[N¹-benzyloxycarbonyl-N²-[2-(R)-(benzyloxyaminocarbonyl)methyl-1-oxoheptyl]-(S)-piperazyl]aminoisovalerate N¹-Benzyloxycarbonyl-N²-[2-(R)-(benzyloxyaminocarbonyl)methyl-1-oxoheptyl]-(S)-piperazic acid (41 mg), prepared in Referential Example 13, was dissolved in 3.6 ml of a 3:1 mixture of tetrahydrofuran and dimethylformamide. The solution was cooled to 0° C. and, under an atmosphere of nitrogen, L-valine methyl ester hydrochloride (39 mg), triethylamine (0.025 ml) and DEPC (0.04 ml) were successively added thereto, the resulting mixture was stirred overnight and, during this time, the temperature was allowed to rise gradually to room temperature. After completion of the reaction, the reaction mixture was poured into a 5% aqueous solution of sodium hydrogensulfate and extracted with ethyl acetate. The organic extract was successively washed with water and a saturated aqueous solution of sodium chloride, and dried over anhydrous sodium sulfate. After the solvent had been distilled off under reduced pressure, the residue was purified by preparative thin layer chromatography through silica gel (20×20 cm size, 0.5 mm thick), using a 15:1 mixture of chloroform and methanol as a developing solvent, to give the desired compound (49 mg) containing a small amount of impurities, but which was able to be used in the following reaction (Example 4) without further purification.

Referential Example 26 tert-Butyl 2-(S)-[N¹-benzyloxycarbonyl-N²-[2-(R)-(benzyloxyaminocarbonyl)methyl-1-oxoheptyl]-(S)-piperazinyl]aminoisovalerate Following the procedure described in Referential Example 25, but using valine tert-butyl ester hydrochloride (45 mg) and N¹-benzyloxycarbonyl-N²-[2-(R)-(benzyloxyaminocarbonyl)methyl-1-oxoheptyl]-(S)-piperazic acid (37 mg), prepared in Referential Example 13, as starting materials, the desired compound (42 mg) was obtained, having a small amount of impurities, but which was able to be used in the following reaction (Example 5) without further purification.

Referential Example 27

N¹-benzyloxycarbonyl-N²-[1-oxo-2-(R)-(2,2,2-trichloroethoxycarbonylmethyl)heptyl]-(R)-piperazic acid tert-butyl ester Following the procedure described in Referential Example 10, but using 2-(R)-(2,2,2-trichloroethoxycarbonylmethyl)heptanoic acid (246 mg) and (R)-N¹-benzyloxycarbonylpiperazic acid tert-butyl ester (246 mg) as starting materials, the desired compound (267 mg) was obtained.

NMR spectrum (270 MHz, CDCl$_3$) δ ppm: 0.85 (3H, t, J=6.6 Hz), 0.97–2.14 (12H, complex), 1.43 (3H, s), 2.50 (1H, dd, J=17.5 and 4.9 Hz), 2.95 (1H, dd, J=17.5 and 9.9 Hz), 2.97 (1H, m), 3.28 (1H, m), 4.40 (1H, m), 4.58 (1H, d, J=12.5 Hz), 4.85 (1H, d, J=12.5 Hz), 5.10 (1H, d, J=12.5 Hz), 5.21 (1H, d, J=12.5 Hz), 5.29 (1H, br.d, J=4.3 Hz), 7.22–7.42 (5H, complex)

IR absorption spectrum (liquid film) cm⁻¹: 2931 (m), 1735 (s), 1677 (s)

High resolution MS spectrum [M]⁺=620.1833 (C$_{28}$H$_{39}$N$_2$O$_7$³⁵Cl$_3$); Calcd. value: 620.1823

Referential Example 28

N¹-benzyloxycarbonyl-N²-[2-(R)-carboxymethyl-1-oxoheptyl]-(R)-piperazic acid tert-butyl ester Following the procedure described in Referential Example 11, but using N¹-benzyloxycarbonyl-N²-[1-oxo-2-(R)-(2,2,2-trichloroethoxycarbonylmethyl)heptyl]-(R)-piperazic acid tert-butyl ester (694 mg), prepared in Referential Example 27, there was obtained the desired compound (533 mg).

NMR spectrum (270 MHz, CDCl$_3$) δ ppm: 0.84 (3H, t, J=6.6 Hz), 0.94–2.17 (12H, complex), 1.42 (9H, s), 2.37 (1H, m), 2.80–3.09 (2H, complex), 3.18 (1H, m), 4.39 (1H, m), 5.00–5.36 (3H, complex), 7.18–7.42 (5H, complex)

IR absorption spectrum (liquid film) cm⁻¹: 3190 (w), 2932 (s), 1735 (s), 1679 (s)

High resolution MS spectrum [M+H−H$_2$O]⁺=473.2672 (C$_{26}$H$_{37}$N$_2$O$_6$); Calcd. value: 473.2652

Referential Example 29

N¹-benzyloxycarbonyl-N²-[2-(R)-(benzyloxyaminocarbonyl)methyl-1-oxoheptyl]-(R)-piperazic acid tert-butyl ester Following the procedure described in Referential Example 12, but using N¹-benzyloxycarbonyl-N²-[2-(R)-carboxymethyl-1-oxoheptyl]-(R)-piperazic acid tert-butyl ester (517 mg), prepared in Referential Example 28, and O-benzylhydroxylamine (203 mg) as starting materials, the desired compound (421 mg), was obtained.

NMR spectrum (270 MHz, CDCl$_3$) δ ppm: 0.87 (3H, t, J=6.6 Hz), 0.93–2.38 (14H, complex), 1.42 (9H, s), 2.81–3.32 (2H, complex), 4.32 (1H, m), 4.75–4.95 (2H, complex), 5.10 (1H, d, J=11.9 Hz), 5.20 (1H, d, J=11.9 Hz), 5.27 (1H, m), 7.22–7.46 (10H, complex)

IR absorption spectrum (liquid film) cm⁻¹: 3252 (m), 2931 (s), 1735 (s), 1675 (s)

High resolution MS spectrum [M+H]⁺=596.3327 (C$_{33}$H$_{46}$N$_3$O$_7$); Calcd. value: 596.3335 [α]$_D^{26}$=+37.1° (c=1.00, EtOH)

Referential Example 30

N¹-Benzyloxycarbonyl-N²-[2-(R)-(benzyloxyaminocarbonyl)methyl-1-oxoheptyl]-(R)-piperazic acid Following the procedure described in Referential Example 13, but using N¹-benzyloxycarbonyl-N²-[2-(R)-(2-benzyloxyaminocarbonyl)methyl-1-oxoheptyl]-(R)-piperazic acid tert-butyl ester (56 mg), prepared in Referential Example 29, the desired compound (43 mg) was obtained.

NMR spectrum (270 MHz, CDCl$_3$) δ ppm: 0.83 (3H, t, J=5.8 Hz), 0.97–2.20 (15H, complex), 3.14 (1H, m), 4.24

(1H, m), 4.70–4.95 (2H, br.s), 5.02–5.33 (3H, complex), 7.18–7.48 (10H, complex)

IR absorption spectrum (liquid film) cm$^{-1}$: 3230 (w), 2940 (m), 1720 (s), 1655 (s) [α]$_D^{26}$=+21.4° (c=1.0, EtOH)

Referential Example 31

N$^1$-Benzyloxycarbonyl-N$^2$-[2-(R)-(benzyloxyaminocarbonyl)methyl-1-oxoheptyl]-(R)-piperazic acid (4S,5S)-5-methyl-3-oxoheptan-4-ylamide Following the procedure described in Referential Example 16, but using (4S,5S)-4-benzyloxycarbonylamino-5-methyl-3-oxoheptane (61 mg), prepared in Referential Example 2, and N$^1$-benzyloxycarbonyl-N$^2$-[2-(R)-(benzyloxyaminocarbonyl)methyl-1-oxoheptyl]-(R)-piperazic acid (74 mg), prepared in Referential Example 30, as starting materials, the desired compound (67 mg) was obtained, having a small amount of impurities but which was able to be used in the following reaction (Referential Example 110) without further purification.

Referential Example 32

N$^1$-Benzyloxycarbonyl-N$^2$-[2-(R)-(benzyloxyaminocarbonyl)methyl-1-oxoheptyl]-(R)-piperazic acid (4R,5R)-5-methyl-3-oxoheptan-4-ylamide Following the procedure described in Referential Example 16, but using (4R,5R)-4-benzyloxycarbonylamino-5-methyl-3-oxoheptane (55 mg), prepared in Referential Example 19, and N$^1$-benzyloxycarbonyl-N$^2$-[2-(R)-(benzyloxyaminocarbonyl)methyl-1-oxoheptyl]-(R)-piperazic acid (72 mg), prepared in Referential Example 30, the desired compound (54 mg) was obtained, having a small amount of impurities but which was able to be used in the following reaction (Referential Example 111) without further purification.

Referential Example 33

N$^1$-benzyloxycarbonyl-N$^2$-[3-(2,2,2-trichloroethoxycarbonyl)propionyl]-(S)-piperazic acid tert-butyl ester Following the procedure described in Referential Example 10, but using mono-2,2,2-trichloroethyl succinate (0.253 g) and (S)-N$^1$-benzyloxycarbonylpiperazic acid tert-butyl ester (0.323 g) as starting materials, the desired compound (0.582 g) was obtained.

NMR spectrum (270 MHz, CDCl$_3$) δ ppm: 1.41 (9H, s), 1.48–2.13 (4H, complex), 2.38–3.21 (5H, complex), 4.66 (1H, d, J=12.0 Hz), 4.79 (1H, d, J=12.0 Hz), 4.92–5.42 (3H, complex), 7.25–7.40 (5H, complex)

IR absorption spectrum (liquid film) cm$^{-1}$: 2977 (m), 1731 (s), 1683 (s)

High resolution MS spectrum [M]$^+$=550.1028 (C$_{23}$H$_{29}$N$_2$O$_7$$^{35}$Cl$_3$); Calcd. value: 550.1040 [α]$_D^{26}$=−21.1° (c=1.01, CHCl$_3$)

Referential Example 34

N$^1$-benzyloxycarbonyl-N$^2$-(3-carboxypropionyl)-(S)-piperazic acid tert-butyl ester Following the procedure described in Referential Example 11, but using N$^1$-benzyloxycarbonyl-N$^2$-[3-(2,2,2-trichloroethoxycarbonyl)propionyl]-(S)-piperazic acid tert-butyl ester (0.543 g), prepared in Referential Example 33, as starting materials, the desired compound (0.381 g) was obtained.

NMR spectrum (270 MHz, CDCl$_3$) δ ppm: 1.4 (9H, s), 1.55 (1H, m), 1.78 (1H, m), 1.88–2.11 (2H, complex), 2.33–2.89 (5H, complex), 3.01 (1H, m), 4.91–5.44 (3H, complex), 7.22–7.45 (5H, complex)

IR absorption spectrum (liquid film) cm$^{-1}$: 3195 (m), 2978 (m), 1730 (s), 1683 (s)

High resolution MS spectrum [M+H]$^+$=421.2019 (C$_{21}$H$_{29}$N$_2$O$_7$); Calcd. value: 421.1975

Referential Example 35

N$^1$-benzyloxycarbonyl-N$^2$-(3-benzyloxyaminocarbonylpropionyl)-(S)-piperazic acid tert-butyl ester Following the procedure described in Referential Example 12, but using N$^1$-benzyloxycarbonyl-N$^2$-(3-carboxypropionyl)-(S)-piperazic acid tert-butyl ester (350 mg), prepared in Referential Example 34, and O-benzylhydroxylamine (161 mg) as starting materials, the desired compound (458 mg) was obtained, having a small amount of impurities but which was able to be used in the following reactions (Examples 7 and Referential Example 36) without further purification.

NMR spectrum (270 MHz, CDCl$_3$) δ ppm: 1.42 (9H, s), 1.50–2.12 (4H, complex), 2.48 (2H, m), 2.48 (2H, m), 2.80 (2H, m), 3.09 (2H, m), 4.87 (2H, s), 4.96–5.41 (3H, complex), 7.21–7.47 (10H, complex)

IR absorption spectrum (liquid film) cm$^{-1}$: 3240 (m), 2990 (m), 1725 (s), 1675 (s)

High resolution MS spectrum [M+H]$^+$=526.2546 (C$_{28}$H$_{36}$N$_3$O$_7$); Calcd. value: 526.2552

Referential Example 36

N$^1$-Benzyloxycarbonyl-N$^2$-(3-benzyloxyaminocarbonylpropionyl)-(S)-piperazic acid Following the procedure described in Referential Example 13, but using N$^1$-benzyloxycarbonyl-N$^2$-(3-carboxypropionyl)-(S)-piperazic acid tert-butyl ester (369 mg), prepared in Referential Example 34, as a starting material, there was obtained the desired compound (299 mg).

NMR spectrum (270 MHz, CDCl$_3$) δ ppm: 1.60 (1H, m), 1.69–2.60 (6H, complex), 2.68–2.98 (2H, complex), 3.31 (1H, m), 4.87 (2H, br.s), 3.10–3.32 (3H, complex), 7.18–7.47 (10H, complex)

IR absorption spectrum (liquid film) cm$^{-1}$: 3250 (m), 1720 (s), 1670 (s) [α]$_D^{26}$=−12.8° (c=2.01 EtOH)

Referential Example 37

N$^1$-Benzyloxycarbonyl-N$^2$-(3-benzyloxyaminocarbonylpropionyl)-(S)-piperazic acid (4S,5S)-5-methyl-3-oxoheptan-4-ylamide Following the procedure described in Referential Example 16, but using (4S,5S)-4-benzyloxycarbonylamino-5-methyl-3-oxoheptane (110 mg) and N$^1$-benzyloxycarbonyl-N$^2$-(3-benzyloxyaminocarbonylpropionyl)-(S)-piperazic acid (159 mg), prepared in Referential Example 36, the desired compound (128 mg) was obtained.

NMR spectrum (270 MHz, CDCl$_3$) δ ppm: 0.86 (3H, d, J=6.6. Hz), 1.01–2.00 (7H, complex), 1.02 (3H, t, J=7.2 Hz), 1.38 (3H, t, J=7.2 Hz), 2.02–2.69 (4H, complex), 2.48 (2H, q, J=7.2 Hz), 2.81 (1H, m), 3.32 (1H, m), 4.48 (1H, dd, J=7.3 and 6.6 Hz), 4.89 (2H, s), 5.10 (1H, m), 5.15 (1H, d, J=12.5 Hz), 5.25 (1H, d, J=12.5 Hz), 7.25–7.50 (10H, complex), 7.98 (1H, br.d, J=8.0 Hz), 8.65 (1H, br.s)

IR absorption spectrum (liquid film) cm$^{-1}$: 3320 (m), 2975 (m), 1720 (s), 1700 (s), 1675 (s)

High resolution MS spectrum [M+H]$^+$=595.3134 (C$_{32}$H$_{43}$N$_4$O$_7$); Calcd. value: 595.3131

Referential Example 38

4-(S)-Isopropyl-3-(1-oxo-4-methylpentyl)-2-oxazolidinone

Following the procedure described in Referential Example 3, but using 4-(S)-isopropyl-2-oxazolidone (3.46 g) and isocaproyl chloride (3.98 g) as starting materials, the desired compound (5.21 g) was obtained.

NMR spectrum (270 MHz, CDCl$_3$) δ ppm: 0.83–1.00 (12H, complex), 1.45–1.72 (3H, complex), 2.37 (1H, dhep, J=4.0 and 7.9 Hz), 2.78–3.08 (2H, complex), 4.21 (1H, dd, J=7.9 and 4.0 Hz), 4.27 (1H, t, J=7.9 Hz), 4.44 (1H, dt, J=7.9 and 4.0 Hz)

IR absorption spectrum (liquid film) cm$^{-1}$: 2970 (s), 1780 (s), 1700 (s)

High resolution. MS spectrum [M]$^+$=227.1522 (C$_{12}$H$_{21}$NO$_3$); Calcd. value: 227.1521 [α]$_D^{26}$=+76.3° (c=1.00, CHCl$_3$)

Referential Example 39

4-(S)-isopropyl-3-[2-(R)-tert-butoxycarbonylmethyl-1-oxo-4-methylpentyl]-2-oxazolidinone Following the procedure described in Referential Example 4, but using 4-(S)-isopropyl-3-(1-oxo-4-methylpentyl)-2-oxazolidinone (5.17 g), prepared in Referential Example 38, and tert-butyl bromoacetate (18.5 ml) as starting materials, the desired compound (6.16 g), having a m.p. of 143°–144° C. after recrystallization from aqueous methanol, was obtained.

NMR spectrum (270 MHz, CDCl$_3$) δ ppm: 0.86–0.97 (12H, complex), 1.30 (1H, m), 1.42 (9H, s), 1.45–1.66 (3H, complex), 2.38 (1H, m), 2.44 (1H, dd, J=16.5 and 5.3 Hz), 2.68 (1H, dd, J=16.5 and 9.9 Hz), 4.18–4.31 (2H, complex), 4.42 (1H, dt, J=7.9 and 4.0 Hz)

IR absorption spectrum (film) cm$^{-1}$: 2960 (m), 1764 (s), 1732 (s), 1700 (s)

High resolution MS spectrum [M+H]$^+$=342.2270 (C$_{18}$H$_{32}$NO$_5$); Calcd. value: 342.2280 [α]$_D^{26}$=+41.6° (c=1.00, CHCl$_3$)

Referential Example 40

2-(R)-(tert-Butoxycarbonylmethyl)-4-methylpentanoic acid

Following the procedure described in Referential Example 5, but using 4-(S)-isopropyl-3-[2-(R)-tert-butoxycarbonylmethyl-1-oxo-4-methylpentyl]-2-oxazolidinone (6.14 g), prepared in Referential Example 39, as a starting material, the desired compound (3.99 g) was obtained.

NMR spectrum (270 MHz, CDCl$_3$) δ ppm: 0.91 (3H, d, J=6.6 Hz), 0.94 (3H, d, J=6.6 Hz), 1.29 (1H, m), 1.43 (9H, s), 1.53–1.77 (2H, complex), 2.37 (1H, dd, J=16.3 and 5.3 Hz), 2.59 (1H, dd, J=16.3 and 9.2 Hz), 2.85 (1H, m)

IR absorption spectrum (liquid film) cm$^{-1}$: 2960 (s), 1731 (s), 1710 (s) [α]$_D^{26}$=+14.1° (c=1.00, EtOH)

Referential Example 41 tert-Butyl 3-(R)-Benzyloxycarbonyl-5-methylhexanoate

Following the procedure described in Referential Example 6, but using 2-(R)-(tert-butoxycarbonylmethyl)-4-methylpentanoic acid (2.88 g), prepared in Referential Example 40, as a starting material, the desired compound (2.17 g) was obtained.

NMR spectrum (270 MHz, CDCl$_3$) δ ppm: 0.86 (3H, d, J=6.6 Hz), 0.91 (3H, d, J=6.6 Hz), 1.29 (1H, m), 1.41 (9H, s), 1.49–1.68 (2H, complex), 2.35 (1H, dd, J=16.6 and 5.9 Hz), 2.62 (1H, dd, J=16.6 and 8.4 Hz), 2.90 (1H, m), 5.10 (1H, d, J=12.5 Hz), 5.16 (1H, d, J=12.5 Hz), 7.25–7.40 (5H, complex)

IR absorption spectrum (liquid film) cm$^{-1}$: 2959 (m), 1732 (s)

High resolution MS spectrum [M+H]$^+$=321.2051 (C$_{19}$H$_{29}$O$_4$); Calcd. value: 321.2066 [α]$_D^{26}$=+2.4° (c=4.96, CHCl$_3$)

Referential Example 42

3-(R)-Benzyloxycarbonyl-5-methylhexanoic acid

Following the procedure described in Referential Example 7, but using tert-butyl 3-(R)-benzyloxycarbonyl-5-methylhexanoate (2.10 g), prepared in Referential Example 41, as a starting material, the desired compound (1.73 g) was obtained.

NMR spectrum (270 MHz, CDCl$_3$) δ ppm: 0.87 (3H, d, J=6.6 Hz), 0.92 (3H, d, J=6.6 Hz), 1.31 (1H, m), 1.48–1.69 (2H, complex), 2.48 (1H, dd, J=17.0 and 4.6 Hz), 2.76 (1H, dd, J=17.0 and 9.6 Hz), 2.94 (1H, m), 5.12 (1H, d, J=12.9 Hz), 5.16 (1H, d, J=12.9 Hz), 7.23–7.42 (5H, complex)

IR absorption spectrum (liquid film) cm$^{-1}$: 2959 (m), 1736 (s), 1713 (s)

High resolution MS spectrum [M]$^+$=264.1350 (C$_{15}$H$_{20}$O$_4$); Calcd. value: 264.1362 [α]$_D^{26}$=+6.8° (c=1.00, EtOH)

Referential Example 43

2,2,2-Trichloroethyl 3-(R)-Benzyloxycarbonyl-5-methylhexanoate

Following the procedure described in Referential Example 8, but using 3-(R)-benzyloxycarbonyl-5-methylhexanoic acid (1.70 g), prepared in Referential Example 42, as a starting material, the desired compound (2.20 g) was obtained.

NMR spectrum (270 MHz, CDCl$_3$) δ ppm: 0.88 (3H, d, J=6.6 Hz), 0.92 (3H, d, J=6.6 Hz), 1.38 (1H, m), 1.48–1.72 (2H, m), 2.67 (1H, m), 2.87 (1H, m), 3.01 (1H, m), 4.64 (1H, d, J=12.9 Hz), 4.74 (1H, d, J=12.9 Hz), 5.11 (1H, d, J=13.2 Hz), 5.16 (1H, d, J=13.2 Hz), 7.23–7.43 (5H, complex)

IR absorption spectrum (liquid film) cm$^{-1}$: 2958 (m), 1758 (s), 1736 (s) [α]$_D^{26}$=+1.9° (c=4.03, CHCl$_3$)

Referential Example 44

2-(R)-(2,2,2-Trichloroethoxycarbonyl)methyl-4-methylpentanoic acid

Following the procedure described in Referential Example 9, but using 2,2,2-trichloroethyl 3-(R)- benzyloxycarbonyl-5-methylhexanoate (1.79 g), prepared in Referential Example 43, as a starting material, the desired compound (1.12 g) was obtained.

NMR spectrum (270 MHz, CDCl$_3$) δ ppm: 0.93 (3H, d, J=6.6 Hz), 0.96 (3H, d, J=6.6 Hz), 1.40 (1H, m), 1.55–1.79 (2H, complex), 2.61 (1H, dd, J=16.5 and 4.6 Hz), 2.85 (1H, dd, J=16.5 and 9.2 Hz), 2.97 (1H, m), 4.72 (1H, d, J=12.2 Hz), 4.79 (1H, d, J=12.2 Hz)

IR absorption spectrum (film) cm$^{-1}$: 2960 (m), 1758 (s), 1710 (s)

High resolution MS spectrum [M+H]$^+$=305.0100 (C$_{10}$H$_{16}$O$_4$$^{35}$Cl$_3$); Calcd. value: 305.0114 [α]$_D^{26}$=+11.4° (c=1.08, EtOH)

Referential Example 45

N$^1$-Benzyloxycarbonyl-N$^2$-[2-(R)-carboxymethyl-4-methyl-1-oxopentyl]-(S)-piperazic acid tert-butyl ester Following the procedure described in Referential Example 11, but using N$^1$-Benzyloxycarbonyl-N$^2$-[1-oxo-2-(R)-(2,2,2-trichloroethoxycarbonyl)methyl-4-methylpentyl]-(S)-piperazic acid tert-butyl ester (625 mg), prepared in Referential Example 107, as a starting material, the desired compound (477 mg) was obtained.

NMR spectrum (270 MHz, CDCl$_3$) δ ppm: 0.83 (3H, d, J=6.6 Hz), 0.90 (3H, d, J=6.6 Hz), 1.11–1.62 (4H, complex), 1.43 (9H, s), 1.70–2.12 (3H, complex), 2.52 (1H, dd, J=17.8 and 3.3 Hz), 2.77, (1H, dd, J=17.8 and 10.6 Hz), 3.17 (1H, br.t, J=10.6 Hz), 3.36 (1H, br.t, J=10.9 Hz), 4.24 (1H, m), 5.13 (1H, d, J=12.2 Hz), 5.20 (1H, d, J=12.2 Hz), 5.26 (1H, dd, J=4.6 and 4.0 Hz), 7.22–7.46 (5H, complex)

IR absorption spectrum (film) cm$^{-1}$: 3186 (w), 2958 (m), 1736 (s), 1677 (s)

High resolution MS spectrum [M+H]$^+$=477.2612 (C$_{25}$H$_{37}$N$_2$O$_7$); Calcd. value: 477.2601 [α]$_D^{26}$=19.6° (c=1.01, EtOH)

Referential Example 46

N$^1$-Benzyloxycarbonyl-N$^2$-[2-(R)-(benzyloxyaminocarbonyl)methyl-4-methyl-1-oxopentyl]-(S)-piperazic acid tert-butyl ester Following the procedure described in Referential Example 12, but using N$^1$-benzyloxycarbonyl-N$^2$-[2-(R)-carboxymethyl-4-methyl-1-oxopentyl]-(S)-piperazic acid tert-butyl ester (459 mg), prepared in Referential Example 45, and O-benzylhydroxylamine (234 mg) as starting materials, there was obtained the desired compound (427 mg), which had a small amount of impurities but which was able to be used in the following reaction (Example 11) without further purification.

Referential Example 47

N$^1$-Benzyloxycarbonyl-N$^2$-[2-(R)-(benzyloxyaminocarbonyl)methyl-1-oxoheptyl]-(S)-piperazic acid N-methylamide Following the procedure described in Referential Example 25, but using N$^1$-benzyloxycarbonyl-N$^2$-[2-(R)-(benzyloxycarbonyl)methyl-1-oxoheptyl]-(S)-piperazic acid (39 mg) and methylamine hydrochloride (17 mg) as starting materials, the desired compound (14 mg) was obtained, having a small amount of impurities but which was able to be used in the following reaction (Referential Example 48) without further purification.

Referential Example 48

N$^2$-[2-(R)-(Hydroxyaminocarbonyl)methyl-1-oxoheptyl]-(S)-piperazic acid N-methylamide Following the procedure described in Example 1, the protecting groups of N$^1$-benzyloxycarbonyl-N$^2$-[2-(R)-(benzyloxycarbonyl)methyl-1-oxoheptyl]-(S)-piperazic acid N-methylamide (14 mg), prepared in Referential Example 47, were removed by catalytic reduction. The product was purified by preparative thin layer chromatography silica gel (20×20 cm size, 0.5 mm thick), using a 15:1 mixture of chloroform and methanol as a developing solvent twice, to give the desired compound (5.0 mg).

NMR spectrum (270 MHz, CDCl$_3$) δ ppm: 0.87 (3H, t, J=6.6 Hz), 1.00–2.13 (12H, complex), 2.30 (1H, m), 2.52 (1H, br.t, J=12.5 Hz), 2.79 (3H, d, J=4.5 Hz), 2.82 (1H, m), 3.02 (1H, br.d, J=13.2 Hz), 3.85 (1H, m), 4.61 (1H, d, J=11.9 Hz), 5.05 (1H, br.s), 6.59 (1H, br.s)

IR absorption spectrum (liquid film) cm$^{-1}$: 3270 (m), 2940 (m), 1655 (s), 1625 (s)

High resolution MS spectrum [M]$^+$=328 [α]$_D^{26}$=–8.8° (c=0.45, EtOH)

Referential Example 49

4-(S)-Isopropyl-3-(1-oxodecyl)-2-oxazolidinone

Following the procedure described in Referential Example 3, but using 4-(S)-isopropyl-2-oxazolidone (4.74 g) and decanoyl chloride (7.35 g) as starting materials, the desired compound (9.85 g) was obtained.

NMR spectrum (270 MHz, CDCl$_3$) δ ppm: 0.88 (3H, t, J=6.8 Hz), 0.87 (3H, d, J=6.6 Hz), 0.92 (3H, d, J=6.6 Hz), 1.17–1.43 (12H, complex), 1.59–1.73 (2H, complex), 2.37 (1H, d.hep, J=3.3 and 6.6 Hz), 2.78–3.05 (2H, complex), 4.20 (1H, dd, J=9.2 and 3.3 Hz), 4.26 (1H, dd, J=9.2 and 7.9 Hz), 4.44 (1H, d, t, J=7.9 and 3.3 Hz)

IR absorption spectrum (liquid film) cm$^{-1}$: 2927 (s), 1785 (s), 1703 (s)

High resolution spectrum [M]$^+$=283.2144 (C$_{16}$H$_{29}$NO$_3$); Calcd. value: 283.2147 [α]$_D^{26}$=+61.4° (c=1.00, CHCl$_3$)

Referential Example 50

4-(S)-Isopropyl-3-[2-(R)-tert-butoxycarbonylmethyl-1-oxodecyl]-2-oxazolidinone

Following the procedure described in Referential Example 4, but using 4-(S)-isopropyl-3-(1-oxodecyl)-2-oxazolidinone (9.85 g), prepared in Referential Example 49, and tert-butyl bromoacetate (25.4 ml) as starting materials, the desired compound (9.17 g) having a m.p. of 58°–59° C. was obtained.

NMR spectrum (270 MHz, CDCl$_3$) δ ppm: 0.87 (3H, t, J=6.8 Hz), 0.88 (3H, d, J=6.6 Hz), 0.93 (3H, d, J=6.6 Hz), 1.13–1.37 (12H, complex), 1.41 (9H, s), 1.53–1.70 (2H, complex), 2.38 (1H, d.hep, J=3.3 and 6.6 Hz), 2.43 (1H, dd, J=16.6 and 4.7 Hz), 2.74 (1H, dd, J=16.6 and 10.6 Hz), 4.08–4.30 (3H, complex), 4.44 (1H, dt, J=7.3 and 3.3 Hz)

IR absorption spectrum (liquid film) cm$^{-1}$: 2925 (m), 1764 (s), 1730 (s), 1702 (s)

High resolution MS spectrum [M+H]$^+$=398.2910 (C$_{22}$H$_{40}$NO$_5$); Calcd. value: 398.2907 [α]$_D^{26}$=+46.6° (c=1.00, CHCl$_3$)

Referential Example 51

2-(R)-(tert-Butoxycarbonylmethyl)decanoic acid

Following the procedure described in Referential Example 5, but using 4-(S)-isopropyl-3-[2-(R)- tertbutoxycarbonylmethyl-1-oxodecyl]-2-oxazolidinone (9.08 g), prepared in Referential Example 50, as a starting material, the desired compound (6.14 g) was obtained.

NMR spectrum (270 MHz, CDCl$_3$) δ ppm: 0.88 (3H, t, J=6.6 Hz), 1.18–1.40 (12H, complex), 1.43 (9H, s), 1.51 (1H, m), 1.67 (1H, m), 2.38 (1H, dd, J=16.5 and 5.3 Hz), 2.61 (1H, dd, J=16.5 and 9.2 Hz), 2.80 (1H, m)

IR absorption spectrum (liquid film) cm$^{-1}$: 2858 (s), 1733 (s), 1709 (s)

High resolution MS spectrum [M+H]$^+$=287.2213 (C$_{16}$H$_{31}$O$_4$); Calcd. value: 287.2223 [α]$_D^{26}$=+14.2° (c=1.00, EtOH)

Referential Example 52 tert-Butyl 3-(R)-Benzyloxycarbonylundecanoate

Following the procedure described in Referential Example 6, but using 2-(R)-(tert-butoxycarbonylmethyl)decanoic acid (4.64 g), prepared in Referential Example 51, as a starting material, the desired compound (5.69 g) was obtained.

NMR spectrum (270 MHz, CDCl$_3$) δ ppm: 0.87 (3H, t, J=6.6 Hz), 1.10–1.34 (12H, complex), 1.41 (9H, s), 1.50 (1H, m), 1.61 (1, m), 2.36 (1H, dd, J=16.2 and 5.3 Hz), 2.64 (1H, dd, J=16.2 and 9.2 Hz), 2.83 (1H, m), 5.09 (1H, d, J=12.5 Hz), 5.17 (1H, d, J=12.5 Hz), 7.28–7.44 (5H, complex)

IR absorption spectrum (liquid film) cm$^{-1}$: 2956 (m), 1733 (s)

High resolution MS spectrum [M+H]$^+$=377.2658 (C$_{23}$H$_{37}$O$_4$); Calcd. value: 377.2692 [α]$_D^{26}$=+1.1° (c=1.00, CHCl$_3$)

Referential Example 53

3-(R)-Benzyloxycarbonylundecanoic acid

Following the procedure described in Referential Example 7, but using tert-butyl 3-(R)-benzyloxycarbonylundecanoate (5.62 g), prepared in Referential Example 52, as a starting material, the desired compound (4.07 g) was obtained.

NMR spectrum (270 MHz, CDCl$_3$) δ ppm: 0.87 (3H, t, J=6.6. Hz), 1.10–1.38 (12H, complex), 1.44–1.73 (2H, complex), 2.49 (1H, dd, J=16.2 and 4.3 Hz), 2.79 (1H, dd, J=16.2 and 9.6 Hz), 2.87 (1H, m), 5.12 (1H, d, J=13.2 Hz), 5.17 (1H, d, J=13.2 Hz), 7.13–7.43 (5H, complex)

IR absorption spectrum (liquid film) cm$^{-1}$: 2927 (s), 1737 (s), 1713 (s)

High resolution MS spectrum [M]$^+$=320.1989 (C$_{19}$H$_{28}$O$_4$); Calcd. value: 320.1987 [α]$_D^{26}$=+3.3° (c=1.00, EtOH)

Referential Example 54

2,2,2-Trichloroethyl 3-(R)-Benzyloxycarbonylundecanoate

Following the procedure described in Referential Example 8, but using 3-(R)-benzyloxycarbonylundecanoic acid (3.65 g), prepared in Referential Example 53, as a starting material, the desired compound (3.18 g) was obtained.

NMR spectrum (270 MHz, CDCl$_3$) δ ppm: 0.88 (3H, t, J=6.6 Hz), 1.14–1.38 (12H, complex), 1.48–1.79 (2H, complex), 2.60 (1H, dd, J=15.2 and 4.0 Hz), 2.90 (1H, dd, J=15.2 and 9.2 Hz), 2.96 (1H, m), 4.65 (1H, d, J=12.9 Hz), 4.73 (1H, d, J=12.9 Hz), 5.10 (1H, d, J=12.2 Hz), 5.18 (1H, d, J=12.2 Hz), 7.28–7.43 (5H, complex)

IR absorption spectrum (film) cm$^{-1}$: 2927 (s), 1737 (s), 1713 (s)

High resolution MS spectrum [M]$^+$=452.1099 (C$_{21}$H$_{29}$O$_4$$^{35}$Cl$_2$$^{37}$Cl); Calcd. value: 452.1102 [α]$_D^{26}$=0.44° (c=5.00, CHCl$_3$)

Referential Example 55

2-(R)-(2,2,2-Trichloroethoxycarbonyl)methyldecanoic acid

Following the procedure described in Referential Example 9, but using 2,2,2-trichloroethyl 3-(R)-benzyloxycarbonylundecanoate (3.08 g), prepared in Referential Example 54, as a starting material, the desired compound (1.87 g) was obtained.

NMR spectrum (270 MHz, CDCl$_3$) δ ppm: 0.88 (3H, t, J=6.6 Hz), 1.17–1.46 (12H, complex), 1.51–1.82 (2H, complex), 2.61 (1H, dd, J=15.1 and 3.0 Hz), 2.81–3.10 (2H, complex), 4.72 (1H, d, J=12.2 Hz), 4.79 (1H, d, J=12.2 Hz)

IR absorption spectrum (liquid film) cm$^{-1}$: 2928 (s), 1759 (s), 1710 (s)

High resolution MS spectrum [M+H]$^+$=361.0736 (C$_{14}$H$_{24}$O$_4$$^{35}$Cl$_3$); Calcd. value: 361.0740 [α]$_D^{26}$=+11.5° (c=1.00, EtOH)

Referential Example 56

N$^1$-Benzyloxycarbonyl-N$^2$-[1-oxo-2-(R)-(2,2,2-trichloroethoxycarbonyl)methyldecyl]-(S)-piperazic acid tert-butyl ester Following the procedure described in Referential Example 10, but using 2-(R)-(2,2,2-trichloroethoxycarbonyl)methyldecanoic acid (583 mg), prepared in Referential Example 55, and (S)-N$^1$-benzyloxycarbonylpiperazic acid tert-butyl ester (490 mg) as starting materials, the desired compound was obtained (704 mg).

NMR spectrum (270 MHz, CDCl$_3$) δ ppm: 0.88 (3H, t, J=6.6 Hz), 0.93–2.14 (18H, complex), 1.43 (9H, s), 2.60 (1H, dd, J=17.5 and 3.6 Hz), 2.95 (1H, dd, J=17.5 and 10.9 Hz), 3.14 (1H, m), 3.42 (1H, br.t, J=11.3 Hz), 4.27 (1H, br.d, J=12.5 Hz), 4.61 (1H, d, J=12.2 Hz), 4.78 (1H, d, J=12.2 Hz), 5.14 (1H, d, J=11.9 Hz), 5.21 (1H, d, J=11.9 Hz), 5.27 (1H, t, J=4.3 Hz), 7.23–7.40 (5H, complex)

IR absorption spectrum (liquid film) cm$^{-1}$: 2929 (m), 1740 (s), 1677 (s)

High resolution MS spectrum [M+2H]$^+$=664.2264 (C$_{31}$H$_{45}$O$_7$$^{35}$Cl$_3$); Calcd. value: 664.2263 [α]$_D^{26}$=−6.8° (c=1.00, CHCl$_3$)

Referential Example 57

N$^1$-Benzyloxycarbonyl-N$^2$-[2-(R)-carboxymethyl-1-oxydecyl]-(S)-piperazic acid tert-butyl ester Following the procedure described in Referential Example 11 but using N$^1$-benzyloxycarbonyl-N$^2$-[1-oxo-2-(R)-(2,2,2-trichloroethoxycarbonyl)methyldecyl]-(S)-piperazic acid tert-butyl ester (645 mg), prepared in Referential Example 56, as a starting material, the desired compound was obtained (455 mg).

NMR spectrum (270 MHz, CDCl$_3$) δ ppm: 0.88 (3H, t, J=6.6 Hz), 0.93–2.11 (18H, complex), 1.43 (9H, s), 2.49

(1H, dd, J=17.2 and 3.3 Hz), 2.82 (1H, dd, J=17.2 and 11.2 Hz), 3.09 (1H, m), 3.32 (1H, dd, J=14.2 and 10.7 Hz), 4.25 (1H, br.d, J=8.5 Hz), 5.13 (1H, d, J=12.5 Hz), 5.20 (1H, d, J=12.5 Hz), 5.27 (1H, d, J=4.3 Hz), 7.20–7.40 (5H, complex)

IR absorption spectrum (liquid film) cm$^{-1}$: 3189 (w), 2929 (m), 1736 (s), 1678 (s)

High resolution MS spectrum [M+H]$^+$=533.3249 ($C_{29}H_{45}N_2O_7$); Calcd. value: 533.3227 [α]$_D^{26}$=−21.3° (c=1.00, EtOH)

Referential Example 58

$N^1$-benzyloxycarbonyl-$N^2$-[2-(R)-(benzyloxyaminocarbonyl)methyl-1-oxydecyl]-(S)-piperazic acid tert-butyl ester Following the procedure described in Referential Example 12 but using $N^1$-benzyloxycarbonyl-$N^2$-[2-(R)-carboxymethyl-1-oxodecyl]-(S)-piperazic acid tert-butyl ester (437 mg), prepared in Referential Example 57, as a starting material, the desired compound was obtained (490 mg).

NMR spectrum (270 MHz, CDCl$_3$) δ ppm: 0.87 (3H, t, J=6.6 Hz), 0.92–2.52 (18H, complex), 1.43 (9H, s), 2.10–2.46 (2H, complex), 3.20 (1H, m), 3.41 (1H, m), 4.24 (1H, m), 4.82 (1H, d, J=11.6 Hz), 4.89 (1H, d, J=11.6 Hz), 5.12 (1H, d, J=12.5 Hz), 5.20 (1H, d, J=12.5 Hz), 5.27 (1H, t, J=2.4 Hz), 7.22–7.48 (10H, complex), 8.12 (1H, m)

IR absorption spectrum (liquid film) cm$^{-1}$: 3255 (w), 2928 (s), 1733 (s), 1675 (s)

High resolution MS spectrum [M+H—tBu]$^+$=581.3104 ($C_{32}H_{43}N_3O_7$); Calcd. value: 581.3101 [α]$_D^{26}$=−34.30° (c=1.00, CHCl$_3$)

Referential Example 59

$N^1$-Benzyloxycarbonyl-$N^2$-[2-(R)-(benzyloxyaminocarbonyl)methyl-1-oxodecyl]-(S)-piperazic acid Following the procedure described in Referential Example 13, but using $N^1$-benzyloxycarbonyl-$N^2$-[2-(R)-benzyloxyaminocarbonyl)methyl-1-oxodecyl]-(S)-piperazic acid tert-butyl ester (433 mg), prepared in Referential Example 58, as a starting material, the desired compound (379 mg) was obtained.

NMR spectrum (270 MHz, CDCl$_3$) δ ppm: 0.88 (3H, t, J=6.6 Hz), 0.92–2.59 (20H, complex), 2.51–3.18 (2H, complex), 4.10 (1H, br.d, J=12.5 Hz), 4.83 (1H, t, J=4.5 Hz), 4.93 (1H, d, J=11.2 Hz), 5.00 (1H, d, J=11.2 Hz), 5.01 (1H, d, J=11.9 Hz), 5.18 (1H, d, J=11.9 Hz), 7.14 (1H, br.s), 7.20–7.51 (10H, complex), 12.3 (1H, br.s)

IR absorption spectrum (FT film) cm$^{-1}$: 3228 (w), 2927 (s), 1705 (s), 1672 (s), 1604 (s) [α]$_D^{26}$=−29.0° (c=1.00, EtOH)

Referential Example 60

$N^1$-Benzyloxycarbonyl-$N^2$-[2-(R)-(benzyloxyaminocarbonyl)methyl-1-oxodecyl]-(S)-piperazic acid N-methylamide Following the procedure described in Referential Example 25, but using $N^1$-benzyloxycarbonyl-$N^2$-[2-(R)-benzyloxyaminocarbonyl)methyl-1-oxodecyl]-(S)-piperazic acid tert-butyl ester (44 mg), prepared in Referential Example 59, and methylamine hydrochloride (10 mg) as starting materials, the desired compound (15 mg) was obtained.

NMR spectrum (270 MHz, CDCl$_3$) δ ppm: 0.88 (3H, t, J=6.6 Hz), 0.98–2.59 (20H, complex), 2.70 (3H, d, J=4.6 Hz), 3.08 (1H, m), 3.67 (1H, m), 4.11 (1H, m), 4.83 (1H, d, J=11.2 Hz), 4.88 (1H, d, J=11.2 Hz), 5.13 (1H, t, J=5.3 Hz), 5.21 (2H, s), 7.25–7.49 (10H, complex), 7.71 (1H, m), 8.18 (1H, m)

IR absorption spectrum (film) cm$^{-1}$: 3345 (m), 3225 (m), 2945 (s), 1695 (s), 1670 (s)

Mass spectrum m/z [M–H$_2$O]$^+$=576

Referential Example 61

4-(S)-Isopropyl-3-(1-oxooctyl)-2-oxazolidinone

Following the procedure described in Referential Example 3, but using 4-(S)-isopropyl-2-oxazolidinone (5.06 g) and octanoyl chloride (6.67 g), the desired compound (9.39 g) was obtained.

NMR spectrum (270 MHz, CDCl$_3$) δ ppm: 0.87 (3H, d, J=6.6 Hz), 0.88 (3H, t, overlapped to 0.87 ppm and 0.92 ppm), 0.92 (3H, d, J=6.6 Hz), 1.09–1.42 (8H, complex), 1.50–1.73 (2H, complex), 2.38 (1H, m), 2.70–3.06 (2H, complex), 4.20 (1H, dd, J=9.2 and 3.3 Hz), 4.26 (1H, t, J=9.2 Hz), 4.44 (1H, dt, J=9.2 and 3.3 Hz)

IR absorption spectrum (liquid film) cm$^{-1}$: 2929 (m), 1784 (s), 1702 (s)

Mass spectrum [M]$^+$=255

High resolution MS spectrum [M]$^+$=255.1832 ($C_{14}H_{25}O_3N$); Calcd. value: 255.1835 [α]$_D^{26}$=+74.9° (c=1.0, CHCl$_3$)

Referential Example 62

4-(S)-Isopropyl-3-[2-(R)-tert-butoxycarbonylmethyl-1-oxooctyl]-2-oxazolidinone

Following the procedure described in Referential Example 4, but using 4-(S)-isopropyl-3-(1-oxooctyl)-2-oxazolidinone (5.51 g), prepared in Referential Example 61, and tert-butyl bromoacetate (17 ml), the desired compound (4.13 g) was obtained.

NMR spectrum (270 MHz, CDCl$_3$) δ ppm: 0.87 (3H, t, J=7.3 Hz), 0.91 (3H, d, J=6.3 Hz), 0.93 (3H, d, J=6.3 Hz), 1.15–1.50 (9H, complex), 1.41 (9H, s), 1.62 (1H, m), 2.36 (1H, m), 2.42 (1H, dd, J=16.6 and 4.4 Hz), 2.74 (1H, dd, J=16.6 and 10.3 Hz), 4.08–4.30 (3H, complex), 4.43 (1H, dt, J=7.6 and 3.7 Hz)

IR absorption spectrum (liquid film, kBr pellet): 2931 (m), 1764 (s), 1730 (s), 1703 (s)

Mass Spectrum. [M+H]$^+$=370

High resolution MS spectrum [M+H]$^+$=370.2587 ($C_{20}H_{36}NO_5$); Calcd. value: 370.2593 m.p. 50°–51° C. (H$_2$)—MeOH) [α]$_D^{26}$=+51.9° (c=1.0, CHCl$_3$)

Referential Example 63 tert-Butyl 3-(R)-benzyloxycarbonylnonanoate 4-(S)-Isopropyl-3-[2-(R)-tert-butoxycarbonylmethyl-1-oxooctyl]-2-oxazolidinone (3.98 g), prepared in Referential Example 62 was dissolved in tetrahydrofuran. The solution was cooled to 0° C., and a lithium benzyloxide solution (42 ml), which was prepared from tetrahydrofuran (30 ml), benzyl alcohol (2.4 ml) and a 1.66M solution (9.8 ml) of n-butyllithium in hexane with ice-cooling, was added thereto, and the resulting mixture was stirred at 0° C. for 40 minutes. The reaction mixture was poured into a 5% aqueous solution of potassium hydrogensulfate and extracted with ethyl acetate. The organic extract was successively washed with water and a saturated aqueous solution of sodium chloride, and dried over sodium sulfate. After the solvent had been distilled off under reduced pressure, the residue was purified by column chromatography through silica gel, using a 20:1 mixture of hexane and ethyl acetate as an eluent, to give the desired compound (3.86 g) as a colorless oil.

NMR spectrum (270 MHz, CDCl$_3$) δ ppm: 0.86 (3H, t, J=6.6 Hz), 1.10–1.72 (10H, complex), 1.41 (9H, s), 2.36 (1H, dd, J=16.2 and 5.3 Hz), 2.64 (1H, dd, J=16.2 and 9.2 Hz), 2.83 (1H, m), 5.09 (1H, d, J=12.5 Hz), 5.17 (1H, d, J=12.5 Hz), 7.26–7.41 (5H, complex)

IR absorption. Spectrum (liquid film) cm$^{-1}$: 2931 (m), 1732 (s)

Mass spectrum [M+H—tBu]$^+$=292

High resolution MS spectrum [M+H—tBu]$^+$=292.1677 (C$_{17}$H$_{24}$O$_4$); Calcd. value: 292.1675 [α]$_D^{26}$=+0.38° (c=6.9, CHCl$_3$)

Referential Example 64

3-(R)-Benzyloxycarbonylnonanoic acid

Following the procedure described in Referential Example 7, but using tert-butyl 3-(R)-benzyloxycarbonylnonanoate (3.86 g), prepared in the Referential Example 63, the desired compound (2.73 g) was obtained.

NMR spectrum (270 MHz, CDCl$_3$) δ ppm: 0.86 (3H, t, J=6.6 Hz), 1.09–1.37 (8H, complex), 1.41–1.78 (2H<complex), 2.49 (1H, dd, J=16.3 and 4.4 Hz), 2.79 (1H, dd, J=6.3 and 9.3 Hz), 2.88 (1H, m), 5.12 (1H, d, J=12.2 Hz), 5.17 (1H, d, J=12.2 Hz), 7.23–7.42 (5H, complex)

IR absorption spectrum (liquid film) cm$^{-1}$: 2930 (m), 1736 (s), 1712 (s)

Mass spectrum [M]$^+$=292

High resolution MS spectrum [M]$^+$=292.1679 (C$_{17}$H$_{24}$O$_4$); Calcd. value: 292.1675 [α]$_D^{26}$=+2.0° (c=2.0, EtOH)

Referential Example 65

2,2,2-Trichloroethyl 3-(R)-benzyloxycarbonylnonanoate

Following the procedure described in Referential Example 8, but using 3-(R)-benzyloxycarbonylnonanoic acid (2.7 g), prepared in Referential Example 64, and trichloroethanol (1.7 ml), the compound was obtained (3.17 g).

NMR spectrum (270 MHz, CDCl$_3$) δ ppm: 0.86 (3H, t, J=6.8 Hz), 1.11–1.37 (8H, complex), 1.48–1.78 (2H, complex), 2.60 (1H, dd, J=15.9 and 3.7 Hz), 2.89 (1H, dd, J=15.9 and 9.0 Hz), 2.96 (1H, m), 4.65 (1H, d, J=12.0 Hz), 4.72 (1H, d, J=12.0 Hz), 5.10 (1H, d, J=12.4 Hz), 5.18 (1H, d, J=12.4 Hz), 7.25–7.42 (5H, complex)

IR absorption spectrum (liquid film) cm$^{-1}$: 2930 (m), 1758 (s), 1736 (s)

Mass spectrum [M]$^+$=422

High resolution MS spectrum [M]$^+$=422.0826 (C$_{19}$H$_{25}$O$_4$ ($^{35}$Cl)$_3$); Calcd. value: 422.0819 [α]$_D^{26}$=−0.99° (c=5.9, EtOH)

Referential Example 66

2-(R)-(2,2,2-Trichloroethoxycarbonyl)methyloctanoic acid

Following the procedure described in Referential Example 9, but using 2,2,2-trichloroethyl 3-(R)-benzyloxycarbonylnonanoate (3.12 g), prepared in Referential Example 65, the desired compound (2.39 g) was obtained.

NMR spectrum (270 MHz, CDCl$_3$) δ ppm: 0.88 (3H, t, J=6.8 Hz), 1.18–1.45 (8H, complex), 1.49–1.81 (2H, complex), 2.61 (1H, dd, J=15.1 and 2.9 Hz), 2.88 (1H, dd, J=15.1 and 9.3 Hz), 2.94 (1H, m), 4.72 (1H, d, J=12.2 Hz), 4.79 (1H, d, J=12.2 Hz)

IR absorption spectrum (liquid film) cm$^{-1}$: 2930 (m), 1759 (s), 1710 (s)

Mass spectrum [M+H]$^+$=333

High resolution MS spectrum [M+H]$^+$=333.0453 (C$_{12}$H$_{20}$O$_4$ ($^{35}$Cl$_3$)$_3$); Calcd. value: 333.0428 [α]$_D^{26}$=−11.17° (c=4.0, EtOH)

Referential Example 67

N$^1$-Benzyloxycarbonyl-N$^2$-[1-oxo-2-(R)-(2,2,2-trichloroethoxycarbonyl)methyloctyl]-(S)-piperazic acid tert-butyl ester Following the procedure described in Referential Example 10, but using an acid chloride of 2-(R)-(2,2,2-trichloroethoxycarbonyl)methyloctanoic acid (464 mg), prepared in Referential Example 66, and (S)-N$^1$-benzyloxycarbonylpiperazic acid tert-butyl ester, the desired compound (772 mg) was obtained.

NMR spectrum (270 MHz, CDCl$_3$) δ ppm: 0.84 (3H, t, J=6.6 Hz), 0.90–2.12 (14H, complex), 1.43 (9H, s), 2.60 (1H, dd, J=17.2 and 4.0 Hz), 2.97 (1H, dd, J=17.2 and 9.2 Hz), 3.13 (1H, m), 4.28 (1H, m), 4.61 (1H, d, J=11.9 Hz), 4.78 (1H, d, J=11.9 Hz), 5.13 (1H, d, J=11.9 Hz), 5.21 (1H, d, J=11.9 Hz), 5.27 (1H, dd, J=4.6 and 4.0 Hz), 7.24–7.41 (5H, complex)

IR absorption spectrum (liquid film) cm$^{-1}$: 2931 (m), 1736 (s), 1677 (s)

Mass spectrum [M]$^+$=634

High resolution MS spectrum [M]$^+$=636.1935 (C$_{29}$H$_{41}$O$_7$N$_2$ ($^{35}$Cl)$_2$ ($^{37}$Cl); Calcd. value: 636.1950 [α]$_D^{26}$=−6.9° (c=2 0, CHCl$_3$)

Referential Example 68

N$^1$-Benzyloxycarbonyl-N$^2$-[2-(R)-carboxymethyl-1-oxooctyl]-(S)-piperazic acid tert-butyl ester Following the procedure described in Referential Example 11, but using N$^1$-benzyloxycarbonyl-N$^2$-[1-oxo-2-(R)-(2,2,2-trichloroethoxycarbonyl)methyloctyl]-(S)-piperazic acid tert-butyl ester (765 mg), prepared in Referential Example 67, the desired compound (495 mg) was obtained.

NMR spectrum (270 MHz, CDCl$_3$) δ ppm: 0.83 (3H, t, J=6.6 Hz), 0.96–2.12 (14H, complex), 1.43 (9H, s), 2.48 (1H, dd, J=17.2 and 3.6 Hz), 2.82 (1H, dd, J=17.2 and 10.6 Hz), 3.08 (1H, m), 3.12 (1H, m), 4.25 (1H, m), 5.13 (1H, d, J=12.2 Hz), 5.20 (1H, d, J=12.2 Hz), 5.27 (1H, dd, J=4.6 and 4.0 Hz), 7.22–7.48 (5H, complex)

IR absorption spectrum (liquid film) cm$^{-1}$: 3186 (w), 2931 (m), 1736 (s), 1678 (s)

Mass spectrum [M+H]$^+$=505

High resolution MS spectrum [M+H]$^+$=505.2913 (C$_{27}$H$_{41}$O$_7$N$_2$); Calcd. value: 505.2914 [α]$_D^{26}$=−23.5° (c=1.0, EtOH)

Referential Example 69

N$^1$-benzyloxycarbonyl-N$^2$-[2-(R)-benzyloxyaminocarbonyl)methyl-1-oxooctyl]-(S)-piperazic acid tert-butyl ester Following the procedure described in Referential Example 12, but using N$^1$-benzyloxycarbonyl-N$^2$-[2-(R)- carboxymethyl-1-oxooctyl]-(S)-piperazic acid tert-butyl ester (485 mg), prepared in Referential Example 68, and O-benzylhydroxylamine, the desired compound (577 mg) was obtained.

NMR spectrum (270 MHz, CDCl$_3$) δ ppm: 0.83 (3H, t, J=6.6 Hz), 0.88–2.08 (15H, complex), 1.42 (9H, s), 2.30 (1H, m), 3.20 (1H, m), 3.43 (1H, m), 4.24 (1H, m), 4.82 (1H, d, J=11.6 Hz), 4.88 (1H, d, J=11.6 Hz), 5.13 (1H, d, J=12.2 Hz), 5.20 (1H, d, J=12.2 Hz), 5.25 (1H, br.t, J=4.0 Hz)

IR absorption spectrum (liquid film) cm$^{-1}$: 3251 (w), 2931 (m), 1735 (s), 1675 (s)

Mass spectrum [M]$^+$=609

High resolution MS spectrum [M]$^+$=609.3395 (C$_{34}$H$_{47}$O$_7$N$_3$); Calcd. value: 609.3414 [α]$_D^{26}$=−37.8° (c=1.0, CHCl$_3$)

Referential Example 70

N$^1$-Benzyloxycarbonyl-N$^2$-[2-(R)-benzyloxyaminocarbonyl)methyl-1-oxooctyl]-(S)-piperazic acid Following the procedure described in Referential Example 13, but using N$^1$-benzyloxycarbonyl-N$^2$-[2-(R)-benzyloxyaminocarbonyl)methyl-1-oxooctyl]-(S)-piperazic acid tert-butyl ester (565 mg), prepared in Referential Example 69, the desired compound (458 mg) was obtained.

NMR spectrum (270 MHz, CDCl$_3$) δ ppm: 0.87 (3H, t, J=6.6 Hz), 0.92–2.62 (16H, complex), 2.82–3.29 (2H, complex), 4.10 (1H, m), 4.71–5.40 (5H, complex), 7.00–7.58 (10H, complex), 8.02 (1H, br.s)

IR absorption spectrum (liquid film) cm$^{-1}$: 3227 (m), 2930 (s), 1718 (s), 1672 (s), 1608 (s)

Mass spectrum [M−C$_6$H$_5$]$^+$=476 [α]$_D^{26}$=17.3° (c=1.0, EtOH)

Referential Example 71

4-(S)-Isopropyl-3-(1-oxononyl)-2-oxazolidinone

Following the procedure described in Referential Example 3, but using 4-(S)-isopropyl-2-oxazolidinone (4.99 g) and nonanoyl chloride (7.16 g), the desired compound (10.12 g) was obtained.

NMR spectrum (270 MHz, CDCl$_3$) δ ppm: 0.87 (3H, d, J=7.3 Hz), 0.88 (3H, t, J=6.8 Hz), 0.92 (3H, d, J=7.3 Hz), 1.18–1.45 (12H, complex), 1.56–1.75 (2H, complex), 2.38 (1H, d,hep, J=3.3 and 7.3 Hz), 2.78–3.07 (2H, complex), 4.20 (1H, dd, J=9.2 and 3.3 Hz), 4.26 (1H, t, J=9.2 Hz), 4.44 (1H, dt, J=7.9 and 3.3 Hz)

IR absorption spectrum (liquid film) cm$^{-1}$: 2928 (m), 1785 (s), 1703 (s)

Mass spectrum [M]$^+$=269

High resolution MS spectrum [M]$^+$=269.2001 (C$_{15}$H$_{27}$O$_3$N); Calcd. value: 269.1991 [α]$_D^{26}$=+67.4° (c=1.0, CHCl$_3$)

Referential Example 72

4-(S)-Isopropyl-3-[2-(R)-tert-butoxycarbonylmethyl-1-oxononyl]-2-oxazolidinone

Following the procedure described in Referential Example 4, but using 4-(S)-isopropyl-3-(1-oxononyl)-2-oxazolidinone (10.09 g), prepared in Referential Example 71, and tert-butyl bromoacetate (30 ml), the desired compound (12.62 g) was obtained.

NMR spectrum (270 MHz, CDCl$_3$) δ ppm: 0.87 (3H, t, J=6.9 Hz), 0.91 (3H, d, J=6.6 Hz), 0.93 (3H, d, J=6.6 Hz), 1.17–1.50 (11H, complex), 1.41 (9H, s), 1.60 (1H, m), 2.37 (1H, m), 2.43 (1H, dd, J.=16.5 and 4.0 Hz), 2.74 (1H, dd, J=16.5 and 9.9 Hz), 4.09–4.31 (3H, complex), 4.43 (1H, dt, J=7.9. and 4.0 Hz)

IR absorption spectrum (liquid film, KBr pellet): 2925 (m), 1763 (s), 1731 (s), 1704 (s)

Mass spectrum [M+H]$^+$=384

High resolution MS spectrum [M+H]$^+$=384.2752 (C$_{21}$H$_{38}$O$_5$N); Calcd. value: 384.2750 m.p. 49°–51° (H$_2$O—MeOH) [α]$_d^{26}$=+48.5° (c=1.0, CHCl$_3$)

Referential Example 73 tert-Butyl 3-(R)-benzyloxycarbonyldecanoate

Following the procedure described in Referential Example 63, but using 4-(S)-isopropyl-3-[2-(R)-tertbutoxycarbonylmethyl-1-oxononyl)-2-oxazolidinone (12.44 g), prepared in Referential Example 72, the desired compound (10.88 g) was obtained.

NMR spectrum (270 MHz, CDCl$_3$) δ ppm: 0.87 (3H, t, J=6.6 Hz), 1.14–1.33 (10H, complex), 1.40 (9H, s), 1.49 (1H, m), 1.62 (1H, m), 2.36 (1H, dd, J=16.5 and 6.5 Hz), 2.64 (1H, dd, J=16.5 and 9.2 Hz), 2.84 (1H, m), 5.09 (1H, d, J=12.2 Hz), 5.17 (1H, d, J=12.2 Hz), 7.29–7.40 (5H, complex)

IR absorption spectrum (liquid film) cm$^{-1}$: 2929 (s), 1736 (s)

Mass spectrum [M+H]$^+$=363

High resolution MS spectrum [M+H]$^+$=363.2525 (C$_{22}$H$_{35}$O$_4$); Calcd. value: 363.2535

Referential Example 74

3-(R)-Benzyloxycarbonyldecanoic acid

Following the procedure described in Referential Example 7, but using 3-(R)-tert-butyl benzyloxycarbonyldecanoate (10.50 g), prepared in Referential Example 73, the desired compound (8.29 g) was obtained.

NMR spectrum (270 MHz, CDCl$_3$) δ ppm: 0.87 (3H, t, J=6.6 Hz), 1.10–1.38 (10H, complex), 1.42–1.77 (2H, complex), 2.48 (1H, dd, J=16.2 and 4.6 Hz), 2.79 (1H, dd, J=16.5 and 9.2 Hz), 2.88 (1H, m), 5.12 (1H, d, J=12.5 Hz), 5.17 (1H, d, J=12.5 Hz), 7.25–7.42 (5H, complex) [α]$_D^{26}$= +3.0° (c=1.0, EtOH)

Referential Example 75

2,2,2-Trichloroethyl 3-(R)-benzyloxycarbonyldecanoate

Following the procedure described in Referential Example 8, but using 3-(R)-benzyloxycarbonyldecanoic acid (8.26 g), prepared in Referential Example 74, and trichloroethanol (11.5 ml), the desired compound (11.44 g) was obtained.

NMR spectrum (270 MHz, CDCl$_3$) δ ppm: 0.87 (3H, t, J=6.6 Hz), 1.10–1.39 (10H, complex), 1.46–1.82 (2H, complex), 2.60 (1H, dd, J=15.2 and 4.0 Hz), 2.89 (1H, dd, J=15.2 and 9.2 Hz), 2.96 (1H, m), 4.65 (1H, d, J=12.2 Hz), 4.72 (1H, d, J=12.2 Hz), 5.10 (1H, d, J=11.9 Hz), 5.18 (1H, d, J=11.9 Hz), 7.25–7.45 (5H, complex)

Mass spectrum [M]$^+$=436

High resolution MS spectrum [M]$^+$=436.0992 (C$_{20}$H$_{27}$O$_4$ ($^{35}$Cl)$_3$); Calcd. value: 436.0974 [α]$_D^{26}$=−0.69° (c=4.1, CHCl$_3$)

Referential Example 76

2-(R)-(2,2,2-Trichloroethoxycarbonyl)methylnonanoic acid

Following the procedure described in Referential Example 9, but using 2,2,2-trichloroethyl 3-(R)-benzyloxycarbonyldecanoate (11.39 g), prepared in Referential Example 65, the desired compound (7.66 g) was obtained.

NMR spectrum (270 MHz, CDCl$_3$) δ ppm: 0.88 (3H, t, J=6.8 Hz), 1.15–1.45 (10H, complex), 1.50–1.82 (2H, complex), 2.61 (1H, dd, J=15.1 and 3.4 Hz), 2.80–3.01 (2H, complex), 4.72 (1H, d, J=11.7 Hz), 4.79 (1H, d, J=11.7 Hz)

IR absorption spectrum (liquid film) cm$^{-1}$: 2929 (s), 1759 (s), 1710 (s)

Mass spectrum [M+H]$^+$=347

High resolution MS spectrum [M+H]$^+$=347.0604 (C$_{13}$H$_{22}$O$_4$ ($^{35}$Cl)$_3$); Calcd. value: 347.0584 [α]$_D^{26}$=+11.8° (c=1.0, EtOH)

Referential Example 77

N$^1$-benzyloxycarbonyl-N$^2$-[1-oxo-2-(R)-(2,2,2-trichloroethoxycarbonyl)methylnonyl]-(S)-piperazic acid tert-butyl ester Following the procedure described in Referential Example 10, but using an acid chloride of 2-(R)-(2,2,2-trichloroethoxycarbonyl)methylnonanoic acid (376 mg), prepared in Referential Example 76, and (S)-N'-benzyloxycarbonylpiperazic acid tert-butyl ester (349 mg) there was obtained the desired compound (542 mg).

NMR spectrum (270 MHz, CDCl$_3$) δ ppm: 0.87 (3H, t, J=6.6 Hz), 0.95–1.68 (13H, complex), 1.43 (9H, s), 1.73–2.16 (3H, complex), 2.60 (1H, dd, J=17.2 and 3.6 Hz), 2.94 (1H, dd, J=17.2 and 10.6 Hz), 3.12 (1H, m), 3.43 (1H, m), 4.28 (1H, m), 4.61 (1H, d, J=12.0 Hz), 4.77 (1H, d, J=12.0 Hz), 5.14 (1H, d, J=12.5 Hz), 5.21 (1H, d, J=12.5 Hz), 5.27 (1H, t, J=4.3 Hz), 7.24–7.41 (5H, complex)

IR absorption spectrum (liquid film) cm$^{-1}$: 2930 (s), 1733 (s), 1678 (s)

Mass spectrum [M]$^+$=648

High resolution MS spectrum [M]$^+$=648.2146 (C$_{30}$H$_{43}$O$_7$N$_2$ ($^{35}$Cl)$_3$); Calcd. value: 648.2136 [α]$_D^{26}$=−7.3° (c=1.0, CHCl$_3$)

Referential Example 78

N$^1$-Benzyloxycarbonyl-N$^2$-[2-(R)-carboxymethyl-1-oxononyl]-(S)-piperazic acid tert-butyl ester Following the procedure described in Referential Example 11, but using N$^1$-benzyloxycarbonyl-N$^2$-[1-oxo-2-(R)-(2,2,2-trichloroethoxycarbonyl)methylnonyl]-(S)-piperazic acid tert-butyl ester (541 mg), prepared in Referential Example 77, the desired compound (304 mg) was obtained.

NMR spectrum (270 MHz, CDCl$_3$) δ ppm: 0.86 (3H, t, J=7.0 Hz), 0.91–2.11 (16H, complex), 1.43 (9H, s), 2.48 (1H, dd, J=17.2 and 3.3 Hz), 2.81 (1H, dd, J=17.2 and 10.6 Hz), 3.06 (1H, m), 3.32 (1H, br.t, J=11.2 Hz), 4.24 (1H, m), 5.13 (1H, d, J=11.9 Hz), 5.20 (1H, d, J=11.9 Hz), 5.27 (1H, br.t, J=4.0 Hz), 7.23–7.41 (5H, complex)

IR absorption spectrum (liquid film) cm$^{-1}$: 3184 (m), 2929 (s), 1733 (s), 1640 (s)

Mass spectrum [M+H]$^+$=519

High resolution MS spectrum [M+H]$^+$=519.3064 (C$_{28}$H$_{43}$O$_7$N$_2$) ; Calcd. value: 519.3070

Referential Example 79

N$^1$-Benzyloxycarbonyl-N$^2$-[2-(R)-benzyloxyaminocarbonyl)methyl-1-oxononyl]-(S)-piperazic acid tert-butyl ester Following the procedure described in Referential Example 12, but using tert-butyl N$^1$-benzyloxycarbonyl-N$^2$-[2-(R)-carboxymethyl-1-oxononyl]-(S)-piperazic acid (300 mg), prepared in Referential Example 78, and O-benzylhydroxylamine, the desired compound (347 mg) was obtained.

NMR spectrum (270 MHz, CDCl$_3$) δ ppm: 0.86 (3H, t, J=7.1 Hz), 0.90–2.08 (16H, complex), 1.43 (9H, s), 2.10–2.50 (2H, complex), 3.20 (1H, m), 3.42 (1H, m), 4.25 (1H, m), 4.82 (1H, d, J=11.2 Hz), 4.89 (1H, d, J=11.2 Hz), 5.13 (1H, d, J=12.4 Hz), 5.20 (1H, d, J=12.4 Hz), 5.26 (1H, dd, J=4.4 and 3.4 Hz)

IR absorption spectrum (liquid film) cm$^{-1}$: 3252 (m), 2929 (s), 1735 (s), 1675 (s)

Mass spectrum [M+H]$^+$=624

High resolution MS spectrum [M+H]$^+$=624.3658 (C$_{35}$H$_{50}$O$_7$N$_3$); Calcd. value: 624.3648 [α]$_D^{26}$=−41.8° (c=1.0, CHCl$_3$)

Referential Example 80

N$^1$-Benzyloxycarbonyl-N$^2$-[2-(R)-benzyloxyaminocarbonyl)methyl-1-oxononyl]-(S)-piperazic acid Following the procedure described in Referential Example 13, but using N$^1$-benzyloxycarbonyl-N$^2$-[2-(R)-benzyloxyaminocarbonyl)methyl-1-oxononyl]-(S)-piperazic acid tert-butyl ester (339 mg), prepared in Referential Example 79, the desired compound (249 mg) was obtained.

NMR spectrum (270 MHz, CDCl$_3$) δ ppm: 0.89 (3H, t, J=6.7 Hz), 0.92–2.07 (16H, complex), 2.10–2.52 (2H, complex), 2.88–3.22 (2H, complex), 4.10 (1H, m), 4.68–5.33 (5H, complex), 7.00–7.50 (10H, complex), 12.30 (1H, m)

IR absorption spectrum (liquid film) cm$^{-1}$: 3220 (m), 2928 (s), 1713 (s), 1672 (s), 1601 (s)

Mass spectrum [M−NHOBn]$^+$=445 [α]$_D^{26}$=−23.1° (c=1.0, EtOH)

Referential Example 81

4-(S)-Isopropyl-3-(1-oxododecyl)-2-oxazolidinone

Following the procedure described in Referential Example 3, but using 4-(S)-isopropyl-2-oxazolidinone (5.39 g) and dodecanoyl chloride (9.46 g), the desired compound (11.3 g) was obtained as a colorless oil.

NMR spectrum (270 MHz, CDCl$_3$) δ ppm: 0.87 (3H, d, J=6.9 Hz), 0.88 (3H, t, J=0.87 ppm and 0.92 ppm, overlapped), 0.92 (3H, d, J=6.9 Hz), 1.17–1.43 (16H, complex), 1.53–1.78 (2H, complex), 2.38 (1H, d,hep, J=3.3 and 6.9 Hz), 2.77–3.07 (2H, complex), 4.20 (1H, dd, J=8.6 and 3.3 Hz), 4.26 (1H, t, J=8.6 Hz), 4.44 (1H, dt, J=8.6 and 3.3 Hz)

IR absorption spectrum (liquid film) cm$^{-1}$: 2925 (s), 1785 (s), 1704 (s)

Mass Spectrum. [M+H]⁺=312

High resolution MS spectrum [M+H]⁺=312.2532 ($C_{18}H_{34}O_3N$) ; Calcd. value: 312.2539 $[\alpha]_D^{26}$=+54.1° (c=1.0, $CHCl_3$)

Referential Example 82

4-(S)-Isopropyl-3-[2-(R)-tert-butoxycarbonylmethyl-1-oxododecyl]-2-oxazolidinone Following the procedure described in Referential Example 4, but using 4-(S)-isopropyl-3-(1-oxododecyl)-2-oxazolidone (11.27 g), prepared in Referential Example 81, and tert-butyl bromoacetate (30 ml), the desired compound (14.10 g) was obtained.

NMR spectrum (270 MHz, $CDCl_3$) δ ppm: 0.88 (3H, t, J=7.3 Hz), 0.91 (3H, d, J=6.6 Hz), 0.93 (3H, d, J=6.6 Hz), 1.11–1.51 (17H, complex), 1.41 (9H, s), 1.61 (1H, m), 2.37 (1H, m), 2.42 (1H, dd, J=16.6 and 4.4 Hz), 2.74 (1H, dd, J=16.6 and 10.3 Hz), 4.09–4.30 (3H, complex), 4.43 (1H, dt, J=7.8 and 3.7 Hz)

IR absorption spectrum (liquid film kBr pellet) cm⁻¹: 2922 (s), 1764 (s), 1730 (s), 1700 (s)

Mass spectrum [M+H—tBu]⁺=369.2505

High resolution MS spectrum [M+H—tBu]⁺=369.2505 ($C_{20}H_{35}O_5N$); Calcd. value: 369.2515 m.p. 42°–43° ($H_2O$—MeOH) $[\alpha]_D^{26}$=+45.0° (c=1.0, $CHCl_3$)

Referential Example 83 tert-Butyl 3-(R)-benzyloxycarbonyltridecanoate

Following the procedure described in Referential Example 63, but using 4-(S)-isopropyl-3-[2-(R)-tertbutoxycarbonylmethyl-1-oxododecyl]-2-oxazolidinone (13.67 g), prepared in Referential Example 82, the desired compound was obtained (11.92 g).

$C_{25}H_{40}O_4$ (FW=404)

NMR spectrum (270 MHz, $CDCl_3$) δ ppm: 0.88 (3H, t, J=6.6 Hz), 1.15–1.71 (18H, complex), 1.40 (9H, s), 2.36 (1H, dd, J=16.2 and 5.3 Hz), 2.64 (1H, dd, J=16.2 and 9.2 Hz), 2.83 (1H, m), 5.09 (1H, d, J=12.5 Hz), 5.17 (1H, d, J=12.5 Hz), 7.27–7.40 (5H, complex)

IR absorption spectrum (liquid film) cm⁻¹: 2927 (s), 1734 (s)

Mass spectrum [M+H—tBu]⁺=348

High resolution MS spectrum [M+H—tBu]⁺=348.2318 ($C_{21}H_{32}O_4$); Calcd. value: 348.2301 $[\alpha]_D^{26}$=+0.76° (c=5.0, $CHCl_3$)

Referential Example 84

3-(R)-Benzyloxycarbonyltridecanoic acid

Following the procedure described in Referential Example 7, but using tert-butyl 3-(R)-benzyloxycarbonyltridecanoate (11.62 g), prepared in Referential Example 83, the desired compound (9.41 g) was obtained.

$C_{21}H_{32}O_4$ (FW=348)

NMR spectrum (270 MHz, $CDCl_3$) δ ppm: 0.88 (3H, t, J=6.6 Hz), 1.12–1.35 (16H, complex), 1.40–1.75 (2H, complex), 2.49 (1H, dd, J=16.1 and 4.4 Hz), 2.79 (1H, dd, J=16.1 and 9.3 Hz), 2.88 (1H, m), 5.12 (1H, d, J=12.7 Hz), 5.17 (1H, d, J=12.7 Hz), 7.25–71.41 (5H, complex)

IR absorption spectrum (liquid film) cm⁻¹: 2926 (s), 1737 (s), 1713 (s)

Mass Spectrum [M]⁺=348

High resolution MS spectrum [M]⁺=348.2308 ($C_{21}H_{32}O_4$); Calcd. value: 348.2300 $[\alpha]_D^{26}$=+2.8° (c=1.0, EtOH)

Referential Example 85

2,2,2-Trichloroethyl 3-(R)-benzyloxycarbonyltridecanoate

Following the procedure described in Referential Example 8, but using 3-(R)-benzyloxycarbonyltridecanoic acid (9.35 g), prepared in Referential Example 84, and trichloroethanol (11.0 ml), the desired compound (10.86 g) was obtained.

$C_{23}H_{33}O_4Cl_3$ (FW=478, Cl=35)

NMR spectrum (270 MHz, $CDCl_3$) δ ppm: 0.88 (3H, t, J=6.6 Hz), 1.13–1.39 (16H, complex), 1.48–1.79 (2H, complex), 2.60 (1H, dd, J=15.1 and 3.4 Hz), 2.81–3.02 (2H, complex), 4.65 (1H, d, J=12.0 Hz), 4.72 (1H, d, J=12.0 Hz), 5.10 (1H, d, J=12.4 Hz), 5.18 (1H, d, J=12.4 Hz), 7.28–7.42 (5H, complex)

IR absorption spectrum (liquid film) cm⁻¹: 2926 (s), 1759 (s), 1737 (s)

Mass spectrum [M]⁺=478

High resolution MS spectrum [M]⁺=478.1428 ($C_{23}H_{33}H_4$ ($^{35}Cl)_3$); Calcd. value: 478.1445 $[\alpha]_D^{26}$=−0.57° (c=3.0, $CHCl_3$)

Referential Example 86

2-(R)-(2,2,2-Trichloroethoxycarbonyl)methyldodecanoic acid

Following the procedure described in Referential Example 9, but using 2,2,2-trichloroethyl 3-(R)-benzyloxycarbonyltridecanoate (10.78 g), prepared in Referential Example 65, the desired compound (7.01 g) was obtained.

$C_{16}H_{27}O_4Cl_3$ (FW=388, Cl=35)

NMR spectrum (270 MHz, $CDCl_3$) δ ppm: 0.88 (3H, t, J=6.5 Hz), 1.15–1.45 (16H, complex), 1.50–1.82 (2H, complex), 2.61 (1H, dd, J=15.2 and 2.2 Hz), 3.80–3:01 (2H, complex), 4.72 (1H, d, J=11.9 Hz), 4.79 (1H, d, J=11.9 Hz)

IR absorption spectrum (liquid film) cm⁻¹: 2927 (s), 1759 (s), 1710 (s)

Mass spectrum [M+H]⁺=389

High resolution MS spectrum [M+H]⁺=389.1036 ($C_{16}H_{28}O_4$ ($^{35}Cl)_3$); Calcd. value: 389.1053 $[\alpha]_D^{26}$=+11.7° (c=1.0, EtOH)

Referential Example 87

$N^1$-Benzyloxycarbonyl-$N^2$-[1-oxo-2-(R)-(2,2,2-trichloroethoxycarbonyl)methyldodecyl]-(S)-piperazic acid tert-butyl ester Following the procedure described in Referential Example 10, but using an acid chloride of 2-(R)-(2,2,2-trichloroethoxycarbonyl)methyldodecanoic acid (329 mg), prepared in Referential Example 66, and -(S)-N'-benzyloxycarbonylpiperazic acid tert-butyl ester desired compound (492 mg) was obtained.

$C_{33}H_{49}O_7N_2Cl_3$ (FW=690, Cl=35)

NMR spectrum (270 MHz, $CDCl_3$) δ ppm: 0.88 (3H, t, J=6.6 Hz), 0.94–1.39 (18H, complex), 1.43 (9H, s), 1.49–1.71 (2H, complex), 1.78–2.13 (2H, complex), 2.60

(1H, dd, J=17.5 and 3.6 Hz), 2.94 (1H, dd, J=17.5 and 10.9 Hz), 3.14 (1H, m), 3.43 (1H, m), 4.27 (1H, m), 4.61 (1H, d, J=11.9 Hz), 4.77 (1H, d, J=11.9 Hz), 5.14 (1H, d, J=11.9 Hz), 5.21 (1H, d, J=11.9 Hz), 5.27 (1H, t, J=4.0 Hz), 7.23–7.41 (5H, complex)

IR absorption spectrum (liquid film) cm$^{-1}$: 2927 (s), 1740 (s), 1677 (s)

Mass spectrum [M]$^+$=690

High resolution MS spectrum [M]$^+$=690.2598 ($C_{33}H_{49}O_7N_2$ ($^{35}Cl$)$_3$); Calcd. value: 690.2606 [α]$_D^{26}$=−7.0° (c=2.0, CHCl$_3$)

Referential Example 88

$N^1$-benzyloxycarbonyl-$N^2$-[2-(R)-carboxymethyl-1-oxododecyl]-(S)-piperazic acid tert-butyl ester Following the procedure described in Referential Example 11, but using $N^1$-benzyloxycarbonyl-$N^2$-[1-oxo-2-(R)-(2,2,2-trichloroethoxycarbonyl)methyldodecyl]-(S)-piperazic acid tert-butyl ester (489 mg), prepared in Referential Example 87, there was obtained the desired compound (407 mg).

$C_{31}H_{48}O_7N_2$ (FW=560)

NMR spectrum (270 MHz, CDCl$_3$) δ ppm: 0.88 (3H, t, J=6.6 Hz), 0.94–2.11 (22H, complex), 1.43 (9H, s), 2.48 (1H, dd, J=17.5 and 3.6 Hz), 2.82 (1H, dd, J=17.5 and 10.9 Hz), 3.07 (1H, m), 3.31 (1H, br.t, J=10.1 Hz), 4.25 (1H, m), 5.13 (1H, d, J=11.8 Hz), 5.20 (1H, d, J=11.8 Hz), 5.27 (1H, dd, J=5.3 and 3.3 Hz), 7.23–7.40 (5H, complex)

IR absorption spectrum (liquid film) cm$^{-1}$: 3185 (w), 2927 (s), 1.736 (s), 1678 (s)

Mass spectrum [M–tBuO]$^+$=487

High resolution MS spectrum [M–tBuO]$^+$=487.2820 ($C_{27}H_{39}O_6N_2$); Calcd. value: 487.2808 [α]$_D^{26}$=20.5° (c=1.0, EtOH)

Referential Example 89

$N^1$-benzyloxycarbonyl-$N^2$-[2-(R)-(benzyloxyaminocarbonyl)methyl-1-oxododecyl]-(S)-piperazic acid tert-butyl ester Following the procedure described in Referential Example 12, but using $N^1$-benzyloxycarbonyl-$N^2$-[2-(R)-carboxymethyl-1-oxododecyl]-(S)-piperazic acid tert-butyl ester(403 mg), prepared in Referential Example 88, and O-benzylhydroxylamine, the desired compound was obtained (463 mg).

$C_{38}H_{55}O_7N_3$ (FW=665)

NMR spectrum (270 MHz, CDCl$_3$) δ ppm: 0.88 (3H, t, J=6.6 Hz), 0.94–2.45 (24H, complex), 1.42 (9H, s), 3.21 (1H, m), 3.46 (1H, m), 4.23 (1H, m), 4.82 (1H, d, J=11.2 Hz), 4.87 (1H, d, J=11.2 Hz), 5.13 (1H, d, J=12.5 Hz), 5.20 (1H, d, J=12.5 Hz), 5.24 (1H, m), 7.20–7.49 (10H, complex), 8.41 (1H, m)

IR absorption spectrum (liquid film) cm$^{-1}$: 3252 (w), 2927 (s), 1733 (s), 1675 (s)

Mass spectrum [M+H]$^+$=666

High resolution MS spectrum [M+H]$^+$=666.4136 ($C_{36}H_{56}O_7N_3$); Calcd. value: 666.4118 [α]$_D^{26}$=−36.2° (c=1.0, CHCl$_3$)

Referential Example 90

$N^1$-Benzyloxycarbonyl-$N^2$-[2-(R)-(benzyloxyaminocarbonyl)methyl-1-oxododecyl]-(S)-piperazic acid Following the procedure described in Referential Example 13, but using $N^1$-benzyloxycarbonyl-$N^2$-[2-(R)-benzyloxyaminocarbonyl)methyl-1-oxododecyl]-(S)-piperazic acid tert-butyl ester (457 mg), prepared in Referential Example 89, the desired compound (370 mg) was obtained.

$C_{34}H_{47}O_7N_3$ (FW=609)

NMR spectrum (270 MHz, CDCl$_3$) δ ppm: 0.88 (3H, t), 0.96–1.38 (16H, complex), 1.38–1.69 (3H, complex), 1.82–2.06 (2H, complex), 2.21–2.59 (2H, complex), 2.90–3.18 (3H, complex), 4.11 (1H, br.d, J=12.5 Hz), 4.85 (1H, br.s), 4.89–5.08 (3H, complex), 5.17 (1H, d, J=11.9 Hz), 7.02–7.51 (11H, complex), 12.32 (1H, s)

IR absorption spectrum (liquid kBr pellet): 3231 (w), 2926 (s), 1710 (s), 1672 (s), 1604 (s) [α]$_D^{26}$=−28.1° (c=1.0, EtOH)

Referential Example 91

4-(S)-Isopropyl-3-(1-oxo-4-phenylbutyl)-2-oxazolidinone

Following the procedure described in Referential Example 3, but using 4-(S)-isopropyl-2-oxazolidinone (6.88 g) and 4-phenylbutyryl chloride (6.88 g), the desired compound (10.23 g) was obtained as a colorless oil.

$C_{16}H_{21}O_3N$ (FW=275)

NMR spectrum (270 MHz, CDCl$_3$) δ ppm: 0.86 (3H, d, J=6.6 Hz), 0.91 (3H, d, J=6.6 Hz), 1.85–2.21 (2H, complex), 2.36 (1H, d,hep, J=6.6 and 4.0 Hz), 2.69 (2H, t, J=7.9 Hz), 2.91 (1H, dt, J=17.2.and 7.3 Hz), 3.02 (1H, dr, J=17.2 and 7.3 Hz), 4.18 (1H, dd, J=8.6 and 4.0 Hz), 4.24 (1H, t, J=8.6 Hz), 4.41 (1H, dt, J=8.6 and 4.0 Hz), 7.12.–7.36 (5H, complex)

IR absorption spectrum (liquid film) cm$^{-1}$: 2964 (m), 1781 (s), 1701 (s)

Mass spectrum [M]$^+$=275

High resolution MS spectrum [M]$^+$=275.1507 ($C_{16}H_{21}O_3N$); Calcd. value: 275.1522 [α]$_D^{26}$=+60.6° (c=1.0, CHCl$_3$)

Referential Example 92

4-(S)-Isopropyl-3-[2-(R)-tert-butoxycarbonylmethyl-1-oxo-4-phenylbutyl]-2-oxazolidinone Following the procedure described in Referential Example 4, but using 4-(S)-isopropyl-3-(1-oxo-4-phenylbutyl)-2-oxazolidinone (8.83 g), prepared in Referential Example 91, and tert-butyl bromoacetate (25.0 ml), there was obtained the desired compound (7.35 g).

$C_{22}H_{31}NO_5$ (FW=389)

NMR spectrum (270 MHz, CDCl$_3$) δ ppm: 0.89 (3H, d, J=6.9 Hz), 0.91 (3H, d, J=6.9 Hz), 1.42 (9H, s), 1.78 (1H, m), 2.01 (1H, m), 2.35 (1H, m), 2.47 (1H, dd, J=16.5 and 4.6 Hz), 2.57–2.74 (2H, complex), 2.81 (1H, dd, J=16.5 and 9.9 Hz), 4.08–4.37 (4H, complex), 7.11–7.32 (5H complex)

IR absorption spectrum (liquid kBr pellet): 2978 (w), 1767 (s), 1730 (s), 1691 (s)

Mass spectrum [M]$^+$=389

High resolution MS spectrum [M]$^+$=389.2208 ($C_{22}H_{31}O_5N$); Calcd. value: 389.2202 m.p. 64°–66° (H$_2$O—MeOH) [α]$_D^{26}$=+51.6° (c=1.0, CHCl$_3$)

Referential Example 93 tert-Butyl 3-(R)-benzyloxycarbonyl-5-phenylpentanoate

Following the procedure described in Referential Example 63, using 4-(S)-isopropyl-3-[2-(R)-tertbutoxycarbonylmethyl-1-oxo-4-phenylbutyl)-2-oxazolidinone (5.11 g), prepared in Referential Example 92, the desired compound (4.45 g) was obtained.

$C_{23}H_{28}O_4$ (FW=368)

NMR spectrum (270 MHz, $CDCl_3$) δ ppm: 1.40 (9H, s), 1.83 (1H, m), 1.97 (1H, m), 2.41 (1H, dd, J=16.5 and 3.3 Hz), 2.52–2.64 (2H, complex), 2.69 (1H, dd, J=16.5 and 8.6 Hz), 2.89 (1H, m), 5.11 (1H, d, J=12.2 Hz), 5.19 (1H, d, J=12.2 Hz), 7.06–7.44 (10H, complex)

IR absorption spectrum (liquid film) $cm^{-1}$: 2978 (m), 1731 (s), 1604 (w)

Mass spectrum $[M]^+$=368

High resolution MS spectrum $[M]^+$=368.1997 ($C_{23}H_{28}O_4$); Calcd. value: 368.1988 $[α]_D^{26}$=+13.0° (c=4.2, $CHCl_3$)

Referential Example 94

3-(R)-Benzyloxycarbonyl-5-phenylpentanoic acid

Following the procedure described in Referential Example 7, but using tert-butyl 3-(R)-benzyloxycarbonyl-5-phenylpentanoate (4.40 g), prepared in Referential Example 93, the desired compound (3.17 g) was obtained.

$C_{19}H_{20}O_4$ (FW=312)

NMR spectrum (270 MHz, $CDCl_3$) δ ppm: 1.77–2.10 (2H, complex), 2.53 (1H, dd, J=15.5 and 3.6 Hz), 2.55–2.70 (2H, complex), 2.83 (1H, dd, J=15.5 and 9.2 Hz), 2.92 (1H, m), 5.12 (1H, d, J=12.5 Hz), 5.18 (1H, d, J=12.5 Hz), 7.06–7.42 (10H, complex)

IR absorption spectrum (liquid film) $cm^{-1}$: 3031 (m), 1736 (s), 1710 (s), 1604 (w)

Mass spectrum $[M+H]^+$=313

High resolution MS spectrum $[M+H]^+$=313.1462 ($C_{19}H_{21}O_4$); Calcd. value: 313.1440 $[α]_D^{26}$=+16.0° (c=1.4, EtOH)

Referential Example 95

2,2,2-Trichloroethyl 3-(R)-benzyloxycarbonyl-5-phenylpentanoate

Following the procedure described in Referential Example 8, but using 3-(R)-benzyloxycarbonyl-5-phenylpentanoic acid (3.13 g), prepared in Referential Example 94, and trichloroethanol (4.3 ml), the desired compound (4.07 g) was obtained.

$C_{21}H_{21}O_4Cl_3$ (FW=442, Cl=35)

NMR spectrum (270 MHz, $CDCl_3$) δ ppm: 1.80–2.12 (2H, complex), 2.51–2.83 (3H, complex), 2.88–3.09 (2H, complex), 4.66 (1H, d, J=11.9 Hz), 4.71 (1H, d, J=11.9 Hz), 5.12 (1H, d, J=12.5 Hz), 5.19 (1H, d, J=12.5 Hz), 7.04–7.45 (10H, complex)

IR absorption spectrum (liquid film) $cm^{-1}$: 2958 (w), 2947 (w), 1754 (s), 1733 (s)

Mass spectrum $[M]^+$=442

High resolution MS spectrum $[M]^+$=442.0498 ($C_{21}H_{21}O_4$ ($^{35}Cl)_3$); Calcd. value: 442.0505 $[α]_D^{26}$=+9.8° (c=3.1, $CHCl_3$)

Referential Example 96

2-(R)-(2,2,2-Trichloroethoxycarbonyl)methyl-4-phenylbutyric acid

Following the procedure described in Referential Example 9, but using 2,2,2-trichloroethyl 3-(R)-benzyloxycarbonyl-5-phenylpentanoate (4.01 g), prepared in Referential Example 95, the desired compound (2.54 g) was obtained.

$C_{14}H_{15}O_4Cl_3$ (FW=352, Cl=35)

NMR spectrum (270 MHz, $CDCl_3$) δ ppm: 1.92 (1H, m), 2.10 (1H, m), 2.56–2.80 (3H, complex), 2.83–3.08 (2H, complex), 4.72 (1H, d, J=12.2 Hz), 4.78 (1H, d, J=12.2 Hz), 7.11–7.38 (5H, complex)

IR absorption spectrum (liquid film, kBr pellet) $cm^{-1}$: 3221 (m), 2951 (m), 1754 (s), 1731 (s), 1694 (s)

Mass spectrum $[M]^+$=352

High resolution MS spectrum $[M]^+$=352.0013 ($C_{14}H_{15}O_4$ ($^{35}Cl)_3$); Calcd. value: 352.0035 m.p. 59°–61° C. ($H_2O$—MeOH) $[α]_D^{26}$=+21.1° (c=17, EtOH)

Referential Example 97

$N^1$-Benzyloxycarbonyl-$N^2$-[1-oxo-2-(R)-(2,2,2-trichloroethoxycarbonyl)methyl-4-phenylbutyl]-(S)-piperazic acid tert-butyl ester Following the procedure described in Referential Example 10, but using an acid chloride of 2-(R)-(2,2,2-trichloroethoxycarbonyl)methyl-4-phenylbutyric acid (353 mg), prepared in Referential Example 96, and (S)-$N^1$-benzyloxycarbonylpiperazic acid tert-butyl ester (8 mg), the desired compound (492 mg) was obtained.

$C_{31}H_{37}O_7Cl_3$ (FW=654)

NMR spectrum (270 MHz, $CDCl_3$) δ ppm: 1.42 (9H, s), 1.47–2.19 (6H, complex), 2.31–2.60 (2H, complex), 2.65 (1H, dd, J=17.2 and 4.0 Hz), 3.02 (1H, dd, J=17.2 and 10.6 Hz), 3.22 (1H, m), 3.38 (1H, m), 4.21 (1H, m), 4.63 (1H, d, J=11.9 Hz), 4.78 (1H, d, J=11.9 Hz), 5.16 (2H, s), 5.27 (1H, m), 7.05–7.42 (10H, complex)

IR absorption spectrum (liquid film) $cm^{-1}$: 2955 (m), 1735 (s), 1676 (s)

Mass spectrum $[M+H]^+$=655

High resolution MS spectrum $[M+H]^+$=655.1721 ($C_{31}H_{38}O_7N_2$ ($^{35}Cl)_3$); Calcd. value: 655.1745 $[α]_D^{26}$=−16.4° (c=1.0, $CHCl_3$)

Referential Example 98

$N^1$-benzyloxycarbonyl-$N^2$-[2-(R)-carboxymethyl-1-oxo-4-phenylbutyl]-(S)-piperazic acid tert-butyl ester Following the procedure described in Referential Example 11, but using $N^1$-benzyloxycarbonyl-$N^2$-[1-oxo-2-(R)-(2,2,2-trichloroethoxycarbonyl)methyl-4-phenylbutyl]-(S)-piperazic acid tert-butyl ester (330 mg) prepared in Referential Example 97, there was obtained the desired compound (231 mg).

$C_{29}H_{36}O_7N_2$ (F=524)

NMR spectrum (270 MHz, $CDCl_3$) δ ppm: 1.42 (9H, s), 1.43–2.19 (6H, complex), 2.27–2.73 (2H, complex), 2.52 (1H, dd, J=17.2 and 3.6 Hz), 2.88 (1H, dd, J=17.2 and 10.6 Hz), 3.02–3.47 (2H, complex), 4.20 (1H, m), 5.15 (2H, s), 5.26 (1H, br.dd, J=4.6 and 3.3 Hz), 6.79–7.41 (10H, complex)

IR absorption spectrum (liquid film) $cm^{-1}$: 2977 (m), 1733 (s), 1676 (s)

Mass spectrum $[M]^+$=524

High resolution MS spectrum $[M+H]^+$=525.2593 ($C_{29}H_{37}O_7N_2$); Calcd. value: 525.2601 $[α]_D^{26}$=−29.5° (c=1.0, EtOH)

Referential Example 99

N$^1$-Benzyloxycarbonyl-N$^2$-[2-(R)-(benzyloxyaminocarbonyl)methyl-1-oxo-4-phenylbutyl]-(S)-piperazic acid tert-butyl ester Following the procedure described in Referential Example 12, but using N$^1$-benzyloxycarbonyl-N$^2$-[2-(R)-carboxymethyl-1-oxo-4-phenylbutyl]-(S)-piperazic acid tert-butyl ester (228 mg), prepared in Referential Example 98, and O-benzylhydroxylamine, the desired compound (260 mg) was obtained.

C$_{36}$H$_{43}$O$_7$N$_3$ (FW=629)

NMR spectrum (270 MHz, CDCl$_3$) δ ppm: 1.30–2.78 (10H, complex), 1.42 (9H, s), 3.14–3.54 (2H, complex), 4.24 (1H, m), 4.83 (1H, d, J=11.7 Hz), 4.88 (1H, d, J=11.7 Hz), 5.15 (2H, s), 5.26 (1H, m), 7.05–7.48 (15H, complex), 8.15 (1H, m)

IR absorption spectrum (liquid film) cm$^{-1}$: 3252 (w), 2977 (m), 1732 (s), 1672 (s)

Mass spectrum [M+H]$^+$=630

High resolution MS spectrum [M+H]$^+$=630.3162 (C$_{36}$H$_{44}$O$_7$N$_3$); Calcd. value: 630.3179

Referential Example 100

N$^1$-Benzyloxycarbonyl-N$^2$-[2-(R)-(benzyloxyaminocarbonyl)methyl-1-oxo-4-phenylbutyl]-(S)-piperazic acid tert-butyl ester Following the procedure described in Referential Example 13, but using N$^1$-benzyloxycarbonyl-N$^2$-[2-(R)-benzyloxyaminocarbonyl)methyl-1-oxo-4-phenylbutyl]-(S)-piperazic acid tert-butyl ester (260 mg), prepared in Referential Example 99, the desired compound (230 mg) was obtained, containing impurities but which could be used in the following reaction (Example 20) without further purification.

Referential Example 101

N$^1$-Benzyloxycarbonyl-N$^2$-[2-(R)-(benzyloxyaminocarbonyl)methyl-4-methyl-1-oxopentyl]-(S)-piperazic acid Following the procedure described in Referential Example 13, but using N$^1$-benzyloxycarbonyl-N$^2$-[2-(R)-benzyloxyaminocarbonyl)methyl-4-methyl-1-oxopentyl]-(S)-piperazic acid tert-butyl ester (401 mg), prepared in Referential Example 46, the desired compound (375 mg) was obtained, having a small amount of impurities, but which was able to be used in the following reactions (Examples 32 and 36) without further purification.

Referential Example 102

2-(S)-(2,2,2-Trichloroethoxycarbonyl)methylheptanoic acid

Following the synthetic procedures (Referential Example 3, 4, 5, 6, 7, 8 and 9) of the corresponding compounds having R-configuration using 4-(R)-isopropyl-2-oxazolidinone and heptanoyl chloride as starting materials, the desired compound was synthesized.

NMR spectrum (270 MHz, CDCl$_3$) δ ppm: 0.89 (3H, t, J=6.5 Hz), 1.18–1.47 (6H, complex), 1.47–1.82 (2H, complex), 2.61 (1H, dd, J=15.2 and 2.9 Hz), 2.88 (1H, dd, J=15.2 and 9.3 Hz), 2.94 (1H, m), 4.72 (1H, d, J=12.0 Hz), 4.79 (1H, d, J=12.0 Hz)

IR absorption spectrum (liquid film) cm$^{-1}$: 1758 (s), 1709 (s)

High resolution MS spectrum [M+H]$^+$=319.0261 (C$_{11}$H$_{18}$O$_4$Cl$_3$); Calcd. value: 319.0271 [α]$_D^{26}$=−11.2 (c=3.96)

Referential Example 103

N$^1$-benzyloxycarbonyl-N$^2$-[1-oxo-2-(S)-(2,2,2-trichloroethoxycarbonyl)methylheptyl]-(S)-piperazic acid tert-butyl ester Following the procedure described in Referential Example 10, but using an acid chloride of 2-(S)-(2,2,2-trichloroethoxycarbonyl)methylheptanoic acid (413 mg), prepared in Referential Example 102 and (S)-N$^1$-benzyloxycarbonylpiperazic acid tert-butyl ester (420 mg), the desired compound (675 mg) was obtained.

NMR spectrum (270 MHz, CDCl$_3$) δ ppm: 0.85 (3H, t, J=6.6 Hz), 0.97–2.14 (12H, complex), 1.43 (3H, s), 2.50 (1H, dd, J=17.5 and 4.9 Hz), 2.95 (1H, dd, J=17.5 and 9.9 Hz), 2.97 (1H, m), 3.28 (1H, m), 4.40 (1H, m), 4.58 (1H, d, J=12.5 Hz), 4.85 (1H, d, J=12.5 Hz), 5.10 (1H, d, J=12.5 Hz), 5.21 (1H, d, J=12.5 Hz), 5.29 (1H, br.d, J=4.3 Hz), 7.22–7.42 (5H, complex)

IR absorption spectrum (liquid film) cm$^{-1}$: 2931 (m), 1735 (s), 1677 (s)

High resolution MS spectrum [M]$^+$=620.1833 (C$_{28}$H$_{39}$N$_2$O$_7{}^{35}$Cl$_3$); Calcd. value: 620.1823

Referential Example 104

N$^1$-benzyloxycarbonyl-N$^2$-[2-(S)-carboxymethyl-1-oxoheptyl]-(S)-piperazic acid tert-butyl ester Following the procedure described in Referential Example 11, but using N$^1$-benzyloxycarbonyl-N$^2$-[1-oxo-2-(S)-(2,2,2-trichloroethoxycarbonyl)methylheptyl]-(S)-piperazic acid tert-butyl ester (670 mg), prepared in Referential Example 103, the desired compound (489 mg) was obtained.

NMR spectrum (270 MHz, CDCl$_3$) δ ppm: 0.84 (3H, t, J=6.6 Hz), 0.94–2.17 (12H, complex), 1.42 (9H, s), 2.37 (1H, m), 2.80–3.09 (2H, complex), 3.18 (1H, m), 4.39 (1H, m), 5.00–5.36 (3H, complex), 7.18–7.42 (5H, complex)

IR absorption spectrum (liquid film) cm$^{-1}$: 3190 (w), 2932 (s), 1735 (s), 1679 (s)

High resolution MS spectrum [M+H—H$_2$O]$^+$=473.2672 (C$_{26}$H$_{37}$N$_2$O$_6$); Calcd. value: 473.2652

Referential Example 105

N$^1$-benzyloxycarbonyl-N$^2$-[2-(S)-(benzyloxyaminocarbonyl)methyl-1-oxoheptyl]-(S)-piperazic acid tert-butyl ester Following the procedure described in Referential Example 12, but using N$^1$-benzyloxycarbonyl-N$^2$-[2-(S)-carboxymethyl-1-oxoheptyl]-(S)-piperazic acid tert-butyl ester(489 mg), prepared in Referential Example 104, and O-benzylhydroxylamine, the desired compound (432 mg) was obtained.

NMR spectrum (270 MHz, CDCl$_3$) δ ppm: 0.87 (3H, t, J=6.6 Hz), 0.93–2.38 (14H, complex), 1.42 (9H, s), 2.81–3.32 (2H, complex), 4.32 (1H, m), 4.75–4.95 (2H, complex), 5.10 (1H, d, J=11.9 Hz), 5.20 (1H, d, J=11.9 Hz), 5.27 (1H, m), 7.22–7.46. (10H, complex)

IR absorption spectrum (liquid film) cm$^{-1}$: 3252 (m), 2931 (s), 1735 (s), 1675 (s)

High resolution MS spectrum [M+H]$^+$=596.3327 (C$_{33}$H$_{46}$N$_3$O$_7$); Calcd. value: 596.3335 [α]$_D^{26}$=+37.1° (c=1.00, EtOH)

Referential Example 106

N$^1$-Benzyloxycarbonyl-N$^2$-[2-(S)-(benzyloxyaminocarbonyl)methyl-1-oxoheptyl]-(S)-piperazic acid Following the procedure described in Referential Example 13, but using N$^1$-benzyloxycarbonyl-N$^2$-[2-(S)-(benzyloxycarbonyl)methyl-1-oxoheptyl]-(S)-piperazic acid tert-butyl ester (377 mg), prepared in Referential Example 105, there was obtained the desired compound (301 mg).

NMR spectrum (270 MHz, CDCl$_3$) δ ppm: 0.83 (3H, t, J=5.8 Hz), 0.97–2.20 (15H, complex), 3.14 (1H, m), 4.24 (1H, m), 4.70–4.95 (2H, br.s), 5.02–5.33 (3H, complex), 7.18–7.48 (10H, complex)

IR absorption spectrum (liquid film) cm$^{-1}$: 3230 (w), 2940 (m), 1720 (s), 1655 (s) [α]$^{D26}$=+21.4° (c=1.0, EtOH)

Referential Example 107

N$^1$-benzyloxycarbonyl-N$^2$-[1-oxo-2-(R)-(2,2,2-trichloroethoxycarbonyl)methyl-4-methylpentyl]-(S)-piperazic acid tert-butyl ester Following the procedure described in Referential Example 10, but using 2-(R)-(2,2,2-trichloroethoxycarbonyl)methyl-4-methylpentanoic acid (405 mg), prepared in Referential Example 44, and (S)-N$^1$-benzyloxycarbonylpiperazic acid tert-butyl ester (421 mg) as starting materials, the desired compound (632 mg) was obtained.

NMR spectrum (270 MHz, CDCl$_3$) δ ppm: 0.87 (3H, d, J=6.6 Hz), 0.94 (3H, d, J=6.6 Hz), 1.10–1.71 (4H, complex), 1.43 (9H, s), 1.73–2.15 (3H, complex), 2.62 (1H, dd, J=17.2 and 3.8 Hz), 2.91 (1H, dd, J=17.2 and 10.9 Hz), 3.23 (1H, dd, J=10.5 and 7.7 Hz), 3.47 (1H, dd, J=12.2 and 9.7 Hz), 4.28 (1H, m), 4.61 (1H, d, J=12.5 Hz), 4.77 (1H, d, J=12.5 Hz), 5.14 (1H, d, J=12.5 H), 5.21 (1H, d, J=12.5 Hz), 5.26 (1H, t, J=4.3 Hz), 7.27–7.42 (5H, complex)

IR absorption spectrum (liquid film) cm$^{-1}$: 2960 (m), 1735 (s), 1675 (s)

High resolution MS spectrum [M]$^+$=606.1664 (C$_{27}$H$_{37}$N$_2$O$_7$$^{35}$Cl$_3$); Calcd. value: 606.1667 [α]$_D^{26}$=−4.3° (c=1.00, CHCl$_3$)

Referential Example 108

N$^2$-[2-[2-(R)-(Hydroxyaminocarbonyl)methyl-1-oxoheptyl-(S)-piperazic acid (4S,5S)-5-methyl-3-oxoheptan-4-ylamide Following the procedure described in Referential Example 1, the protecting groups of N$^1$-benzyloxycarbonyl-N$^2$-[2-(R)-(benzyloxyaminocarbonyl)methyl-1-oxoheptyl]-(S)-piperazic acid (4S,5S)-5-methyl-3-oxoheptan-4-ylamide (64 mg), prepared in Referential Example 17, were removed by catalytic reduction. The product was purified by preparative reverse phase thin layer chromatography through silica gel (20×20 cm size, 0.25 mm thick), using a 4:6 mixture of water and methanol as a developing solvent and methanol as an eluent, to give the desired compound (35 mg), having a m.p. of 69°–72° C. after recrystallization from a mixture of hexane and ethyl° acetate.

NMR spectrum (270 MHz, CDCl$_3$) δ ppm: 0.85 (3H, t, J=6.7 Hz), 0.87 (3H, t, J=6.1 Hz), 0.92 (3H, d, J=6.7 Hz), 1.00–2.00 (15H, complex), 1.09 (3H, t, J=7.3 Hz), 2.31 (1H, dd, J=12.0 and 4.4 Hz), 2.49 (1H, br.t, J=12.0 Hz), 2.55 (2H, q, J=7.3 Hz), 2.83 (1H, m), 3.01 (1H, br.d, J=12.8 Hz), 3.95 (1H, m), 4.64 (1H, dd, J=8.5 and 4.9 Hz), 4.75 (1H, br.d, J=12.8 Hz), 5.31 (1H, br.s), 7.38 (1H, br.s)

IR absorption spectrum (liquid film) cm$^{-1}$: 3303 (m), 1714 (m), 1667 (s), 1626 (s)

High resolution MS spectrum [M+2H—H$_2$O]$^+$=424.3072 (C$_{22}$H$_{40}$N$_4$O$_4$); Calcd. value: 424.3055 [α]$_D^{26}$=−30.7° (c=1.01, EtOH)

Referential Example 109

N$^2$-[2-(R)-(Hydroxyaminocarbonyl)methyl-1-oxoheptyl]-(S)-piperazic acid (4R,5R)-5-methyl-3-oxoheptan-4-ylamide Following the procedure described in Referential Example 1, the protecting groups of N$^1$-benzyloxycarbonyl-N$^2$-[2-(R)-(benzyloxyaminocarbonyl)methyl-1-oxoheptyl]-(S)-piperazic acid (4S,5S)-5-methyl-3-oxoheptan-4-yalmide (37 mg), prepared in Referential Example 20, were removed by catalytic reduction. The product was purified by preparative thin layer chromatography through silica gel (20×20 cm size, 0.5 mm thick), using a 15:1 mixture of chloroform and methanol as a developing solvent and a 10:1 mixture of ethyl acetate and methanol as an eluent, to give the desired compound (19 mg).

NMR spectrum (270 MHz, CDCl$_3$) δ ppm: 0.77–0.93 (6H, complex), 0.97 (3H, d, J=6.6 Hz), 1.06 (3H, t, J=7.3 Hz), 1.15–2.63 (17H, complex), 2.52 (2H, q), 2.7014 3.19 (2H, complex), 3.95 (1H, m), 4.47–4.73 (2H, complex), 5.25 (1H, s), 6.81 (1H, d, J=8.6 Hz), 7.70–8.80 (1H, br.s), 9.54 (1H, br.s)

IR absorption spectrum (liquid film) cm$^{-1}$: 3274 (m), 2933 (s), 1718 (m), 1665 (s), 1628 (s)

Mass spectrum m/z [M]$^+$=440

High resolution MS spectrum [M−H$_3$NO]$^+$=407.2791 (C$_{22}$H$_{37}$N$_3$O$_4$); Calcd. value: 407.2784 [α]$_D^{26}$=+2.7° (c=0.99, EtOH)

Referential Example 110

N$^2$-[2-(R)-(Hydroxyaminocarbonyl)methyl-1-oxoheptyl]-(R)-piperazic acid (4S,5S)-methyl-3-oxoheptan-4-ylamide Following the procedure described in Referential Example 1, the protecting groups of N$^1$-benzyloxycarbonyl-N$^2$-[2-(R)-(benzyloxyaminocarbonyl)methyl-1-oxoheptyl]-(R)-piperazic acid (4R,5R)-5-methyl-3-oxoheptan-4-ylamide (67 mg), prepared in Referential Example 31, were removed by catalytic reduction. The product was purified by preparative thin layer chromatography through silica gel (20×20 cm size, 0.5 mm thick), using a 20:1 mixture of chloroform and methanol twice as a developing solvent and a 10:1 mixture of ethyl acetate and methanol as an eluent to, give the desired compound (41 mg).

NMR spectrum (270 MHz, CDCl$_3$) δ ppm: 0.80–0.92 (6H, complex), 0.95 (3H, d, J=6.6 Hz), 1.06 (3H, t, J=7.3 Hz), 1.10–2.87 (15H, complex), 2.59 (2H, q, J=7.3 Hz), 3.79 (1H, br.d, J=13.9 Hz), 4.02 (1H, m), 4.35 (1H, br.d, J=12.5 Hz), 4.62 (1H, dd, J=8.2, 5.6 Hz), 5.29 (1H, d, J=3.3 Hz), 7.64 (1H, d, J=17.9 Hz), 9.43 (1H, br.s)

IR absorption spectrum (liquid film) cm$^{-1}$: 3270 (s), 2933 (s), 1716 (s), 1650 (s), 1630 (s)

High resolution MS spectrum [M]⁺=440.3032 ($C_{22}H_{40}N_4O_5$); Calcd. value: 440.3299 [ ]$_D^{26}$=+47.2° (c=1.00, EtOH)

Referential Example 111

[2-[2-(R)-(2-Hydroxyamino-2-oxoethyl)-1-oxoheptyl]-(R)-piperazic acid (4R,5R)-5-methyl-3-oxoheptan-4-ylamide Following the procedure described in Referential Example 1, the protecting groups of $N^1$-benzyloxycarbonyl-$N^2$-[2-(R)-(2-benzyloxyamino-2-oxoethyl)-1-oxoheptyl]-(R)-piperazic acid (4R,5R)-5-methyl-3-oxoheptan-4-ylamide (54 mg), prepared in Referential Example 32, was removed by catalytic reduction. The product was purified by preparative thin layer chromatography through silica gel (20×20 cm size, 0.5 mm thick), using a 25:1 mixture of chloroform and methanol as a developing solvent three times, and a 10:1 mixture of ethyl acetate and methanol as an eluent, to give the desired compound (29 mg).

NMR spectrum (270 MHz, $CDCl_3$) δ ppm: 0.78–0.99 (9H, complex), 1.03 (3H, t, J=7.3 Hz), 1.11–1.84 (13H, complex), 2.18 (1H, m), 2.30–2.88 (6H, complex), 3.10 (1H, br.d, J=13.9 Hz), 3.82 (1H, d, J=12.5 Hz), 4.19 (1H, m), 4.64 (1H, dd, J=8.6 and 7.9 Hz), 5.23 (1H, d, J=4.0 Hz), 7.18 (1H, br.d, J=8.6 Hz), 7.79 (1H, br.s), 8.84 (1H, br.s)

IR absorption spectrum (liquid film) cm⁻¹: 3275 (m), 2945 (m), 1715 (m), 1655 (s), 1635 (s)

High resolution MS spectrum [M]⁺=440.2991 ($C_{22}H_{40}N_4O_5$); Calcd. value: 440.2998 [α]$_D^{26}$=+76.4° (c=0.28, EtOH)

Preparation Example 1

Hard-capsule formulation 100 mg of the powdery compound of Example 3, 150 mg of lactose, 50 mg of cellulose and 6 mg of magnesium stearate were mixed and filled into standard 2-piece hard gelatin capsules. The unit capsules were washed and dried.

Preparation Example 2

Tablet formulation 100 mg of the powdery compound of Example 5, 0.2 mg of colloidal silicon dioxide, 5 mg of magnesium stearate, 275 mg of finely crystalline cellulose, 11 mg of starch and 98.8 mg of lactose were mixed and compressed to appropriate size and weight by conventional means. The tablets, if required, were coated.

Preparation Example 3

Injectable agent formulation

The compound of Example 21 (1.5% by volume) was stirred into propylene glycol (10% by volume) and the mixture was dissolved in water at constant volume for injection and sterilized.

Preparation Example 4

Suspension formulation 100 mg of the powdery compound of Example 34, 100 mg of sodium carboxymethylcellulose, 5 mg of sodium benzoate, 1.0 g of sorbitol (Japanese Pharmacopoeia) and 0.025 ml of vanillin were suspended in 5 ml of a suitable medium.

We claim:

1. A compound having the formula:

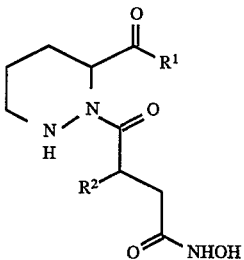

in which:
   $R^1$ represents a group of formula:
   —$NR^4R^5$ wherein $R^4$ and $R^5$ are the same or different and each represents a hydrogen atom or an alkyl group having 1 to 4 carbon atoms; and
   $R^2$ represents an alkyl group having 6 to 10 carbon atoms.

2. A compound selected from the following compounds:
$N^2$-[2-(R)-(hydroxyaminocarbonyl)methyl-1-oxoheptyl]-(S)-piperazic acid N-methylamide,
$N^2$-[2-(R)-(hydroxyaminocarbonyl)methyl-1-oxooctyl]-(S)-piperazic acid N-methylamide,
$N^2$-[2-(R)-(hydroxyaminocarbonyl)methyl-1-oxononyl]-(S)-piperazic acid N-methylamide,
$N^2$-[2-(R)-(hydroxyaminocarbonyl)methyl-1-oxodecyl]-(S)-piperazic acid N-methylamide,
$N^2$-[2-(R)-(hydroxyaminocarbonyl)methyl-1-oxododecyl]-(S)-piperazic acid N-methylamide,
$N^2$-[2-(R)-(hydroxyaminocarbonyl)methyl-1-oxo-4-phenylbutyl]-(S)-piperazic acid N-methylamide,
$N^2$-[2-(R)-(hydroxyaminocarbonyl)methyl-1-oxoheptyl]-(S)-piperazic acid N,N-dimethylamide,
$N^2$-[2-(R)-(hydroxyaminocarbonyl)methyl-1-oxooctyl]-(S)-piperazic acid N,N-dimethylamide,
$N^2$-[2-(R)-(hydroxyaminocarbonyl)methyl-1-oxononyl]-(S)-piperazic acid N,N-dimethylamide,
$N^2$-[2-(R)-(hydroxyaminocarbonyl)methyl-1-oxodecyl]-(S)-piperazic acid N,N-dimethylamide,
$N^2$-[2-(R)-(hydroxyaminocarbonyl)methyl-1-oxododecyl]-(S)-piperazic acid N,N-dimethylamide,
and
$N^2$-[2-(R)-(hydroxyaminocarbonyl)methyl-1-oxo-4-phenylbutyl]-(S)-piperazic acid N,N-dimethylamide.

3. A compound according to claim 2 represented by $N^2$-[2-(R)-(hydroxyaminocarbonyl)methyl-1-oxoheptyl]-(S)-piperazic acid N-methylamide.

4. A compound according to claim 2 represented by $N^2$-[2-(R)-(hydroxyaminocarbonyl)methyl-1-oxooctyl]-(S)-piperazic acid N-methylamide.

5. A compound according to claim 2 represented by $N^2$-[2-(R)-(hydroxyaminocarbonyl)methyl-1-oxononyl]-(S)-piperazic acid N-methylamide.

6. A compound according to claim 2 represented by $N^2$-[2-(R)-(hydroxyaminocarbonyl)methyl-1-oxodecyl]-(S)-piperazic acid N-methylamide.

7. A compound according to claim 2 represented by $N^2$-[2-(R)-(hydroxyaminocarbonyl)methyl-1-oxododecyl]-(S)-piperazic acid N-methylamide.

8. A compound according to claim 2 represented by $N^2$-[2-(R)-(hydroxyaminocarbonyl)methyl-1-oxo-4-phenylbutyl]-(S)-piperazic acid N-methylamide.

9. A compound according to claim 2 represented by $N^2$-[2-(R)-(hydroxyaminocarbonyl)methyl-1-oxoheptyl]-(S)-piperazic acid N,N-dimethylamide.

10. A compound according to claim 2 represented by N$^2$-[2-(R)-(hydroxyaminocarbonyl)methyl-1-oxooctyl]-(S)-piperazic acid N,N-dimethylamide.

11. A compound according to claim 2 represented by N$^2$-[2-(R)-(hydroxyaminocarbonyl)methyl-1-oxononyl]-(S)-piperazic acid N,N-dimethylamide.

12. A compound according to claim 2 represented by N$^2$-[2-(R)-(hydroxyaminocarbonyl)methyl-1-oxodecyl]-(S)-piperazic acid N,N-dimethylamide.

13. A compound according to claim 2 represented by N$^2$-[2-(R)-(hydroxyaminocarbonyl)methyl-1-oxododecyl]-(S)-piperazic acid N,N-dimethylamide.

14. A compound according to claim 2 represented by N$^2$-[2-(R)-(hydroxyaminocarbonyl)methyl-1-oxo-4-phenylbutyl]-(S)-piperazic acid N,N-dimethylamide.

15. An inhibitor of angiogenesis, cancer invasion or cancer metastasis comprising an effective dose of a compound selected from the compounds according to claim 1 in admixture with a pharmaceutically acceptable carrier or vehicle.

16. An inhibitor of angiogenesis, cancer invasion or cancer metastasis comprising an effective dose of a compound selected from the following compounds in admixture with a pharmaceutically acceptable carrier or vehicle:

N$^2$-[2-(R)-(hydroxyaminocarbonyl)methyl-1-oxoheptyl]-(S)-piperazic acid N-methylamide, N$^2$-[2-(R)-(hydroxyaminocarbonyl)methyl-1-oxooctyl]-(S)-piperazic acid N-methylamide, N$^2$-[2-(R)-(hydroxyaminocarbonyl)methyl-1-oxononyl]-(S)-piperazic acid N-methylamide, N$^2$-[2-(R)-(hydroxyaminocarbonyl)methyl-1-oxodecyl]-(S)-piperazic acid N-methylamide, N$^2$-[2-(R)-(hydroxyaminocarbonyl)methyl-1-oxododecyl]-(S)-piperazic acid N-methylamide, N$^2$-[2-(R)-(hydroxyaminocarbonyl)methyl-1-oxo-4-phenylbutyl]-(S)-piperazic acid N-methylamide, N$^2$-[2-(R)-(hydroxyaminocarbonyl)methyl-1-oxoheptyl]-(S)-piperazic acid N,N-dimethylamide, N$^2$-[2-(R)-(hydroxyaminocarbonyl)methyl-1-oxooctyl]-(S)-piperazic acid N,N-dimethylamide, N$^2$-[2-(R)-(hydroxyaminocarbonyl)methyl-1-oxononyl]-(S)-piperazic acid N,N-dimethylamide, N$^2$-[2-(R)-(hydroxyaminocarbonyl)methyl-1-oxodecyl]-(S)-piperazic acid N,N-dimethylamide, N$^2$-[2-(R)-(hydroxyaminocarbonyl)methyl-1-oxododecyl]-(S)-piperazic acid N,N-dimethylamide, and N$^2$-[2-(R)-(hydroxyaminocarbonyl)methyl-1-oxo-4-phenylbutyl]-(S)-piperazic acid N,N-dimethylamide.

\* \* \* \* \*

UNITED STATES PATENT AND TRADEMARK OFFICE
CERTIFICATE OF CORRECTION

PATENT NO.   : 5,643,908
DATED        : July 1, 1997
INVENTOR(S)  : Sugimura et al It is certified that error appears in the above-identified patent and that said Letters Patent is hereby corrected as shown below:

Column 62, line 62: delete in entirety and replace with
-- (benzyloxyaminocarbonyl)methyl-1- --

Signed and Sealed this

Twenty-ninth Day of June, 1999

Attest:

Q. TODD DICKINSON

Attesting Officer

Acting Commissioner of Patents and Trademarks